US012365683B2

(12) United States Patent
Miyazaki et al.

(10) Patent No.: US 12,365,683 B2
(45) Date of Patent: Jul. 22, 2025

(54) LIGHT EMITTING DEVICE AND FUSED POLYCYCLIC COMPOUND FOR LIGHT EMITTING DEVICE

(71) Applicants: Samsung Display Co., Ltd., Yongin-si (KR); KYUSHU UNIVERSITY, NATIONAL UNIVERSITY CORPORATION, Fukuoka (JP)

(72) Inventors: Yuuki Miyazaki, Fukuoka (JP); In Seob Park, Fukuoka (JP); Takuma Yasuda, Fukuoka (JP); Hyukgi Min, Fukuoka (JP)

(73) Assignees: SAMSUNG DISPLAY CO., LTD., Yongin-si (KR); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 1008 days.

(21) Appl. No.: 17/403,018

(22) Filed: Aug. 16, 2021

(65) Prior Publication Data
US 2022/0181556 A1    Jun. 9, 2022

(30) Foreign Application Priority Data

Dec. 8, 2020    (KR) .................. 10-2020-0170131

(51) Int. Cl.
*C07D 471/22*    (2006.01)
*C07D 498/22*    (2006.01)
(Continued)

(52) U.S. Cl.
CPC ......... *C07D 471/22* (2013.01); *C07D 498/22* (2013.01); *C09K 11/06* (2013.01);
(Continued)

(58) Field of Classification Search
CPC ............ H10K 85/657; H10K 85/6572; H10K 85/658; C07D 471/22; C07D 498/22;
(Continued)

(56) References Cited

U.S. PATENT DOCUMENTS 10,074,805 B2    9/2018    Tanabe et al.
10,256,414 B2    4/2019    Lim et al.
(Continued)

FOREIGN PATENT DOCUMENTS

CN    110790782        2/2020
CN    111574519 A  *  8/2020
(Continued)

OTHER PUBLICATIONS

CN-111574519-A—translation (Year: 2020).*
(Continued)

*Primary Examiner* — Jennifer A Boyd
*Assistant Examiner* — Rachel Simbana
(74) *Attorney, Agent, or Firm* — KILE PARK REED & HOUTTEMAN PLLC

(57) ABSTRACT

A light emitting device of an embodiment includes a first electrode, a second electrode facing the first electrode, and multiple organic layers disposed between the first electrode and the second electrode. At least one among the organic
(Continued)

layers includes a fused polycyclic compound represented by Formula 1 below, thereby showing improved emission efficiency.

[Formula 1]

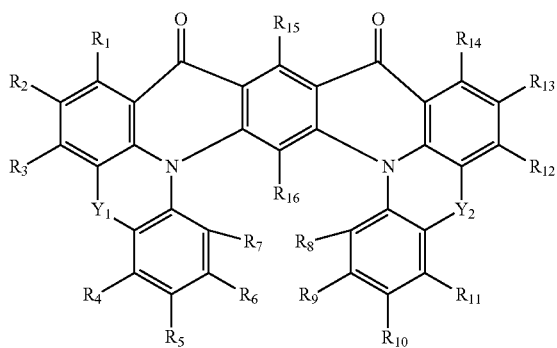

20 Claims, 7 Drawing Sheets

(51) Int. Cl.
C07D 513/22 (2006.01)
C09K 11/06 (2006.01)
H10K 50/11 (2023.01)
H10K 50/12 (2023.01)
H10K 50/15 (2023.01)
H10K 50/16 (2023.01)
H10K 50/17 (2023.01)
H10K 50/18 (2023.01)
H10K 85/60 (2023.01)
H10K 101/10 (2023.01)
H10K 101/20 (2023.01)

(52) U.S. Cl.
CPC ....... *H10K 85/657* (2023.02); *H10K 85/6572* (2023.02); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02); *H10K 50/18* (2023.02); *H10K 2101/10* (2023.02); *H10K 2101/20* (2023.02)

(58) Field of Classification Search
CPC .. C07D 413/00; C07D 413/02; C07D 413/04; C07D 413/14; C07D 513/22; C09K 2211/1018
See application file for complete search history.

(56) References Cited

U.S. PATENT DOCUMENTS

2020/0044159 A1 2/2020 Yamatani
2020/0144503 A1 5/2020 Hayano

FOREIGN PATENT DOCUMENTS

| JP | 2013-12535 | 1/2013 |
| KR | 10-2015-0066616 | 6/2015 |
| KR | 10-2020-0014451 | 2/2020 |
| KR | 10-2020-0052513 | 5/2020 |
| KR | 10-2021-0121350 | 10/2021 |
| WO | 2016/046034 | 3/2016 |

OTHER PUBLICATIONS

Min et al. (Min H.; Park, I.S.; Yasuda T.; 2021, cis-Quinacridone-Based Delayed Fluorescence Emitters: Seemingly Old but Renewed Functional Luminogens, Angew. Chem. Int. Ed. 2021, 60, 7643-7648 (Year: 2021).*

Jingping Zhang et al., "The ground state spin multiplicity of Schlenk-type biradicals and the influence of additional linkage to ladder type structures", Chemical Physics, 1996, pp. 339-351, vol. 206.

* cited by examiner

LIGHT EMITTING DEVICE AND FUSED POLYCYCLIC COMPOUND FOR LIGHT EMITTING DEVICE

CROSS-REFERENCE TO RELATED APPLICATION(S)

This application claims priority to and benefits of Korean Patent Application No. 10-2020-0170131 under 35 U.S.C. § 119, filed on Dec. 8, 2020 in the Korean Intellectual Property Office, the entire contents of which are incorporated herein by reference.

BACKGROUND

1. Technical Field

The disclosure relates to a fused polycyclic compound as a light emitting material and a light emitting device including the same.

2. Description of the Related Art

Active development continues for an organic electroluminescence display as an image display. The organic electroluminescence display is different from a liquid crystal display, and it is a so-called self-luminescent display in which holes and electrons respectively injected from a first electrode and a second electrode recombine in an emission layer so that a light emitting material including an organic compound in the emission layer emits light to achieve display.

In the application of a light emitting device to an image display, there is a need for a light emitting device having a decreased driving voltage, an increased emission efficiency, and an increased service life, and continuous development is required for materials in a light emitting device which stably achieves such characteristic . . . .

In order to attain high efficiency in an organic electroluminescence device, techniques on phosphorescence emission which uses energy in a triplet state or delayed fluorescence emission which uses the generating phenomenon of singlet excitons by the collision of triplet excitons (triplet-triplet annihilation, TTA) are being developed, and thus development continues on a material for thermally activated delayed fluorescence (TADF) using delayed fluorescence phenomenon.

It is to be understood that this background of the technology section is, in part, intended to provide useful background for understanding the technology. However, this background of the technology section may also include ideas, concepts, or recognitions that were not part of what was known or appreciated by those skilled in the pertinent art prior to a corresponding effective filing date of the subject matter disclosed herein.

SUMMARY

The disclosure provides a light emitting device showing improved emission efficiency.

The disclosure also provides a fused polycyclic compound which is capable of improving the emission efficiency of a light emitting device.

An embodiment provides a light emitting device which may include a first electrode, a second electrode facing the first electrode, and organic layers disposed between the first electrode and the second electrode. At least one organic layer among the organic layers may include a fused polycyclic compound, and the fused polycyclic compound may be represented by Formula 1 below.

[Formula 1]

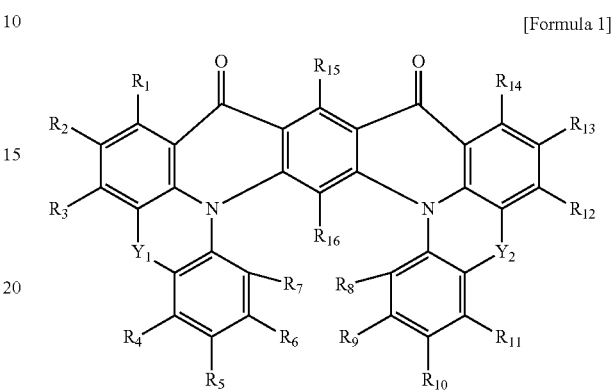

In Formula 1, $Y_1$ and $Y_2$ may each independently be a direct linkage, —O—, —S—, —(C=O)—, or —C($R_{17}$)($R_{18}$)—, and $R_1$ to $R_{18}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms.

In an embodiment, the organic layers may include a hole transport region disposed on the first electrode, an emission layer disposed on the hole transport region, and an electron transport region disposed on the emission layer. The emission layer may include the fused polycyclic compound.

In an embodiment, the emission layer may emit delayed fluorescence.

In an embodiment, the emission layer may be a delayed fluorescence emission layer including a host and a dopant, and the dopant may include the fused polycyclic compound.

In an embodiment, the emission layer may emit light having a central wavelength in a range of about 430 nm to about 530 nm.

In an embodiment, in Formula 1, $Y_1$ and $Y_2$ may be the same.

In an embodiment, in Formula 1, $R_1$ and $R_{14}$ may be the same, $R_2$ and $R_{13}$ may be the same, $R_3$ and $R_{12}$ may be the same, $R_4$ and $R_{11}$ may be the same, $R_5$ and $R_{10}$ may be the same, $R_6$ and $R_9$ may be the same, and $R_7$ and $R_8$ may be the same.

In an embodiment, the fused polycyclic compound represented by Formula 1 may be represented by any one among Formula 2-1 to Formula 2-5 below.

[Formula 2-1]

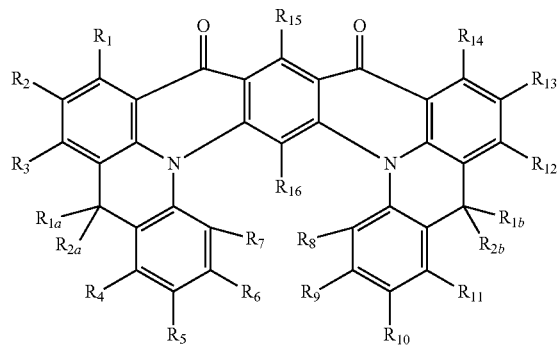

[Formula 2-2]

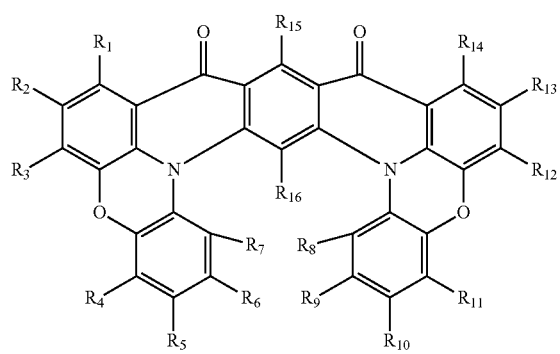

[Formula 2-3]

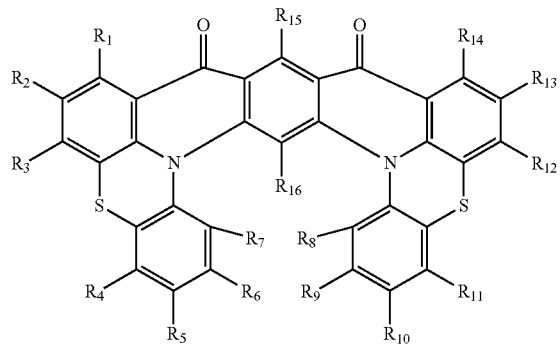

[Formula 2-4]

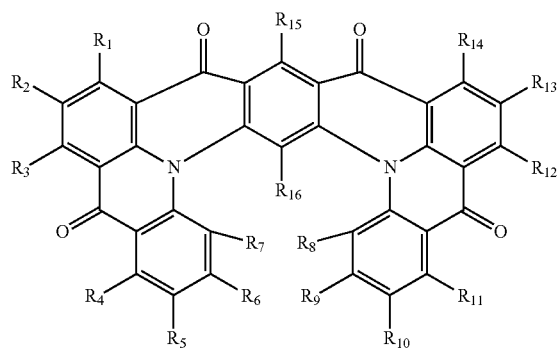

[Formula 2-5]

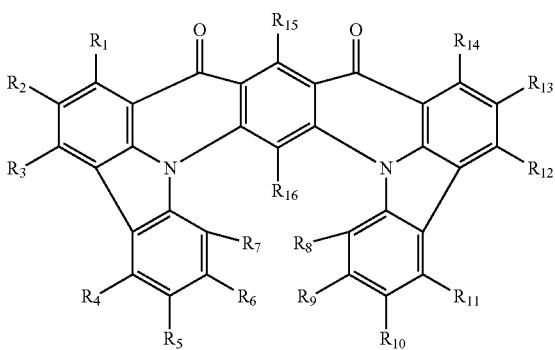

In Formula 2-1 to Formula 2-5, $R_{1a}$, $R_{1b}$, $R_{2a}$, and $R_{2b}$ may each independently be a hydrogen atom, a deuterium atom, a halogen atom, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms.

In Formula 2-1 to Formula 2-5, $R_1$ to $R_{16}$ may be the same as defined in connection with Formula 1.

In an embodiment, the fused polycyclic compound represented by Formula 1 may be represented by any one among Formula 3-1 to Formula 3-13 below.

[Formula 3-1]

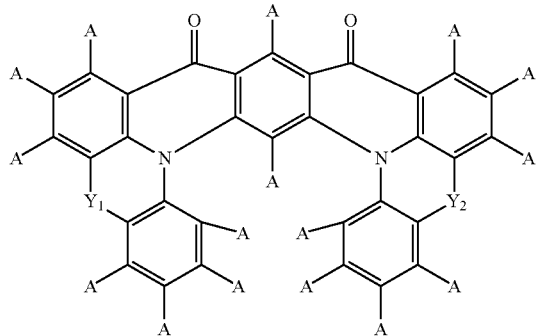

[Formula 3-2]

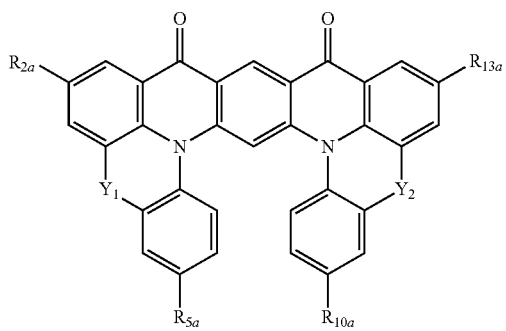

[Formula 3-3]
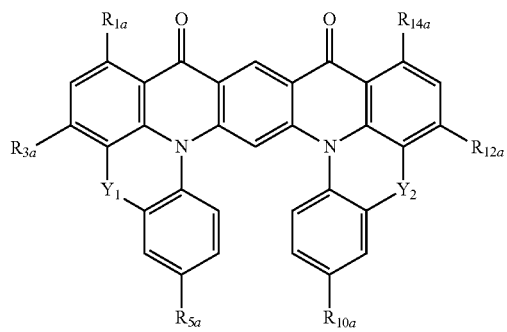
[Formula 3-4]
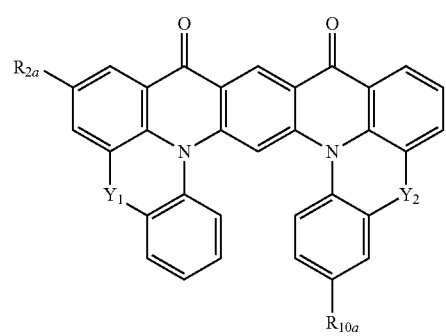
[Formula 3-5]
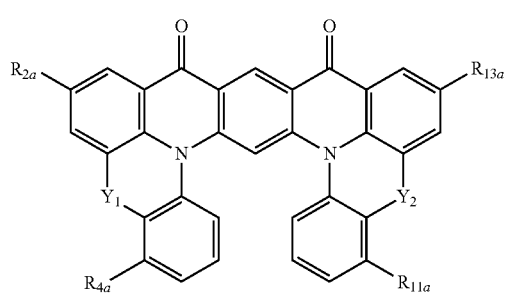
[Formula 3-6]
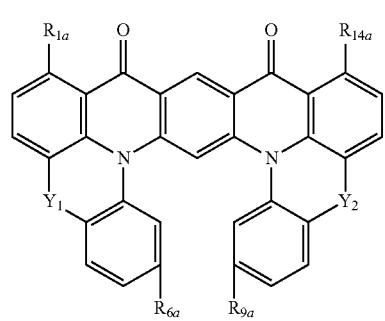
[Formula 3-7]
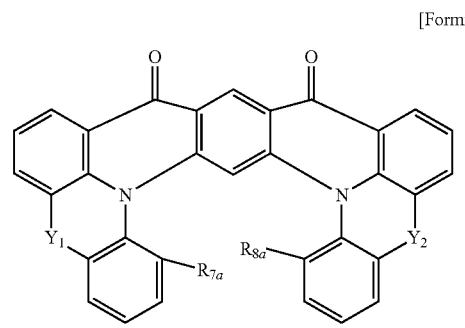
[Formula 3-8]
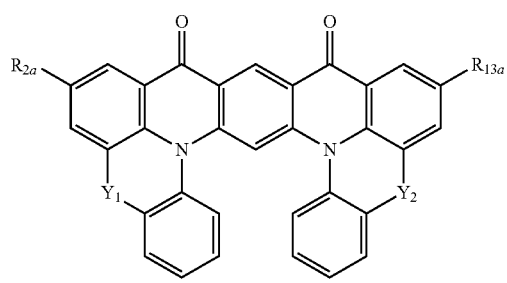
[Formula 3-9]
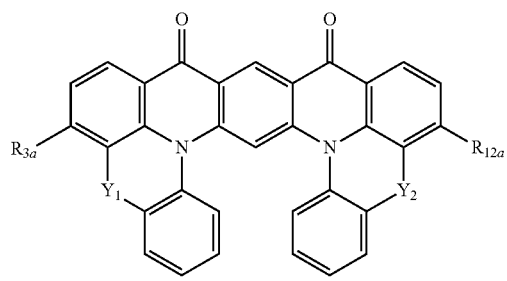
[Formula 3-10]
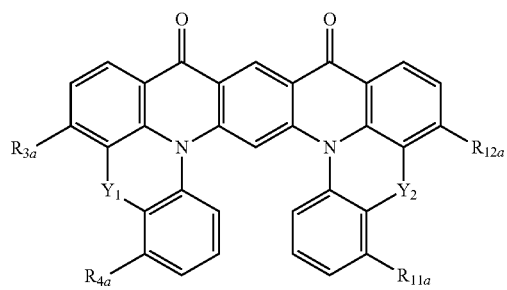
[Formula 3-11]
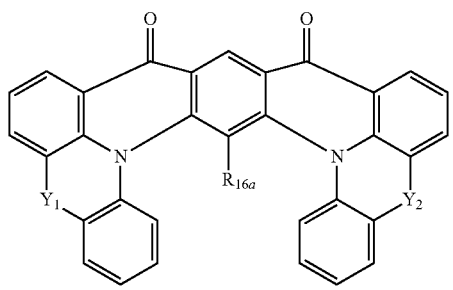
[Formula 3-12]
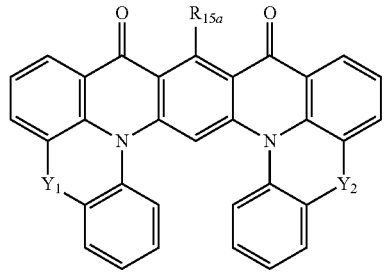

[Formula 3-13]

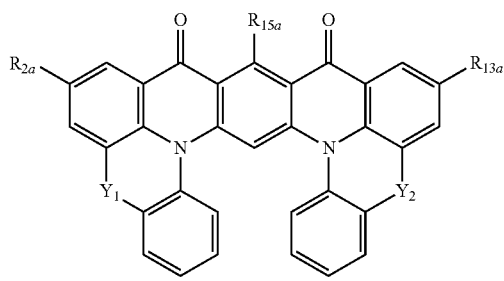

In Formula 3-1 to Formula 3-13, A may each independently be a hydrogen atom or a deuterium atom, and $R_{1a}$ to $R_{16a}$ may each independently be a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms.

In Formula 3-1 to Formula 3-13, $Y_1$, $Y_2$, $R_{17}$, and $R_{18}$ may be the same as defined in connection with Formula 1.

In an embodiment, in Formula 1, $R_1$ to $R_{18}$ may each independently be a hydrogen atom, a deuterium atom, a substituted or unsubstituted amine group, a substituted or unsubstituted methyl group, a substituted or unsubstituted t-butyl group, a substituted or unsubstituted octyl group, a substituted or unsubstituted cyclohexyl group, a substituted or unsubstituted adamantyl group, a substituted or unsubstituted phenyl group, a substituted or unsubstituted naphthyl group, a substituted or unsubstituted anthracene group, or a substituted or unsubstituted fluorenyl group.

In an embodiment, the light emitting device may further include a capping layer disposed on the second electrode, and the capping layer may have a refractive index greater than or equal to about 1.6.

An embodiment provides a light emitting device which may include a first electrode, a second electrode facing the first electrode, and an emission layer disposed between the first electrode and the second electrode. The emission layer may include a host and a delayed fluorescence dopant, and the delayed fluorescence dopant includes a fused polycyclic compound represented by Formula 1.

In an embodiment, the host may include a compound represented by Formula E-2a or Formula E-2b below.

[Formula E-2a]

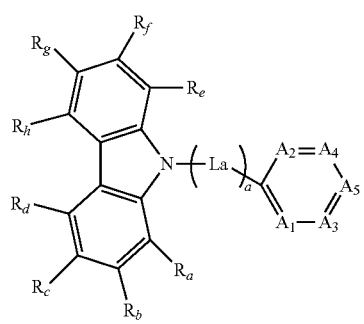

[Formula E-2b]

$(Cbz1)_a\text{-}(L_b)_b\text{-}(Cbz2)$

In Formula E-2a, a may be an integer from 0 to 10, $L_a$ may be a direct linkage, a substituted or unsubstituted arylene group of 6 to 30 ring-forming carbon atoms, or a substituted or unsubstituted heteroarylene group of 2 to 30 ring-forming carbon atoms, $A_1$ to $A_5$ may each independently be N or $C(R_i)$, and $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted phosphine oxide group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula E-2a, two or three of $A_1$ to $A_5$ may be N, and the remainder of $A_1$ to $A_5$ may be $C(R_i)$. In Formula E-2b, Cbz1 and Cbz2 may each independently be an unsubstituted carbazole group, or a carbazole group substituted with an aryl group of 6 to 30 ring-forming carbon atoms, $L_b$ may be a direct linkage, a substituted or unsubstituted arylene group of 6 to 30 ring-forming carbon atoms, or a substituted or unsubstituted heteroarylene group of 2 to 30 ring-forming carbon atoms, and b may be an integer from 0 to 10.

A fused polycyclic compound according to an embodiment may be represented by Formula 1 above.

BRIEF DESCRIPTION OF THE DRAWINGS

The accompanying drawings are included to provide a further understanding of the embodiments, and are incorporated in and constitute a part of this specification. The drawings illustrate embodiments of the disclosure and principles thereof. The above and other aspects and features of the disclosure will become more apparent by describing in detail embodiments thereof with reference to the attached drawings, in which.

DETAILED DESCRIPTION OF THE EMBODIMENTS

Figure 1:
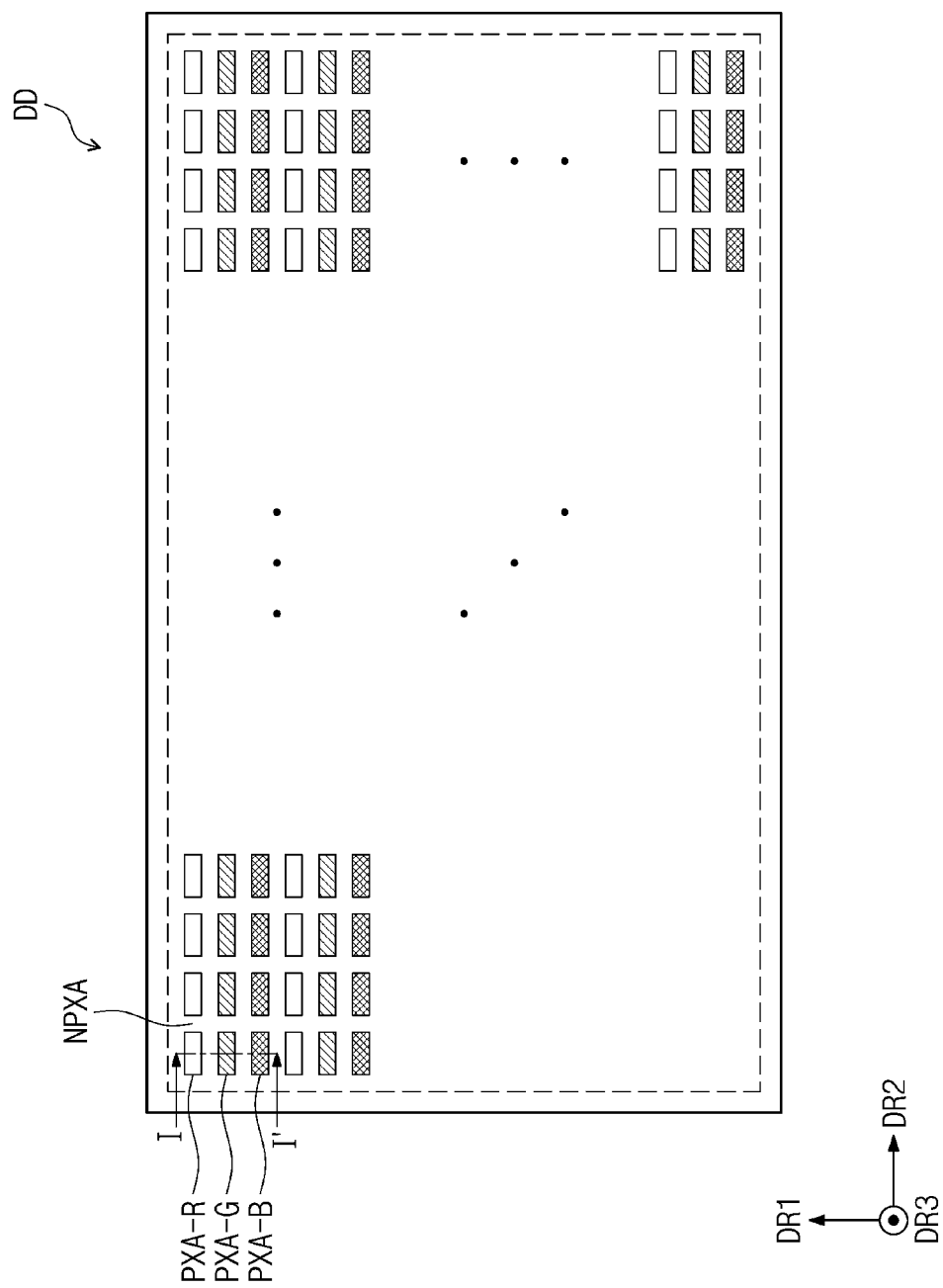
FIG. 1 is a plan view of a display apparatus according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

In the drawings, the sizes, thicknesses, ratios, and dimensions of the elements may be exaggerated for ease of description and for clarity. Like numbers refer to like elements throughout.

In the description, it will be understood that when an element (or region, layer, part, etc.) is referred to as being "on", "connected to", or "coupled to" another element, it can be directly on, connected to, or coupled to the other element, or one or more intervening elements may be present therebetween. In a similar sense, when an element (or region, layer, part, etc.) is described as "covering" another element, it can directly cover the other element, or one or more intervening elements may be present therebetween.

In the description, when an element is "directly on," "directly connected to," or "directly coupled to" another element, there are no intervening elements present. For example, "directly on" may mean that two layers or two elements are disposed without an additional element such as an adhesion element therebetween.

As used herein, the expressions used in the singular such as "a," "an," and "the," are intended to include the plural forms as well, unless the context clearly indicates otherwise.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or".

The term "at least one of" is intended to include the meaning of "at least one selected from" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms first, second, etc. may be used herein to describe various elements, these elements should not be limited by these terms. These terms are only used to distinguish one element from another element. Thus, a first element could be termed a second element without departing from the teachings of the disclosure. Similarly, a second element could be termed a first element, without departing from the scope of the disclosure.

The spatially relative terms "below", "beneath", "lower", "above", "upper", or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the illustrative term "below" may include both the lower and upper positions. The device may also be oriented in other directions and thus the spatially relative terms may be interpreted differently depending on the orientations.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within +20%, 10%, or 5% of the stated value.

It should be understood that the terms "comprises," "comprising," "includes," "including," "have," "having," "contains," "containing," and the like are intended to specify the presence of stated features, integers, steps, operations, elements, components, or combinations thereof in the disclosure, but do not preclude the presence or addition of one or more other features, integers, steps, operations, elements, components, or combinations thereof.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

In the description, the term "substituted or unsubstituted" may mean substituted or unsubstituted with at least one substituent selected from the group consisting of a deuterium atom, a halogen atom, a cyano group, a nitro group, an amine group, a silyl group, an oxy group, a thio group, a sulfinyl group, a sulfonyl group, a carbonyl group, a boron group, a phosphine group, a phosphine oxide group, a phosphine sulfide group, an alkyl group, an alkenyl group, an alkynyl group, an alkoxy group, a hydrocarbon ring group, an aryl group, and a heterocyclic group. Each of the substituents listed above may themselves be substituted or unsubstituted. For example, a biphenyl group may be interpreted as an aryl group or a phenyl group substituted with a phenyl group.

In the description, the term "forming a ring via the combination with an adjacent group" may mean forming a substituted or unsubstituted hydrocarbon ring, or a substituted or unsubstituted heterocycle via the combination with an adjacent group. The hydrocarbon ring may be an aliphatic hydrocarbon ring or an aromatic hydrocarbon ring. The heterocycle may be an aliphatic heterocycle or an aromatic heterocycle. The hydrocarbon ring and the heterocycle may each be monocyclic or polycyclic. A ring formed via combination with an adjacent group may be combined with another ring to form a spiro structure.

In the description, the term "adjacent group" may mean a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other. For example, in 1,13-dimethylquinolino[3,2,1-de]acridine-5,9-dione, two methyl groups connected with carbon at position 1 and carbon at position 13, respectively, may be interpreted as "adjacent groups" to each other.

In the description, examples of the halogen atom may include a fluorine atom, a chlorine atom, a bromine atom, and an iodine atom.

In the description, the alkyl group may be a linear, a branched, or a cyclic type. The number of carbon atoms in the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the hydrocarbon ring group may be an optional functional group or substituent derived from an aliphatic hydrocarbon ring. For example, the hydrocarbon ring group may be a saturated hydrocarbon ring group having 5 to 30 or 5 to 20 ring-forming carbon atoms.

In the description, the aryl group may be a functional group or substituent derived from an aromatic hydrocarbon ring. The aryl group may be a monocyclic aryl group or a polycyclic aryl group. The number of ring-forming carbon atome in the aryl group may be 6 to 60, 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc., without limitation.

In the description, the fluorenyl group may be substituted, and two substituents may be combined with each other to form a spiro structure. Examples of substituted fluorenyl groups are shown below, but embodiments are not limited thereto.

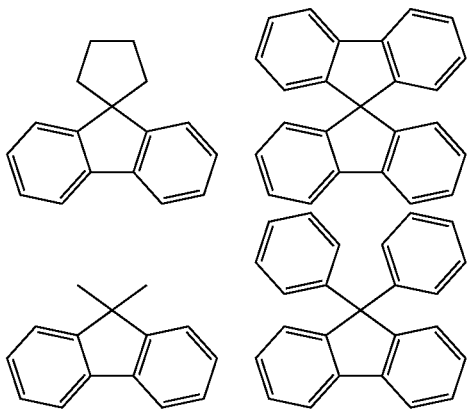

In the description, the heterocyclic group may be a functional group or substituent derived from a ring including at least one of B, O, N, P, Si, and S as heteroatoms. The heterocyclic group may include an aliphatic heterocyclic group and an aromatic heterocyclic group. The aromatic heterocyclic group may be a heteroaryl group. The aliphatic heterocyclic group and the aromatic heterocyclic group may be monocyclic or polycyclic.

In the description, the heterocyclic group may include at least one of B, O, N, P, Si, and S as heteroatoms. If the heterocyclic group includes two or more heteroatoms, the two or more heteroatoms may be the same as or different from each other. The heterocyclic group may be a monocyclic heterocyclic group or a polycyclic heterocyclic group, and this term may also include a heteroaryl group. The number of ring-forming carbon atoms in the heterocyclic group may be 2 to 60, 2 to 30, 2 to 20, and 2 to 10.

In the description, the aliphatic heterocyclic group may include at least one of B, O, N, P, Si, and S as heteroatoms. The number of ring-forming carbon atoms in the aliphatic heterocyclic group may be 2 to 60, 2 to 30, 2 to 20, or 2 to 10. Examples of the aliphatic heterocyclic group may include an oxirane group, a thiirane group, a pyrrolidine group, a piperidine group, a tetrahydrofuran group, a tetrahydrothiophene group, a thiane group, a tetrahydropyran group, a 1,4-dioxane group, etc., without limitation.

In the description, the heteroaryl group may include at least one of B, O, N, P, Si, and S as heteroatoms. If the heteroaryl group includes two or more heteroatoms, the two or more heteroatoms may be the same as or different from each other. The heteroaryl group may be a monocyclic heterocyclic group or a polycyclic heterocyclic group. The number of ring-forming carbon atoms in the heteroaryl group may be 2 to 60, 2 to 30, 2 to 20, or 2 to 10. Examples of the heteroaryl group may include thiophene, furan, pyrrole, imidazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofurane, phenanthroline, thiazole, isooxazole, oxazole, oxadiazole, thiadiazole, phenothiazine, dibenzosilole, dibenzofuran, etc., without limitation.

In the description, the explanation with respect to the aryl group may be applied to an arylene group except that the arylene group is a divalent group. The explanation with respect to the heteroaryl group may be applied to a heteroarylene group except that the heteroarylene group is a divalent group.

In the description, the alkenyl group may be a linear chain or a branched chain. The number of carbon atoms in the alkenyl group is not specifically limited but may be 2 to 30, 2 to 20, or 2 to 10. Examples of the alkenyl group may include a vinyl group, a 1-butenyl group, a 1-pentenyl group, a 1,3-butadienyl aryl group, a styrenyl group, a styrylvinyl group, etc., without limitation.

In the description, the number of carbon atoms in the alkynyl group is not specifically limited, but may be 2 to 30, 2 to 20 or 2 to 10. Examples of the alkynyl group may include a vinyl group, a 2-butynyl group, a 2-pentynyl group, and a 1,3-pentadinyl aryl group, without limitation.

In the description, the explanation with respect to the alkyl group, the alkenyl group, the alkynyl group, the aryl group, and the heteroaryl group may be applied to an alkyl connecting group, an alkenyl connecting group, an aryl connecting group, and a heteroaryl connecting group, respectively, except that these are divalent, trivalent, or tetravalent groups.

In the description, the silyl group may include an alkyl silyl group and an aryl silyl group. Examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc., without limitation.

In the description, the number of carbon atoms in a carbonyl group is not specifically limited, but may be 1 to 40, 1 to 30, or 1 to 20. For example, the carbonyl group may have the structures below, but is not limited thereto.

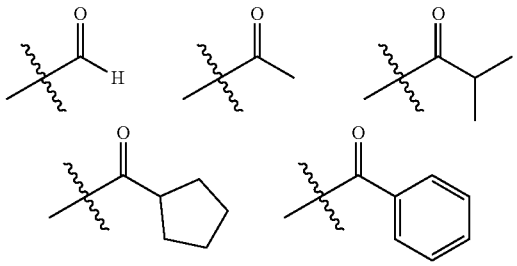

In the description, the number of carbon atoms in a sulfinyl group and a sulfonyl group is not specifically limited, but may be 1 to 30. The sulfinyl group may include an alkyl sulfinyl group and an aryl sulfinyl group. The sulfonyl group may include an alkyl sulfonyl group and an aryl sulfonyl group.

In the description, the thio group may include an alkyl thio group and an aryl thio group. The thio group may be the above-defined alkyl group or aryl group combined with a sulfur atom. Examples of the thio group may include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, etc., without limitation.

In the description, the oxy group may include the above-defined alkyl group or aryl group which is combined with an oxygen atom. The oxy group may include an alkoxy group and an aryl oxy group. The alkoxy group may be a linear, a branched, or a cyclic chain. The number of carbon atoms in the alkoxy group is not specifically limited but may be, for example, 1 to 20 or 1 to 10. Examples of the oxy group may include methoxy, ethoxy, n-propoxy, isopropoxy, butoxy, pentyloxy, hexyloxy, octyloxy, nonyloxy, decyloxy, benzyloxy, etc. However, embodiments are not limited thereto.

In the description, the boron group may include the above-defined alkyl group or aryl group which is combined with a boron atom. The boron group may include an alkyl boron group and an aryl boron group. Examples of the boron group may include a trimethylboron group, a triethylboron group, a t-butyldimethylboron group, a triphenylboron group, a diphenylboron group, a phenylboron group, etc., without limitation.

In the description, the number of carbon atoms in the amine group is not specifically limited, but may be 1 to 30. The amine group may include an alkyl amine group and an aryl amine group. Examples of the amine group may include a methylamine group, a dimethylamine group, a phenylamine group, a diphenylamine group, a naphthylamine group, a 9-methyl-anthracenylamine group, a triphenylamine group, etc., without limitation.

In the description, an alkyl group included in the alkylthio group, the alkylsulfoxy group, the alkylaryl group, the alkylamino group, the alkylboron group, the alkyl silyl group, and the alkyl amine group may be the same as the examples of the above-described alkyl group.

In the description, the aryl group included in the aryloxy group, the arylthio group, the arylsulfoxy group, the aryl amino group, the arylboron group, and the aryl silyl group may be the same as the examples of the above-described aryl group.

In the description, a direct linkage may be a single bond.

In the description,

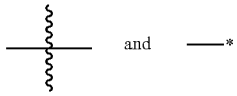

each represent a binding site to a neighboring atom.

Hereinafter, embodiments will be explained referring to the drawings.

Figure 2:
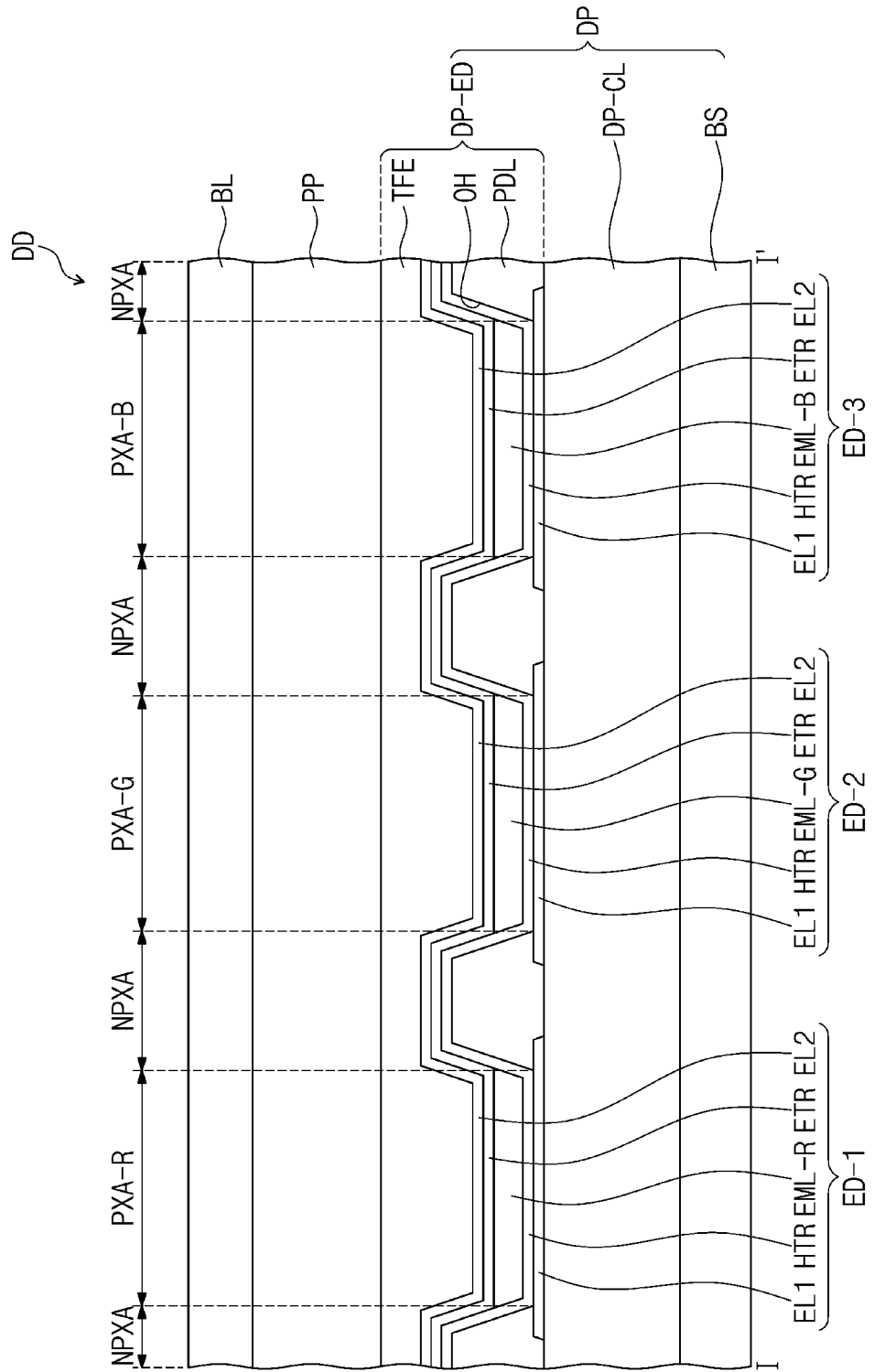
FIG. 2 is a schematic cross-sectional view of a display apparatus according to an embodiment.

FIG. 1 is a plan view showing an embodiment of a display apparatus DD. FIG. 2 is a schematic cross-sectional view of a display apparatus DD of an embodiment. FIG. 2 is a schematic cross-sectional view showing a part corresponding to line I-I'.

The display apparatus DD may include a display panel DP and an optical layer PP disposed on the display panel DP. The display panel DP includes light emitting devices ED-1, ED-2, and ED-3. The display apparatus DD may include multiple light emitting devices each of ED-1, ED-2, and ED-3. The optical layer PP may be disposed on the display panel DP and may control light reflected at the display panel DP from an external light. The optical layer PP may include, for example, a polarization layer or a color filter layer. Although not shown in the drawings, in an embodiment, the optical layer PP may be omitted from the display apparatus DD.

An upper base layer BL may be disposed on the optical layer PP. The upper base layer BL may be a member providing a base surface where the optical layer PP is disposed. The upper base layer BL may be a glass substrate, a metal substrate, a plastic substrate, etc. However, embodiments are not limited thereto, and the upper base layer BL may include an inorganic layer, an organic layer, or a composite material layer. Although not shown in the drawings, the upper base layer BL may be omitted in an embodiment.

The display apparatus DD according to an embodiment may further include a plugging layer (not shown). The plugging layer (not shown) may be disposed between a display device layer DP-ED and an upper base layer BL. The plugging layer (not shown) may be an organic layer. The plugging layer (not shown) may include at least one of an acrylic resin, a silicon-based resin, and an epoxy-based resin.

The display panel DP may include a base layer BS, a circuit layer DP-CL provided on the base layer BS, and a display device layer DP-ED. The display device layer DP-ED may include a pixel definition layer PDL, light emitting devices ED-1, ED-2, and ED-3 disposed in the pixel definition layer PDL, and an encapsulating layer TFE disposed on the light emitting devices ED-1, ED-2, and ED-3.

The base layer BS may be a member providing a base surface where the display device layer DP-ED is disposed. The base layer BS may be a glass substrate, a metal substrate, a plastic substrate, etc. However, embodiments are not limited thereto, and the base layer BS may include an inorganic layer, an organic layer, or a composite material layer.

In an embodiment, the circuit layer DP-CL is disposed on the base layer BS, and the circuit layer DP-CL may include multiple transistors (not shown). Each of the transistors (not shown) may include a control electrode, an input electrode, and an output electrode. For example, the circuit layer DP-CL may include switching transistors and driving transistors for driving the light emitting devices ED-1, ED-2, and ED-3 of the display device layer DP-ED.

Each of the light emitting devices ED-1, ED-2 and ED-3 may have the structures of light emitting devices ED of embodiments according to FIG. 3 to FIG. 6, which will be explained later. Each of the light emitting devices ED-1, ED-2, and ED-3 may include a first electrode EL1, a hole transport region HTR, emission layers EML-R, EML-G, and EML-B, an electron transport region ETR, and a second electrode EL2.

FIG. 2 illustrates an embodiment where the emission layers EML-R, EML-G, and EML-B of light emitting devices ED-1, ED-2, and ED-3 are disposed in opening portions OH defined in a pixel definition layer PDL, and a hole transport region HTR, an electron transport region ETR, and a second electrode EL2 are provided as common layers in all light emitting devices ED-1, ED-2, and ED-3. However, embodiments are not limited thereto. Although not shown in FIG. 2, in an embodiment, the hole transport region HTR and the electron transport region ETR may each be patterned and provided in the opening portions OH defined in the pixel definition layer PDL. For example, in an embodiment, the hole transport region HTR, the emission layers EML-R, EML-G, and EML-B, and the electron transport region ETR of the light emitting devices ED-1, ED-2 and ED-3 may be patterned by an ink jet printing method and provided.

An encapsulating layer TFE may cover the light emitting devices ED-1, ED-2, and ED-3. The encapsulating layer TFE may encapsulate the display device layer DP-ED. The encapsulating layer TFE may be a thin film encapsulating layer. The encapsulating layer TFE may be one layer or a stack of multiple layers. The encapsulating layer TFE maya include at least one insulating layer. The encapsulating layer TFE according to an embodiment may include at least one inorganic layer (hereinafter, encapsulating inorganic layer). The encapsulating layer TFE according to an embodiment may include at least one organic layer (hereinafter, encapsulating organic layer) and at least one encapsulating inorganic layer.

The encapsulating inorganic layer may protect the display device layer DP-ED from moisture and/or oxygen, and the encapsulating organic layer may protect the display device layer DP-ED from foreign materials such as dust particles. The encapsulating inorganic layer may include silicon nitride, silicon oxy nitride, silicon oxide, titanium oxide, or aluminum oxide, without specific limitation. The encapsulating organic layer may include an acrylic compound, an epoxy-based compound, etc. The encapsulating organic layer may include a photopolymerizable organic material, without specific limitation.

The encapsulating layer TFE may be disposed on the second electrode EL2 and may be disposed to fill the opening portion OH.

Referring to FIG. 1 and FIG. 2, the display apparatus DD may include a non-luminous area NPXA and luminous areas PXA-R, PXA-G, and PXA-B. The luminous areas PXA-R, PXA-G, and PXA-B may be areas emitting light produced from the light emitting devices ED-1, ED-2, and ED-3, respectively. The luminous areas PXA-R, PXA-G, and PXA-B may be separated from each other on a plane.

The luminous areas PXA-R, PXA-G, and PXA-B may be areas separated by the pixel definition layer PDL. The non-luminous areas NPXA may be areas between neighboring luminous areas PXA-R, PXA-G, and PXA-B and may be areas corresponding to the pixel definition layer PDL. In the disclosure, the luminous areas PXA-R, PXA-G, and PXA-B may each correspond to a pixel. The pixel definition layer PDL may separate the light emitting devices ED-1, ED-2, and ED-3. The emission layers EML-R, EML-G, and EML-B of the light emitting devices ED-1, ED-2, and ED-3 may be disposed and divided in the opening portions OH defined in the pixel definition layer PDL.

The luminous areas PXA-R, PXA-G, and PXA-B may be divided into multiple groups according to the color of light produced from the light emitting devices ED-1, ED-2, and ED-3. In the display apparatus DD of an embodiment, shown in FIG. 1 and FIG. 2, three luminous areas PXA-R, PXA-G, and PXA-B emitting red light, green light, and blue light, respectively, are illustrated as an embodiment. For example, the display apparatus DD of an embodiment may include a red luminous area PXA-R, a green luminous area PXA-G, and a blue luminous area PXA-B, which are separated from each other.

In the display apparatus DD according to an embodiment, light emitting devices ED-1, ED-2, and ED-3 may emit light having different wavelength regions. For example, in an embodiment, the display apparatus DD may include a first light emitting device ED-1 emitting red light, a second light emitting device ED-2 emitting green light, and a third light emitting device ED-3 emitting blue light. For example, each of the red luminous area PXA-R, the green luminous area PXA-G, and the blue luminous area PXA-B of the display apparatus DD may respectively correspond to the first light emitting device ED-1, the second light emitting device ED-2, and the third light emitting device ED-3.

However, embodiments are not limited thereto, and the first to third light emitting devices ED-1, ED-2, and ED-3 may emit light in a same wavelength region, or at least one thereof may emit light in a different wavelength region. For example, all the first to third light emitting devices ED-1, ED-2, and ED-3 may emit blue light.

The luminous areas PXA-R, PXA-G, and PXA-B in the display apparatus DD according to an embodiment may be arranged in a stripe configuration. Referring to FIG. 1, multiple red luminous areas PXA-R, multiple green luminous areas PXA-G and multiple blue luminous areas PXA-B may be arranged along a second directional axis DR2. The red luminous area PXA-R, the green luminous area PXA-G, and the blue luminous area PXA-B may be arranged by turns along a first directional axis DR1.

In FIG. 1 and FIG. 2, the luminous areas PXA-R, PXA-G, and PXA-B are each shown as having a similar area, but embodiments are not limited thereto. The areas of the luminous areas PXA-R, PXA-G, and PXA-B may be different from each other according to the wavelength region of light emitted. The areas of the luminous areas PXA-R, PXA-G, and PXA-B may be areas in a plan view that are defined by the first directional axis DR1 and the second directional axis DR2.

The arrangement type of the luminous areas PXA-R, PXA-G, and PXA-B is not limited to the configuration shown in FIG. 1, and the arrangement order of the red luminous areas PXA-R, the green luminous areas PXA-G, and the blue luminous areas PXA-B may be provided in various combinations according to the properties of display quality required for the display apparatus DD. For example, the arrangement type of the luminous areas PXA-R, PXA-G, and PXA-B may be a PenTile® arrangement type, or a diamond arrangement type.

The areas of the luminous areas PXA-R, PXA-G, and PXA-B may be different from each other. For example, in an embodiment, the area of the green luminous area PXA-G may be smaller than the area of the blue luminous area PXA-B, but embodiments are not limited thereto.

Hereinafter, FIG. 3 to FIG. 6 are each a schematic cross-sectional view showing light emitting devices according to embodiments. The light emitting device ED according to an embodiment may include a first electrode EL1, a hole transport region HTR, an emission layer EML, an electron transport region ETR, and a second electrode EL2, stacked in that order.

Figure 3:
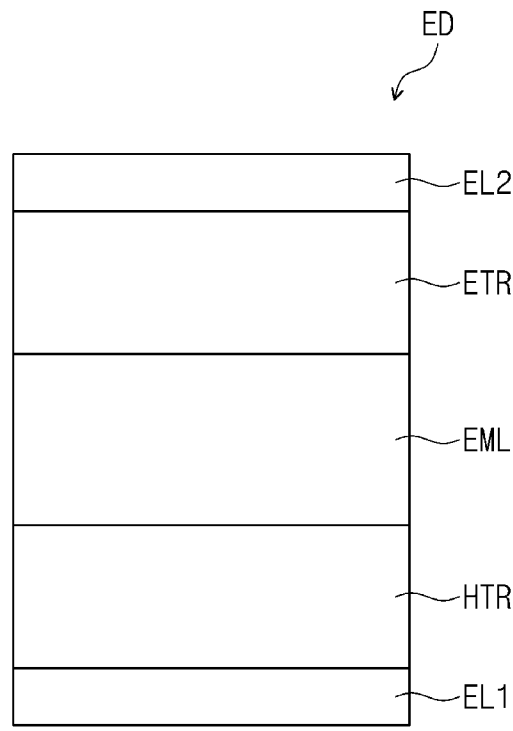
FIG. 3 is a schematic cross-sectional view showing a light emitting device according to an embodiment.
Figure 4:
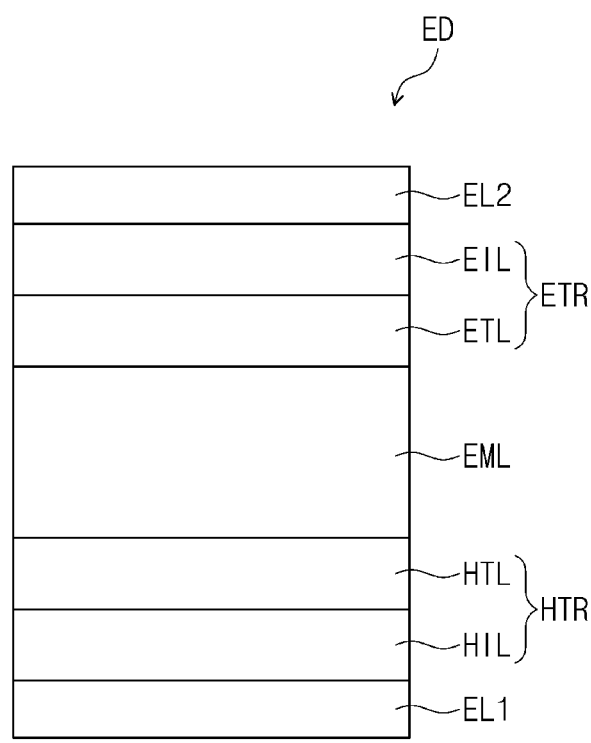
FIG. 4 is a schematic cross-sectional view showing a light emitting device according to an embodiment.
Figure 5:
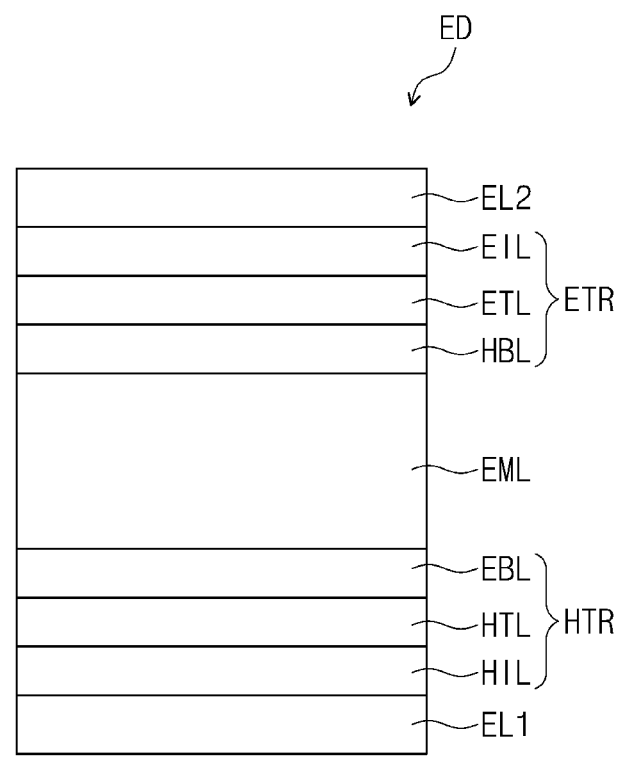
FIG. 5 is a schematic cross-sectional view showing a light emitting device according to an embodiment.
Figure 6:
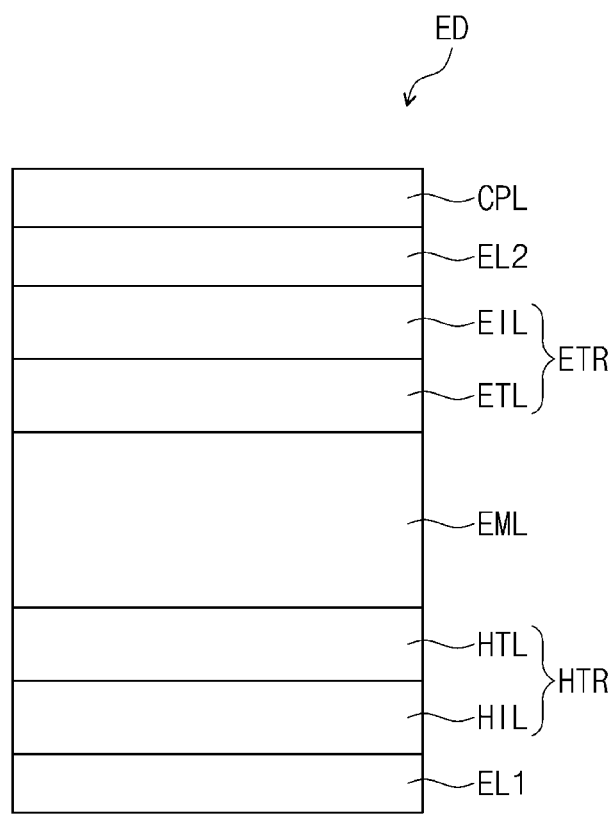
FIG. 6 is a schematic cross-sectional view showing a light emitting device according to an embodiment.

In comparison to FIG. 3, FIG. 4 shows a schematic cross-sectional view of a light emitting device ED of an embodiment, wherein a hole transport region HTR includes a hole injection layer HIL and a hole transport layer HTL, and an electron transport region ETR includes an electron injection layer EIL and an electron transport layer ETL. In comparison to FIG. 3, FIG. 5 shows a schematic cross-sectional view of a light emitting device ED of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. In comparison to FIG. 4, FIG. 6 shows a schematic cross-sectional view of a light emitting device ED of an embodiment, including a capping layer CPL disposed on the second electrode EL2.

The first electrode EL1 has conductivity. The first electrode EL1 may be formed using a metal material, a metal alloy, or a conductive compound. The first electrode EL1 may be an anode or a cathode. However, embodiments are not limited thereto. For example, in an embodiment, the first electrode EL1 may be a pixel electrode. The first electrode EL1 may be a transmissive electrode, a transflective electrode, or a reflective electrode. If the first electrode EL1 is a transmissive electrode, the first electrode EL1 may include a transparent metal oxide such as indium tin oxide (ITO), indium zinc oxide (IZO), zinc oxide (ZnO), and indium tin zinc oxide (ITZO). If the first electrode EL1 is a transflective electrode or a reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, W, In, Zn, Sn, compounds thereof, or mixtures thereof (for example, a mixture of Ag and Mg). The first electrode EL1 may have a structure including multiple layers including a reflective layer or a transflective layer formed using the above materials, and a transmissive conductive layer formed using ITO, IZO, ZnO, or ITZO. For example, the first electrode EL1 may include a three-layer structure of ITO/Ag/ITO. However, embodiments are not limited thereto. The first electrode EL1 may include the above-described metal materials, combinations of two or more metal materials selected from the above-described metal materials, or oxides of the above-described metal materials. A thickness of the first electrode EL1 may be in a range of about 700 Å to about 10,000 Å. For example, the thickness of the first electrode EL1 may be in a range of about 1,000 Å to about 3,000 Å.

The hole transport region HTR is provided on the first electrode EL1. The hole transport region HTR may include at least one of a hole injection layer HIL, a hole transport layer HTL, a buffer layer (not shown), an emission auxiliary layer (not shown), and an electron blocking layer EBL. A thickness of the hole transport region HTR may be in a range of about 50 Å to about 15,000 Å.

The hole transport region HTR may have a single layer formed using a single material, a single layer formed using different materials, or a multilayer structure including layers formed using different materials.

For example, the hole transport region HTR may have the structure of a single layer of a hole injection layer HIL or a hole transport layer HTL, and may have a structure of a single layer formed using a hole injection material and a hole transport material. In another embodiment, the hole transport region HTR may have a structure of a single layer formed using multiple different materials, or a structure stacked from the first electrode EL1 of a hole injection layer HIL/a hole transport layer HTL, a hole injection layer HIL/a hole transport layer HTL/a buffer layer (not shown), a hole injection layer HIL/a buffer layer (not shown), a hole transport layer HTL/a buffer layer (not shown), or a hole injection layer HIL/a hole transport layer HTL/a electron blocking layer EBL, without limitation.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole transport region HTR may include a compound represented by Formula H-1 below.

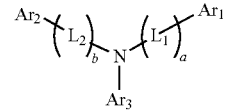

[Formula H-1]

In Formula H-1 above, $L_1$ and $L_2$ may each independently be a direct linkage, a substituted or unsubstituted arylene group of 6 to 30 ring-forming carbon atoms, or a substituted or unsubstituted heteroarylene group of 2 to 30 ring-forming carbon atoms. In Formula H-1, a and b may each independently be an integer from 0 to 10. In Formula H-1, if a or b is 2 or more, multiple $L_1$ groups and multiple $L_2$ groups may each independently be a substituted or unsubstituted arylene group of 6 to 30 ring-forming carbon atoms, or a substituted or unsubstituted heteroarylene group of 2 to 30 ring-forming carbon atoms.

In Formula H-1, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms. In Formula H-1, $Ar_3$ may be a substituted or unsubstituted aryl group of 6 to 30 ring-forming carbon atoms.

The compound represented by Formula H-1 may be a monoamine compound. In another embodiment, the compound represented by Formula H-1 may be a diamine compound in which at least one among $Ar_1$ to $Ar_3$ includes an amine group as a substituent. For example, the compound represented by Formula H-1 may be a carbazole-based compound in which at least one among $Ar_1$ to $Ar_3$ includes a substituted or unsubstituted carbazole group, or a fluorene-based compound in which at least one among $Ar_1$ to $Ar_3$ includes a substituted or unsubstituted fluorene group.

The compound represented by Formula H-1 may be any one selected from the compounds in Compound Group H below. However, the compounds shown in Compound Group H are only examples, and the compound represented by Formula H-1 is not limited to the compounds in Compound Group H below.

[Compound Group H]
H-1-1
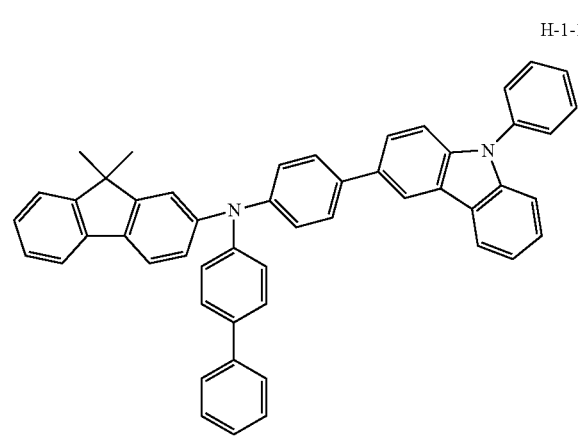
H-1-2
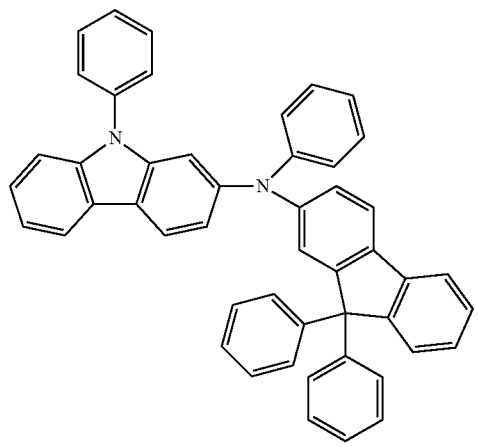
H-1-3
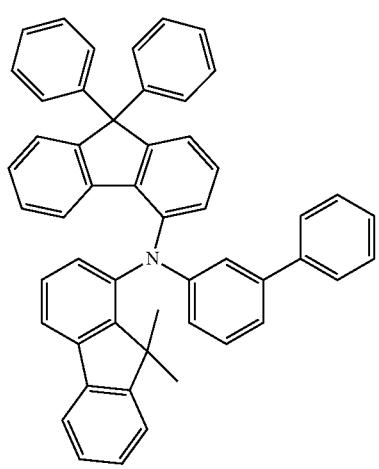
H-1-4
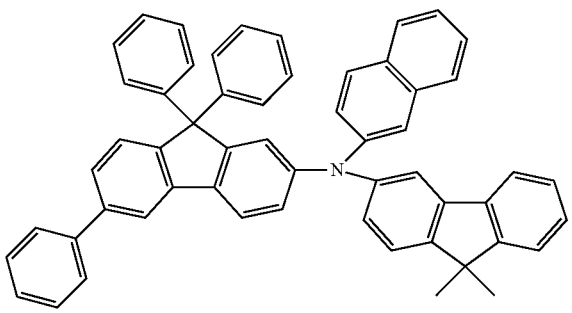
H-1-5
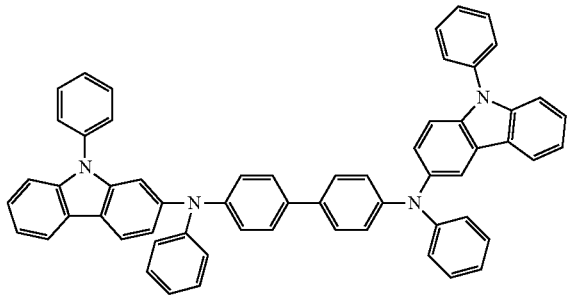
H-1-6
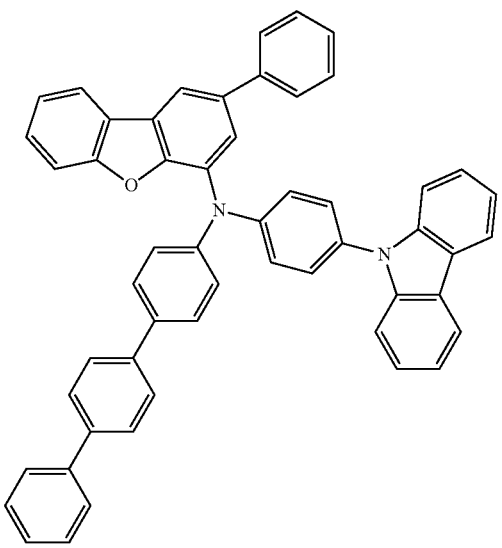

H-1-7
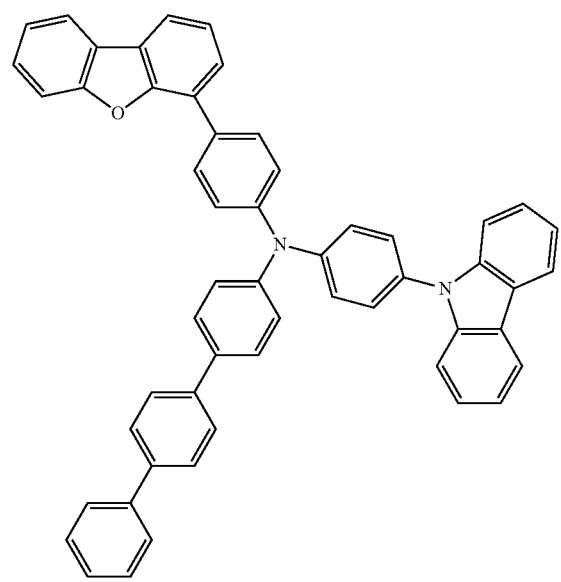
H-1-8
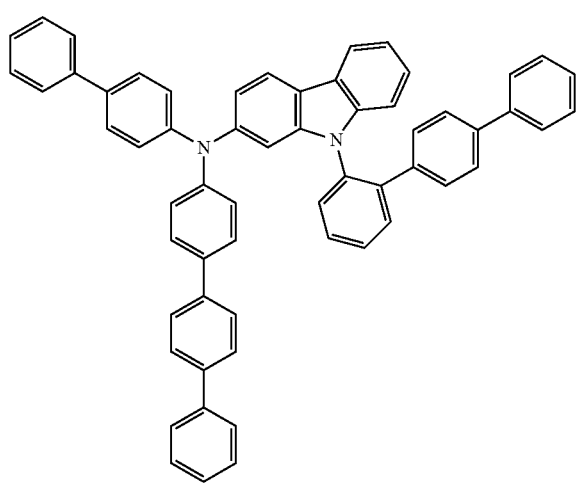
H-1-9
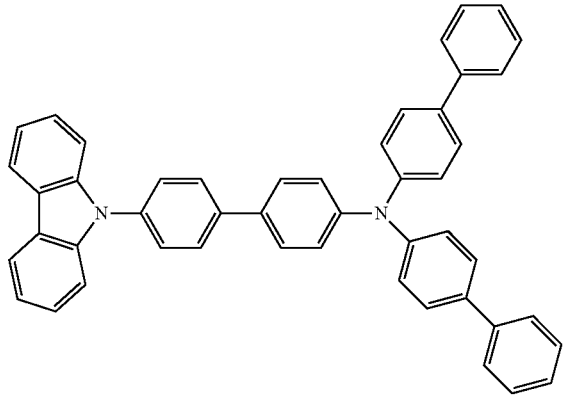
H-1-10
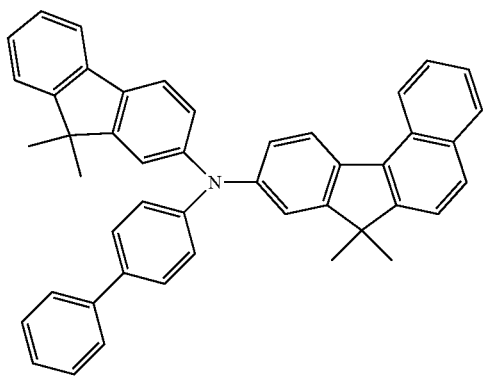
H-1-11
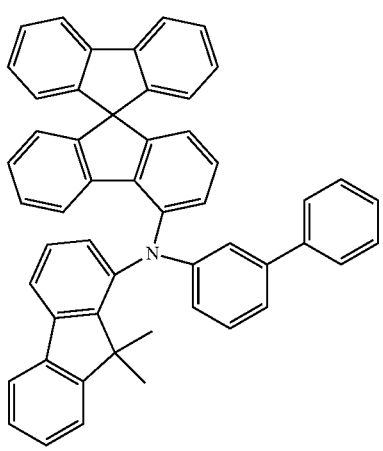
H-1-12
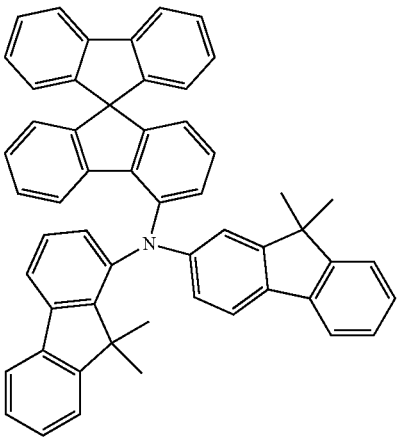
H-1-13
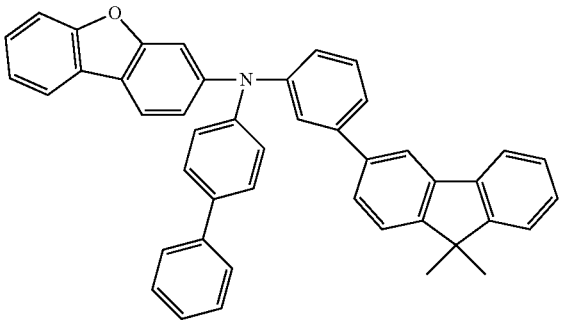

H-1-14
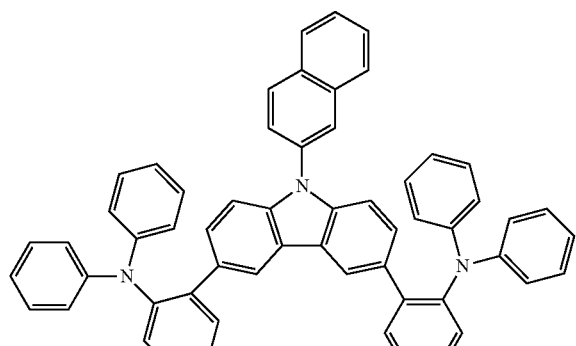
H-1-15
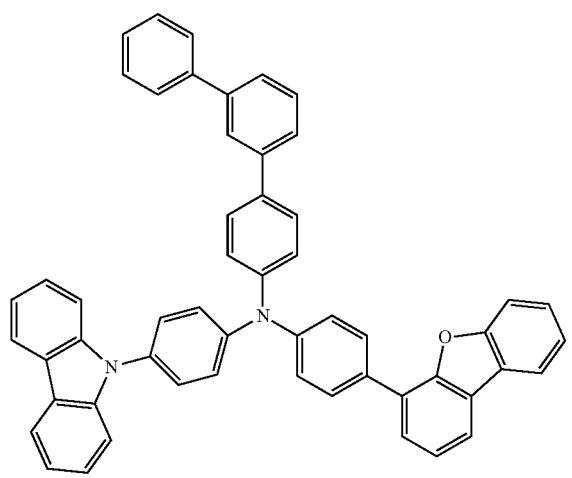
H-1-16
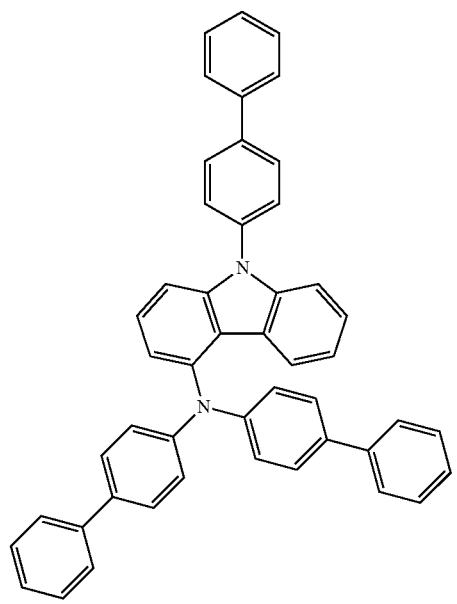
H-1-17
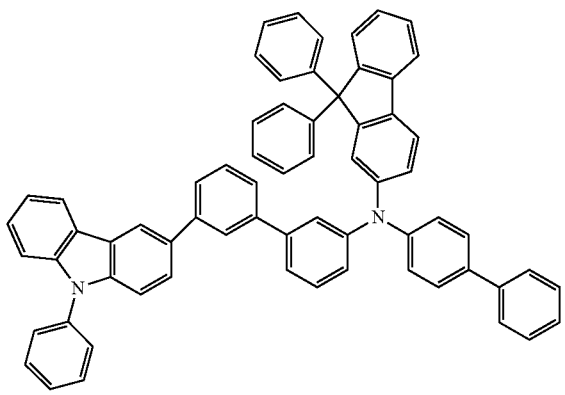
H-1-18
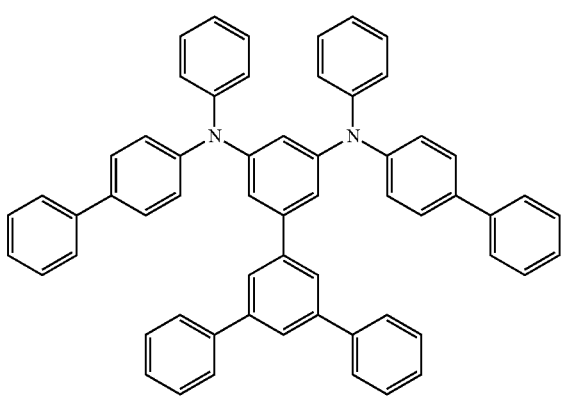
H-1-19
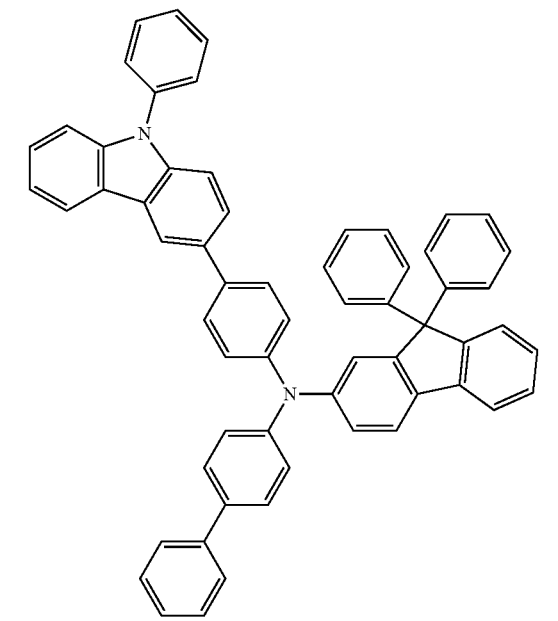
The hole transport region HTR may include a phthalocyanine compound such as copper phthalocyanine, $N^1,N^{1'}$-([1,1'-biphenyl]-4,4'-diyl)bis($N^1$-phenyl-$N^4,N^4$-di-m-tolyl-benzene-1,4-diamine) (DNTPD), 4,4',4"-[tris(3-methylphenyl)phenylamino]triphenylamine (m-MTDATA), 4,4',4"-tris(N,N-diphenylamino)triphenylamine (TDATA), 4,4',4"-tris[N(2-naphthyl)-N-phenylamino]-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB), triphenylamine-containing polyetherketone (TPAPEK), 4-isopropyl-4'-methyldiphenyliodonium [tetrakis(pentafluorophenyl) borate], and dipyrazino[2,3-f:2',3'-h]quinoxaline-2,3,6,7,10,11-hexacarbonitrile (HAT-CN).

The hole transport region HTR may include carbazole derivatives such as N-phenyl carbazole and polyvinyl carbazole, fluorene-based derivatives, N,N'-bis(3-methylphenyl)-N,N'-diphenyl-[1,1'-biphenyl]-4,4'-diamine (TPD), triphenylamine-based derivatives such as 4,4',4''-tris(N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzeneamine](TAPC), 4,4'-bis[N,N'-(3-tolyl)amino]-3,3'-dimethylbiphenyl (HMTPD), 1,3-bis(N-carbazolyl)benzene (mCP), etc.

The hole transport region HTR may include 9-(4-tert-butylphenyl)-3,6-bis(triphenylsilyl)-9H-carbazole (CzSi), 9-phenyl-9H-3,9'-bicarbazole (CCP), 1,3-bis(1,8-dimethyl-9H-carbazol-9-yl)benzene (mDCP), etc.

The hole transport region HTR may include the compounds of the hole transport region in at least one of the hole injection layer HIL, the hole transport layer HTL, and the electron blocking layer EBL.

A thickness of the hole transport region HTR may be in a range of about 100 Å to about 10,000 Å. For example, the thickness of the hole transport region HTR may be in a range of about 100 Å to about 5,000 Å. In case where the hole transport region HTR includes a hole injection layer HIL, a thickness of the hole injection region HIL may be, for example, in a range of about 30 Å to about 1,000 Å. In case where the hole transport region HTR includes a hole transport layer HTL, a thickness of the hole transport layer HTL may be in a range of about 30 Å to about 1,000 Å. For example, in case where the hole transport region HTR includes an electron blocking layer, a thickness of the electron blocking layer EBL may be in a range of about 10 Å to about 1,000 Å. If the thicknesses of the hole transport region HTR, the hole injection layer HIL, the hole transport layer HTL, and the electron blocking layer EBL satisfy the above-described ranges, satisfactory hole transport properties may be achieved without substantial increase of a driving voltage.

The hole transport region HTR may further include a charge generating material to increase conductivity in addition to the above-described materials. The charge generating material may be dispersed uniformly or non-uniformly in the hole transport region HTR. The charge generating material may be, for example, a p-dopant. The p-dopant may include at least one of metal halide compounds, quinone derivatives, metal oxides, and cyano group-containing compounds, without limitation. For example, the p-dopant may include metal halide compounds such as CuI and RbI, quinone derivatives such as tetracyanoquinodimethane (TCNQ) and 2,3,5,6-tetrafluoro-7,7',8,8-tetracyanoquinodimethane (F4-TCNQ), metal oxides such as tungsten oxide and molybdenum oxide, cyano group-containing compounds such as dipyrazino[2,3-f:2',3'-h]quinoxaline-2,3,6,7,10,11-hexacarbonitrile (HATCN) and 4-[[2,3-bis[cyano-(4-cyano-2,3,5,6-tetrafluorophenyl)methylidene]cyclopropylidene]-cyanomethyl]-2,3,5,6-tetrafluorobenzonitrile, etc., without limitation.

As described above, the hole transport region HTR may further include at least one of a buffer layer (not shown) and an electron blocking layer EBL in addition to the hole injection layer HIL and the hole transport layer HTL. The buffer layer (not shown) may compensate for a resonance distance according to the wavelength of light emitted from an emission layer EML and may increase emission efficiency. Materials which may be included in the hole transport region HTR may be used as materials included in the buffer layer (not shown). The electron blocking layer EBL may prevent the injection of electrons from the electron transport region ETR to the hole transport region HTR.

The emission layer EML is provided on the hole transport region HTR. The emission layer EML may have a thickness, for example, in a range of about 100 Å to about 1,000 Å. For example, the emission layer EML may have a thickness in a range of about 100 Å to about 300 Å. The emission layer EML may have a single layer formed using a single material, a single layer formed using different materials, or a multi-layer structure having layers formed using different materials.

In the light emitting device ED according to an embodiment, the emission layer EML may include a fused polycyclic compound of an embodiment.

The fused polycyclic compound of an embodiment may be a compound including an additional fused structure in a quinolinoacridinedione skeleton. The fused polycyclic compound of an embodiment may be a compound having an additional fused structure through an additional connecting group including a direct linkage, an oxy group, a thio group, a carbonyl group, an alkyl group, etc., on a quinolinoacridinedione skeleton.

The fused polycyclic compound of an embodiment may be represented by Formula 1 below.

[Formula 1]

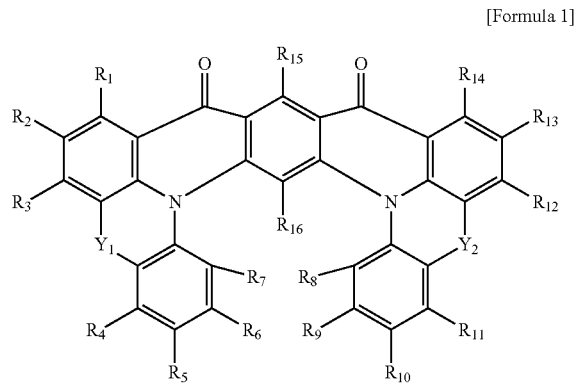

In Formula 1, $Y_1$ and $Y_2$ may each independently be a direct linkage, —O—, —S—, —(C=O)—, or —C($R_{17}$)($R_{18}$)—. The fused polycyclic compound represented by Formula 1 may be a compound having an additional fused structure at $Y_1$ and $Y_2$, i.e., an additional connecting group including a direct linkage, an oxy group, a thio group, a carbonyl group, an alkyl group, etc.

In Formula 1, $R_1$ to $R_{18}$ may each independently be a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms. In an embodiment, in Formula 1, $R_1$ to $R_{16}$ may each independently be a hydrogen atom, a deuterium atom, a substituted or unsubstituted amine group, a substituted or unsubstituted methyl group, a substituted or unsubstituted t-butyl group, a substituted or unsubstituted octyl group, a substituted or unsubstituted cyclohexyl group, a substituted or unsubstituted adamantyl group, a substituted or unsubstituted phenyl group, a substituted or unsubstituted naphthyl group, a substituted or unsubstituted anthracenyl group, or a substituted or unsubstituted fluorenyl group. For example, $R_{17}$ and $R_{18}$ may each independently be a hydrogen atom, a deuterium atom, a substituted or unsubstituted methyl group, a substituted or unsubstituted phenyl group, or a substituted or unsubstituted terphenyl group. In Formula 1, $R_1$ to $R_{18}$ may each independently be combined with an adjacent group to form a ring.

The fused polycyclic compound of an embodiment may have a structure represented by Formula 1. The fused polycyclic compound of an embodiment may have a structure in which an additional fused structure is formed on a quinolinoacridinedione skeleton through an additional connecting group including a direct linkage, an oxy group, a thio group, a carbonyl group, an alkyl group, etc. The fused polycyclic compound of an embodiment may include a structure in which an additional fused structure is formed on a quinolinoacridinedione skeleton, and forms a wide conjugation structure, thereby stabilizing a fused aromatic ring structure. Accordingly, a suitable wavelength region may be selected for a blue light emitting material, and if applied to a light emitting device, the efficiency of the light emitting device may be improved.

The fused polycyclic compound represented by Formula 1 may have a symmetric structure with an imaginary line connecting substituents $R_{15}$ and $R_{16}$ as a reference line.

When the fused polycyclic compound represented by Formula 1 has a symmetric structure, substituents present at symmetric positions with respect to a symmetry line may be the same.

For example, in Formula 1, $Y_1$ and $Y_2$ may be the same. For example, $Y_1$ and $Y_2$ may each be a direct linkage. For example, $Y_1$ and $Y_2$ may each be —O—. For example, $Y_1$ and $Y_2$ may each be —S—. For example, $Y_1$ and $Y_2$ may each be —(C=O)—. For example, $Y_1$ and $Y_2$ may each be —C($R_{17}$)($R_{18}$)—. For example, $R_{17}$ and $R_{18}$ included in $Y_1$ and $Y_2$, respectively, may be the same.

In an embodiment, in Formula 1, $R_1$ and $R_{14}$ may be the same, $R_2$ and $R_{13}$ may be the same, $R_3$ and $R_{12}$ may be the same, $R_4$ and $R_{11}$ may be the same, $R_5$ and $R_{10}$ may be the same, $R_6$ and $R_9$ may be the same, and $R_7$ and $R_8$ may be the same.

However, embodiments are not limited thereto, and Formula 1 may not have a symmetric structure but may have an asymmetric structure with respect to an imaginary line connecting substituents $R_{15}$ and $R_{16}$ as a reference line.

In an embodiment, the fused polycyclic compound represented by Formula 1 may be represented by any one among Formula 2-1 to Formula 2-5 below.

[Formula 2-1]
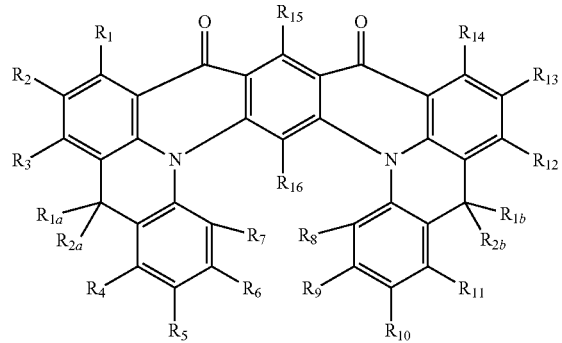

[Formula 2-2]
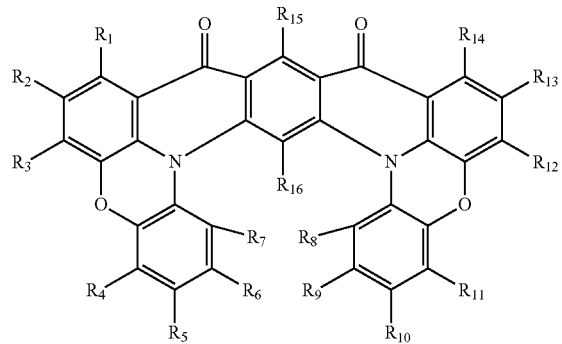

[Formula 2-3]
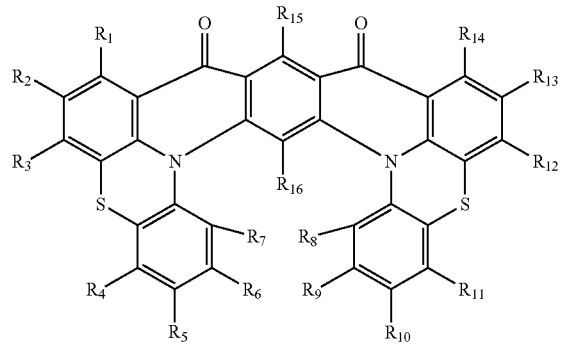

[Formula 2-4]
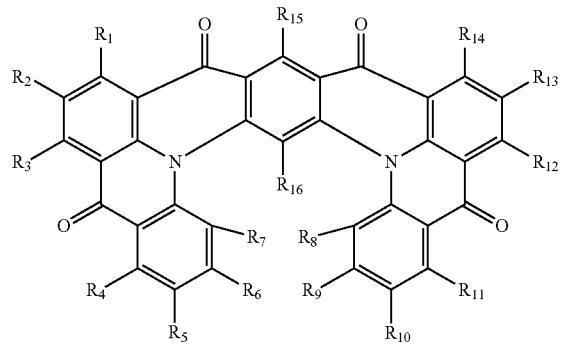

[Formula 2-5]

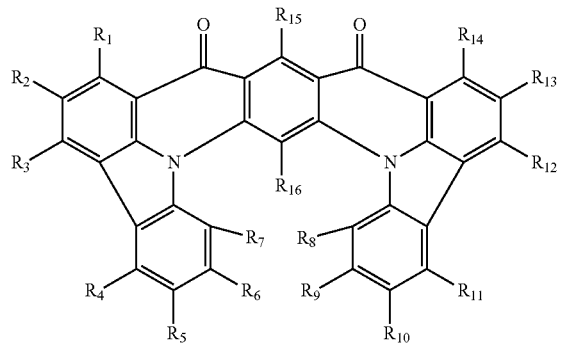

Formula 2-1 to Formula 2-5 represent cases of Formula 1 where $Y_1$ and $Y_2$ are specified. Formula 2-1 to Formula 2-5 represent cases of Formula 1 where $Y_1$ and $Y_2$ are specified as the same moiety.

In Formula 2-1 to Formula 2-5, $R_{1a}$, $R_{1b}$, $R_{2a}$, and $R_{2b}$ may each independently be a hydrogen atom, a deuterium atom, a halogen atom, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms. In Formula 2-1 to Formula 2-5, $R_1$ to $R_{16}$ may be the same as defined in connection with Formula 1.

In an embodiment, the fused polycyclic compound represented by Formula 1 may be represented by any one among Formula 3-1 to Formula 3-13 below.

[Formula 3-1]

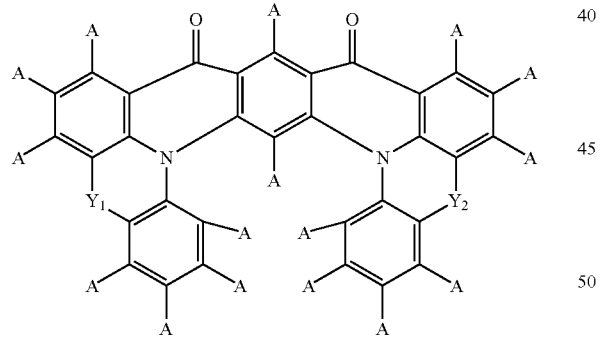

[Formula 3-2]

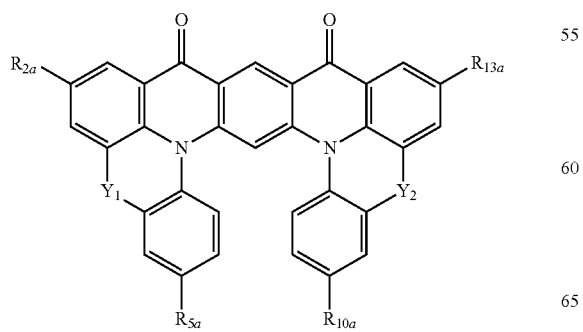

[Formula 3-3]

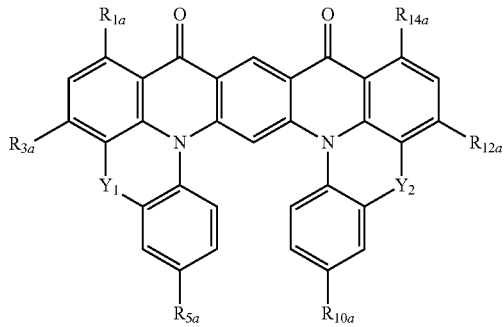

[Formula 3-4]

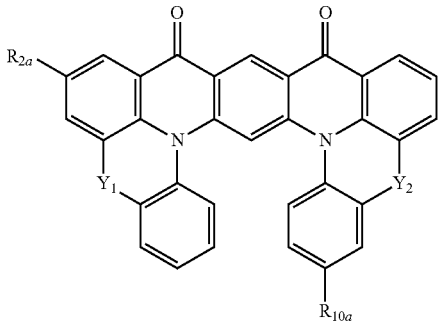

[Formula 3-5]

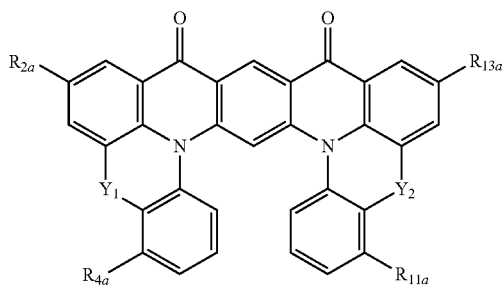

[Formula 3-6]

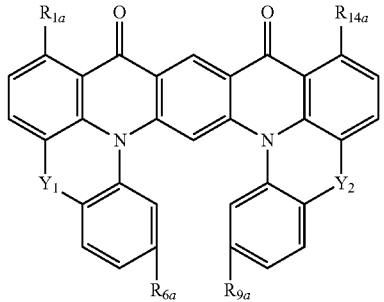

[Formula 3-7]

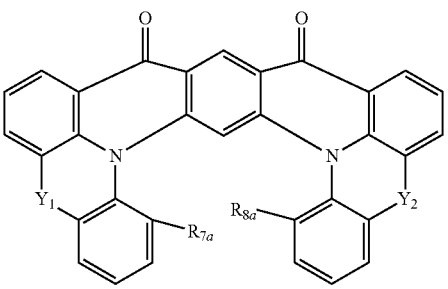

[Formula 3-8]

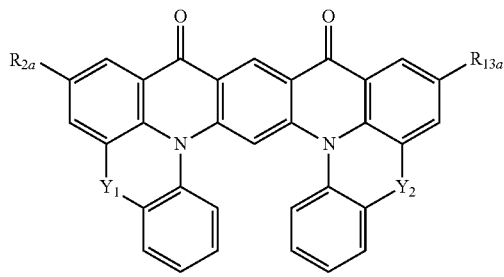

[Formula 3-9]

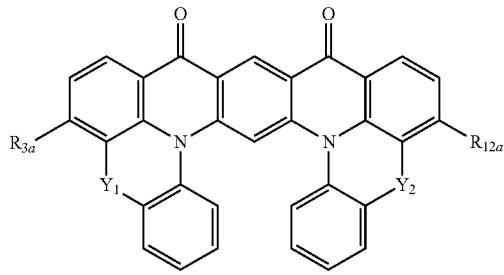

[Formula 3-10]

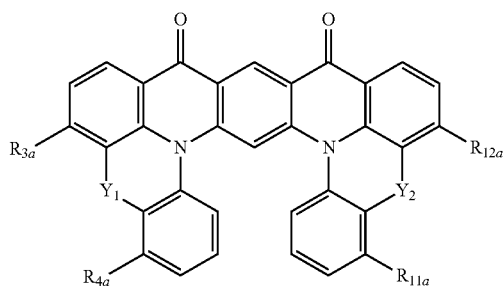

[Formula 3-11]

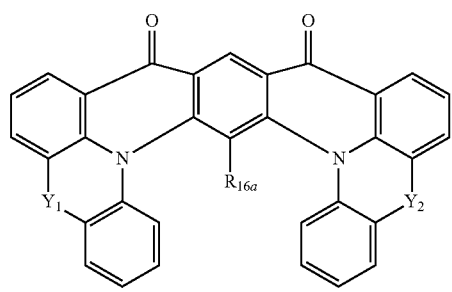

[Formula 3-12]

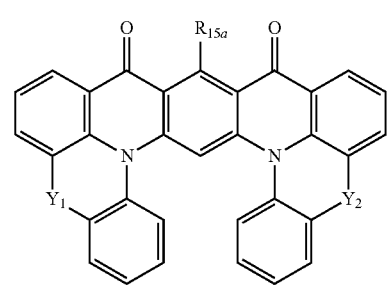

[Formula 3-13]

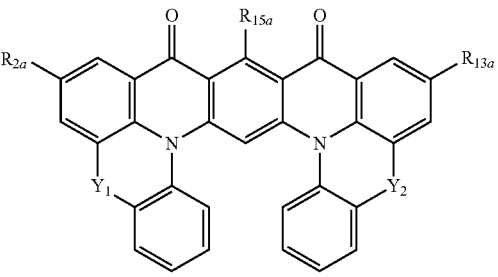

Formula 3-1 to Formula 3-13 represent cases of Formula 1 where the substituents represented by $R_1$ to $R_{16}$ are hydrogen atoms or deuterium atoms, or connected with other substituents.

In Formula 3-1, A may each independently be a hydrogen atom or a deuterium atom. In Formula 3-1, each of the positions of substituents represented by A may be the same and may all be hydrogen atoms or deuterium atoms, or may be partially hydrogen atoms, and the remainder may be deuterium atoms.

In Formula 3-2 to Formula 3-13, $R_{1a}$ to $R_{16a}$ may each independently be a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms. For example, $R_{1a}$ to $R_{16a}$ may be substituents that are not hydrogen atoms or deuterium atoms. For example, $R_{1a}$ to $R_{16a}$ may be each independently a substituted or unsubstituted amine group, a substituted or unsubstituted methyl group, a substituted or unsubstituted t-butyl group, a substituted or unsubstituted octyl group, a substituted or unsubstituted cyclohexyl group, a substituted or unsubstituted adamantyl group, a substituted or unsubstituted phenyl group, a substituted or unsubstituted naphthyl group, a substituted or unsubstituted anthracene group, or a substituted or unsubstituted fluorenyl group.

In Formula 3-1 to Formula 3-13, $Y_1$, $Y_2$, $R_{17}$ and $R_{18}$ may be the same as defined in connection with Formula 1.

In an embodiment, the fused polycyclic compound of an embodiment may be any one selected from Compound Group 1 below. The light emitting device ED of an embodiment may include at least one fused polycyclic compound selected from Compound Group 1 in an emission layer EML.

[Compound Group 1]
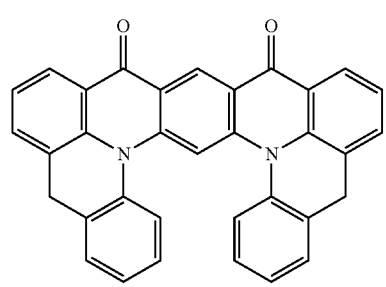 1
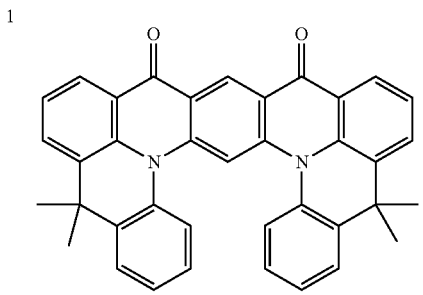 2
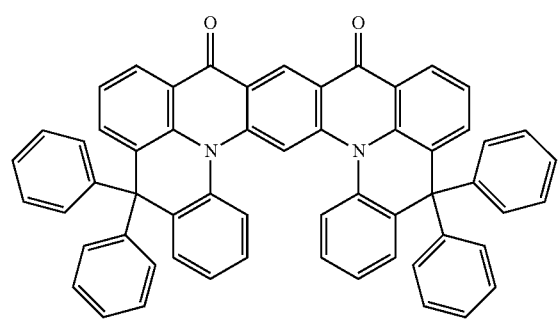 3
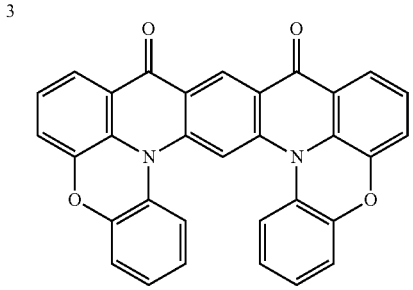 4
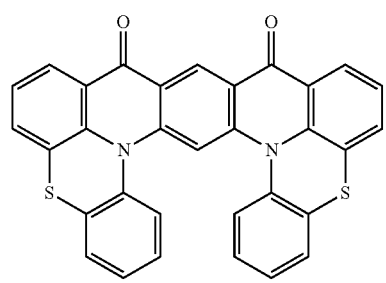 5
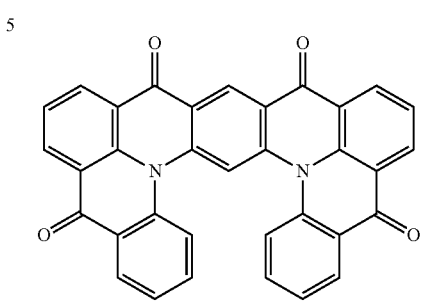 6
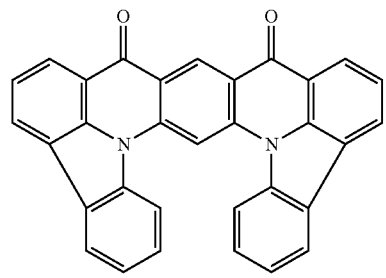 7
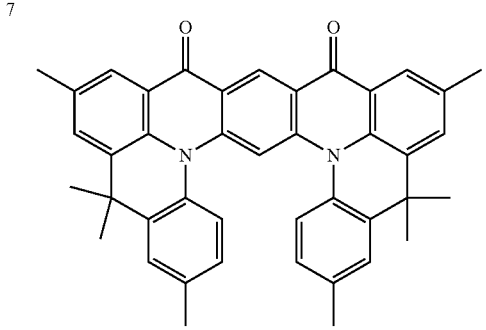 8
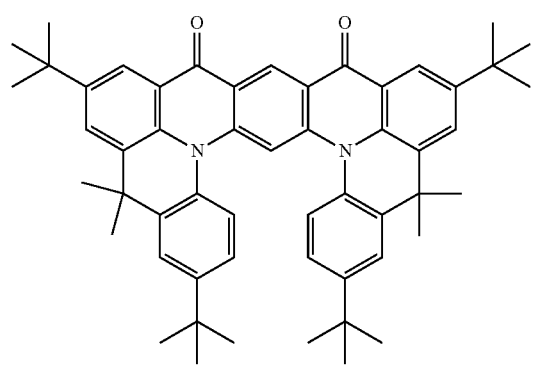 9
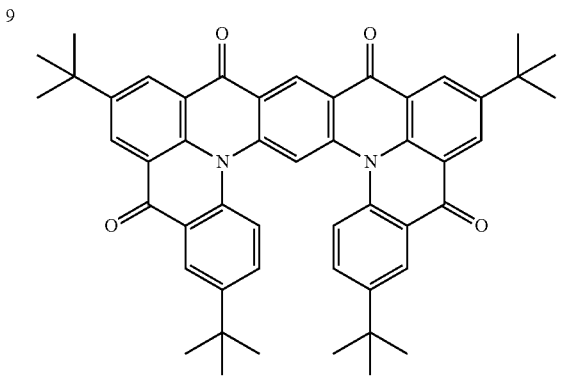 10

-continued
11
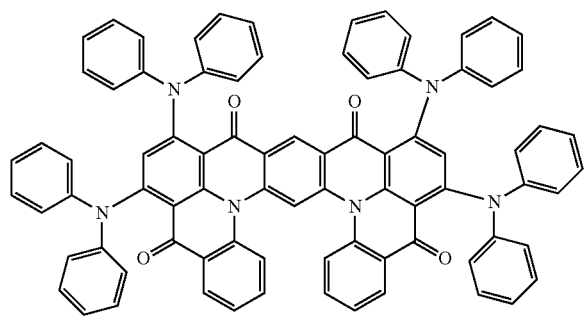
12
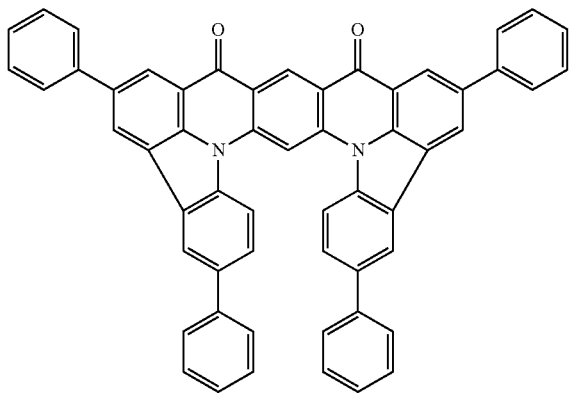
14
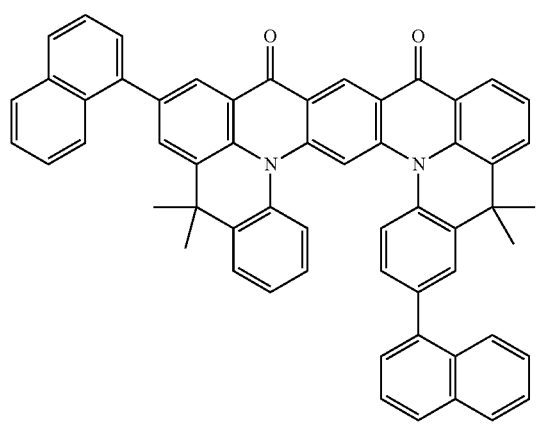
15
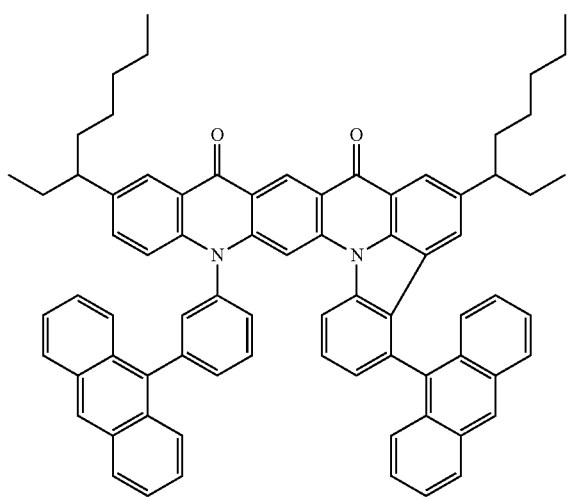
16
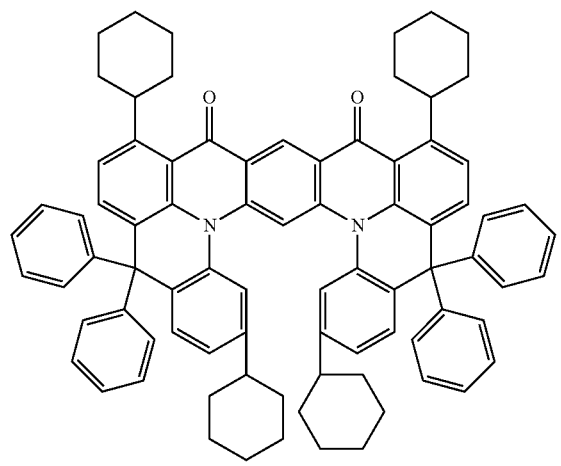
17
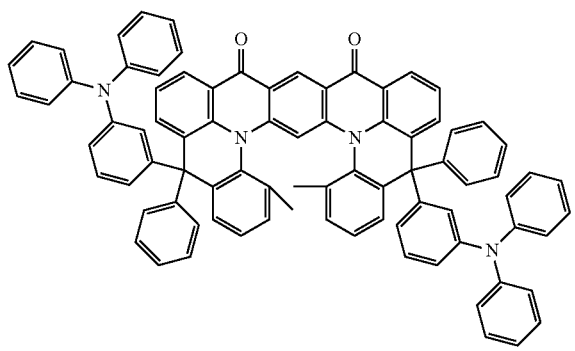

-continued
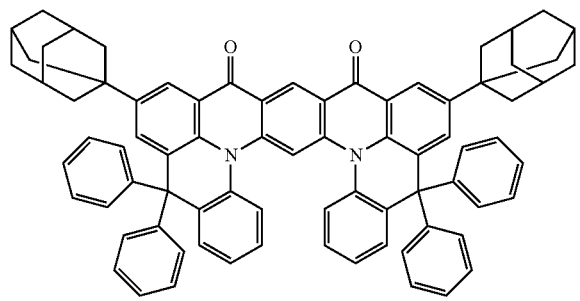
18
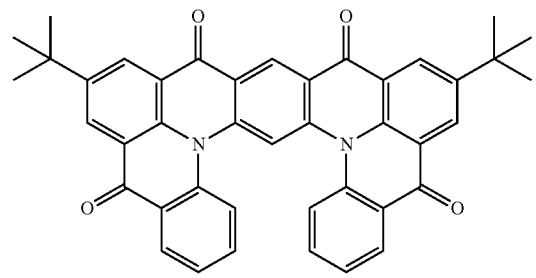
19
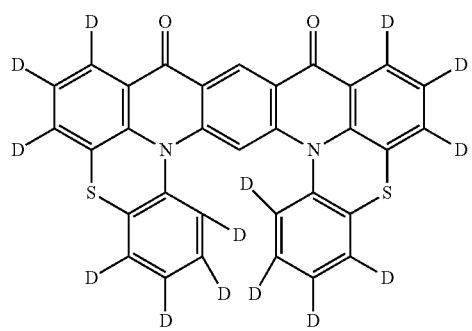
20
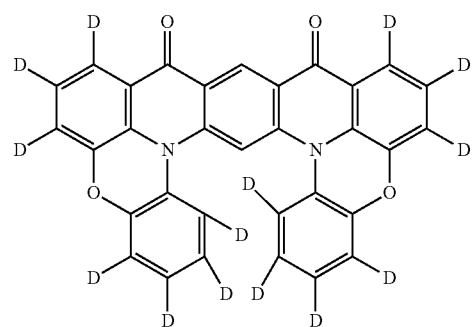
21
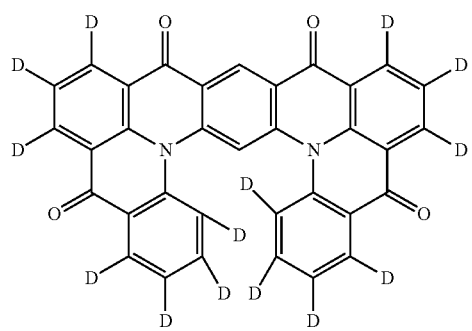
22
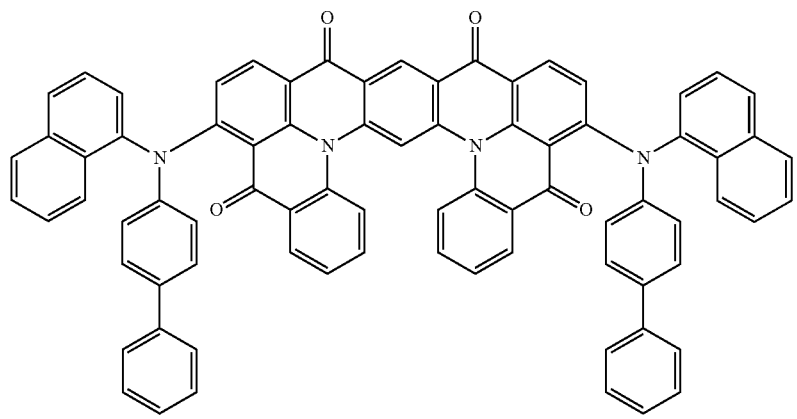
23

-continued
24
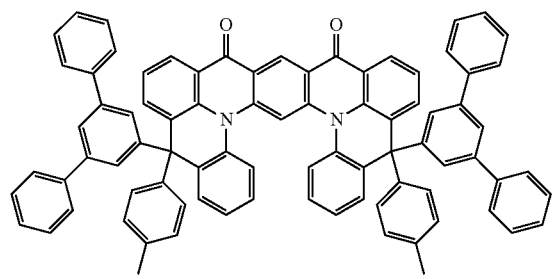
25
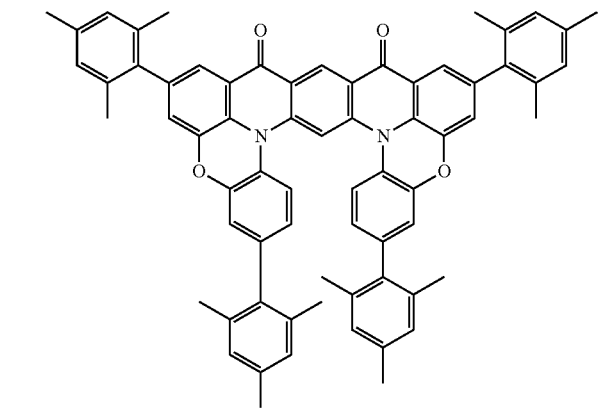
26
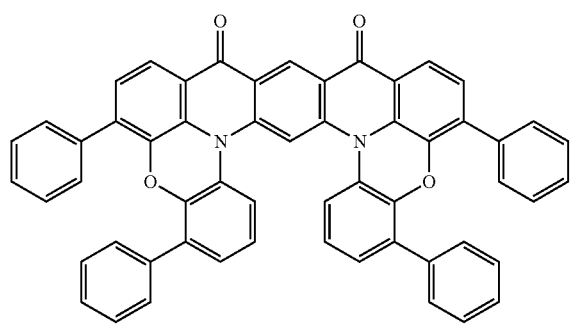
27
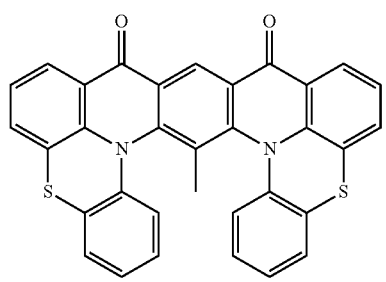
28
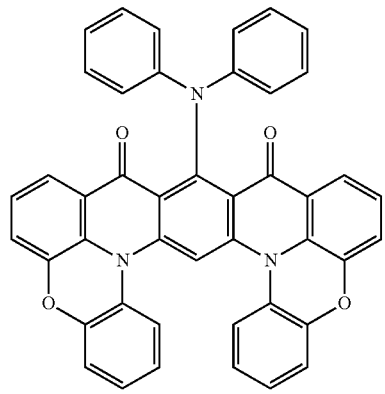
29
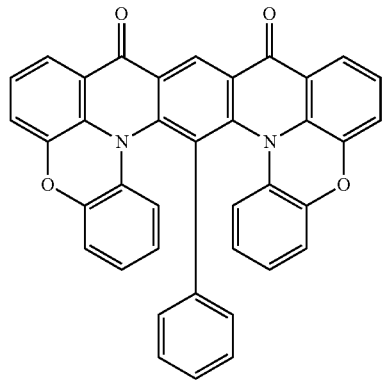
30
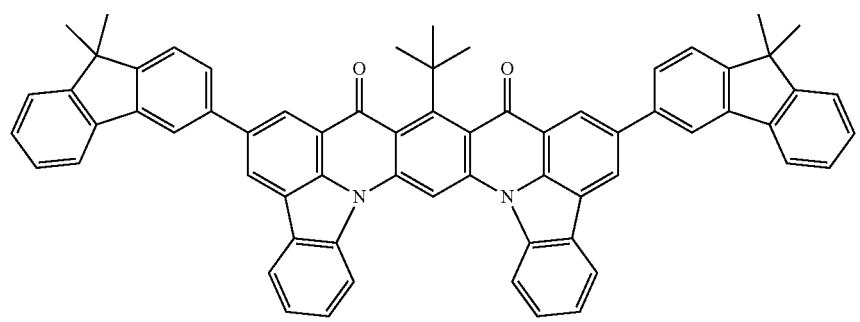

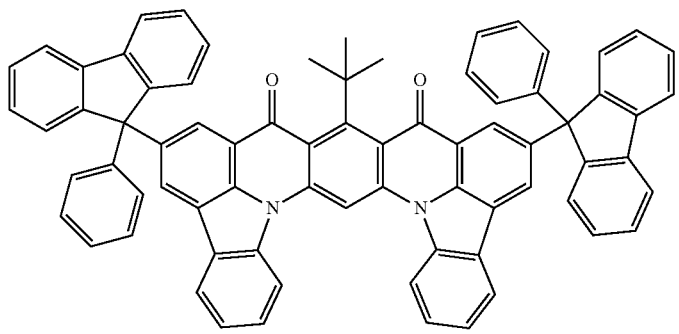

The light emission spectrum of the fused polycyclic compound of an embodiment, represented by Formula 1, may have a full width at half maximum (FWHM) in a range of about 10 nm to about 50 nm. For example, the light emission spectrum of the fused polycyclic compound of an embodiment may have a FWHM in a range of about 20 nm to about 40 nm. Since the light emission spectrum of the fused polycyclic compound of an embodiment, represented by Formula 1, has the full width at half maximum in the above-described range, emission efficiency may be improved in a light emitting device that includes the fused polycyclic compound. When the fused polycyclic compound of an embodiment is used as a blue light emitting material for a light emitting device, device life may be improved.

The fused polycyclic compound of an embodiment, represented by Formula 1, may be a material for emitting thermally activated delayed fluorescence. The fused polycyclic compound of an embodiment represented by Formula 1, may be a thermally activated delayed fluorescence dopant having a difference ($\Delta E_{ST}$) between the lowest triplet excitation energy level (T1 level) and the lowest singlet excitation energy level (S1 level) equal to or less than about 0.6 eV. The fused polycyclic compound of an embodiment, represented by Formula 1, may be a thermally activated delayed fluorescence dopant having a difference ($\Delta E_{ST}$) between the lowest triplet excitation energy level (T1 level) and the lowest singlet excitation energy level (S1 level) equal to or less than about 0.2 eV.

The fused polycyclic compound of an embodiment, represented by Formula 1, may be a light emitting material having a central wavelength of light in a wavelength region in a range of about 430 nm to about 530 nm. For example, the fused polycyclic compound of an embodiment, represented by Formula 1, may be a blue thermally activated delayed fluorescence (TADF) dopant. However, embodiments are not limited thereto. When the fused polycyclic compound of an embodiment is used as a light emitting material, the fused polycyclic compound may be used as a dopant material that emits light in various wavelength regions including a red light emitting dopant, a green light emitting dopant, etc.

In the light emitting device ED of an embodiment, an emission layer EML may emit delayed fluorescence. For example, the emission layer EML may emit thermally activated delayed fluorescence (TADF).

The emission layer EML of the light emitting device ED may emit blue light. For example, the emission layer EML of the light emitting device ED of an embodiment may emit blue light in a wavelength region equal to or less than about 490 nm. However, embodiments are not limited thereto. The emission layer EML may emit green light or red light.

In an embodiment, the emission layer EML may include a host and a dopant and may include the fused polycyclic compound as the dopant. For example, in the light emitting device ED of an embodiment, the emission layer EML may include a host for emitting delayed fluorescence and a dopant for emitting delayed fluorescence. The dopant for emitting delayed fluorescence may include the fused polycyclic compound. The emission layer EML may include at least one among the fused polycyclic compounds represented in Compound Group 1 as a thermally activated delayed fluorescence dopant.

In the light emitting device ED of an embodiment, the emission layer EML may further include a material, such as anthracene derivatives, pyrene derivatives, fluoranthene derivatives, chrysene derivatives, dihydrobenzanthracene derivatives, or triphenylene derivatives. In an embodiment, the emission layer EML may include anthracene derivatives or pyrene derivatives.

In the light emitting devices ED of embodiments, shown in FIG. 3 to FIG. 6, the emission layer EML may include a host and a dopant, and the emission layer EML may include a compound represented by Formula E-1 below. The compound represented by Formula E-1 below may be used as a fluorescence host material or a delayed fluorescence host material.

[Formula E-1]

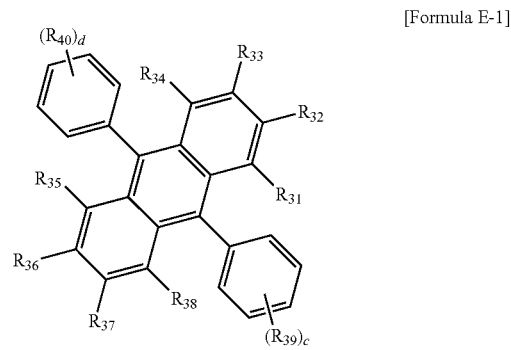

In Formula E-1, $R_{31}$ to $R_{40}$ may each independently be a hydrogen atom, a deuterium atom, a halogen atom, a substituted or unsubstituted silyl group, a substituted or unsubstituted alkyl group of 1 to 10 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula E-1, $R_{31}$ to $R_{40}$ may be combined with an adjacent group to form a saturated hydrocarbon ring or an unsaturated hydrocarbon ring.
In Formula E-1, c and d may each independently be an integer from 0 to 5.
The compound represented by Formula E-1 may be any one selected from Compound E1 to Compound E19 below.
E1
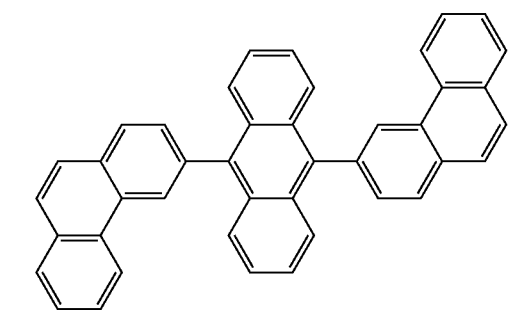
E2
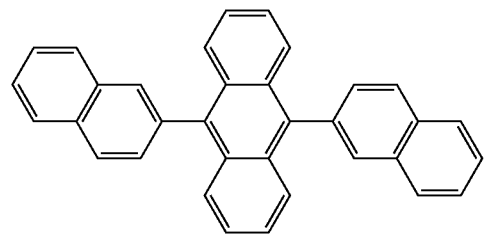
E3
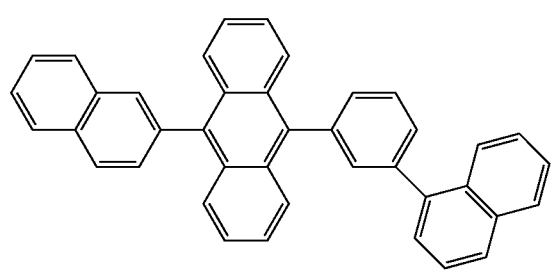
E4
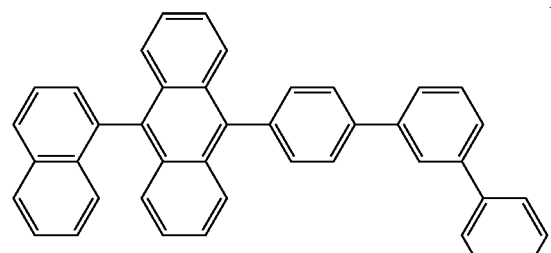
E5
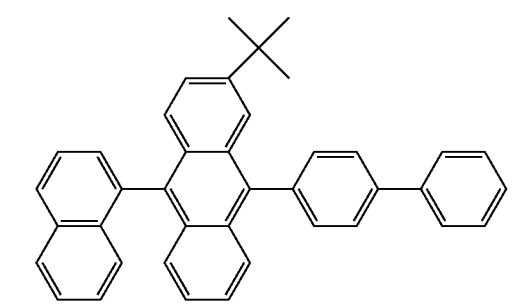
-continued
E6
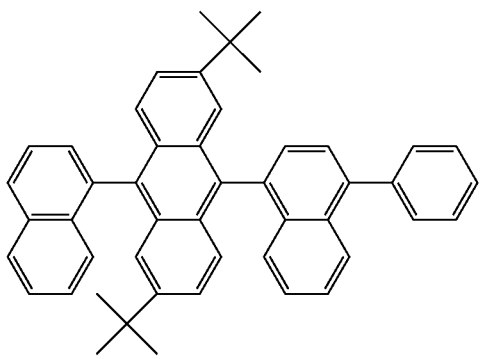
E7
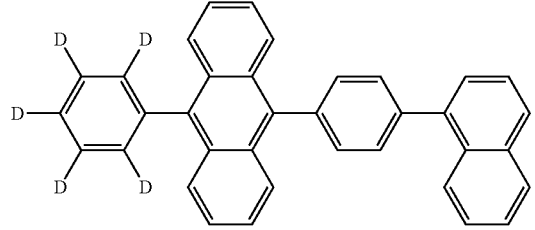
E8
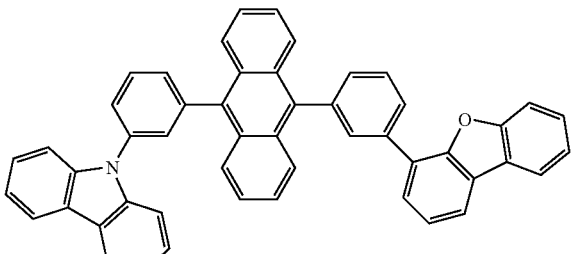
E9
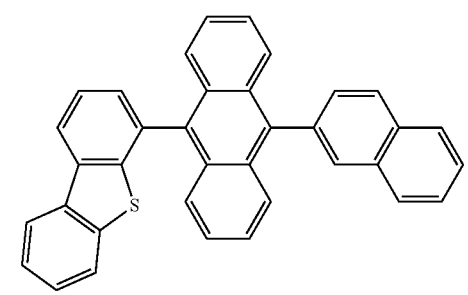
E10
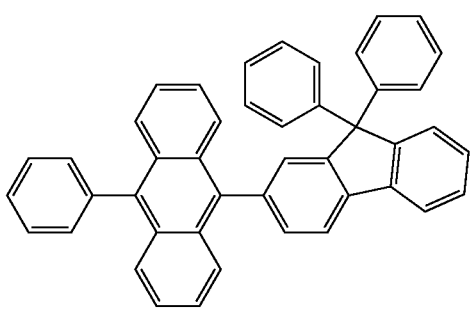

-continued
E11
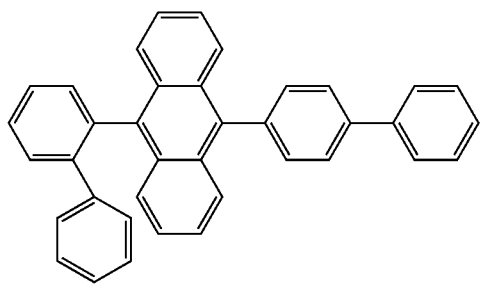
E12
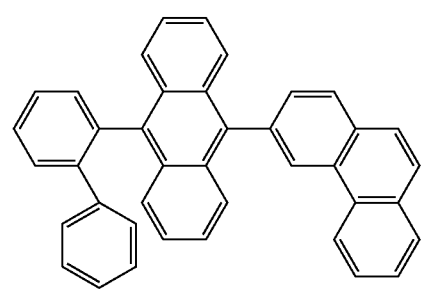
E13
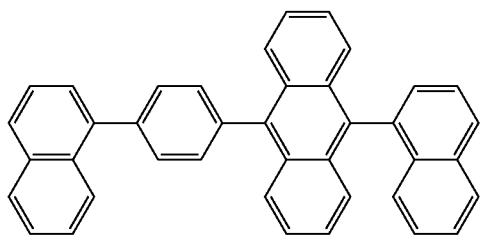
E14
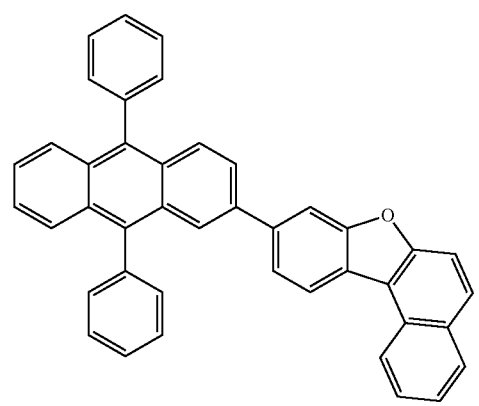
-continued
E15
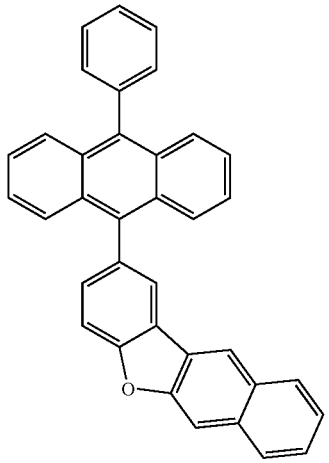
E16
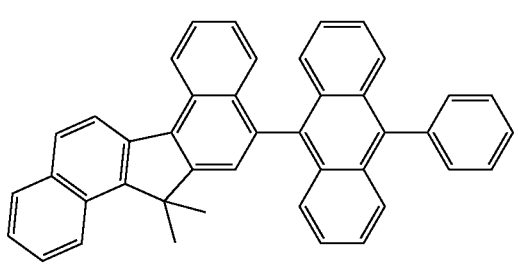
E17
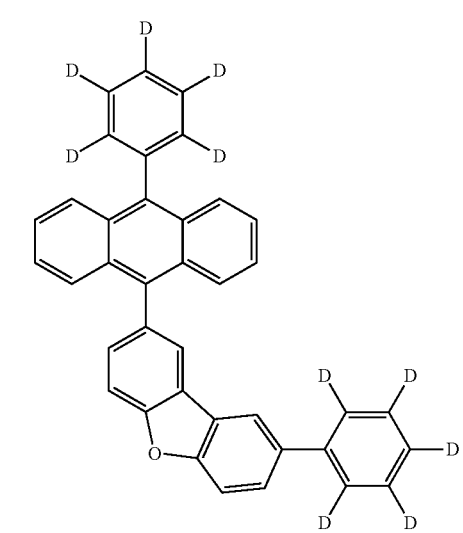
E18
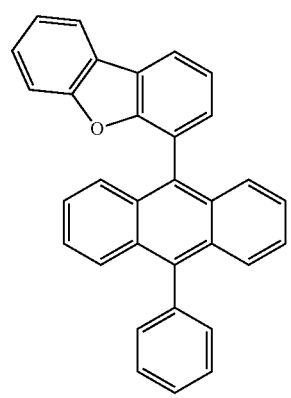

E19

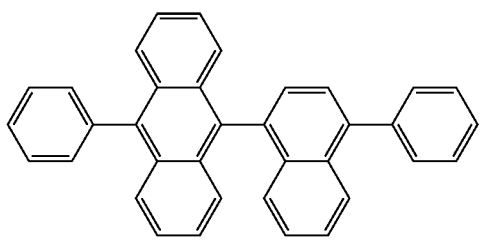

In an embodiment, the emission layer EML may include a compound represented by Formula E-2a or Formula E-2b below. The compound represented by Formula E-2a or Formula E-2b below may be used as a phosphorescence host material or a delayed fluorescence host material.

[Formula E-2a]

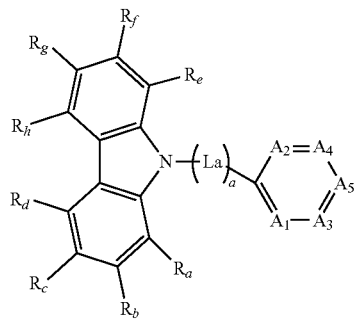

In Formula E-2a, a may be an integer from 0 to 10, and $L_a$ may be a direct linkage, a substituted or unsubstituted arylene group of 6 to 30 ring-forming carbon atoms, or a substituted or unsubstituted heteroarylene group of 2 to 30 ring-forming carbon atoms. In Formula E-2a, if a is 2 or more, multiple $L_a$ groups may each independently be a substituted or unsubstituted arylene group of 6 to 30 ring-forming carbon atoms, or a substituted or unsubstituted heteroarylene group of 2 to 30 ring-forming carbon atoms.

In Formula E-2a, $A_1$ to $A_5$ may each independently be N or $C(R_i)$. In Formula E-2a, $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. $R_a$ to $R_i$ may be combined with an adjacent group to form a hydrocarbon ring or a heterocycle including N, O, S, etc. as a ring-forming atom.

In Formula E-2a, two or three of $A_1$ to $A_5$ may be N, and the remainder of $A_1$ to $A_5$ may be $C(R_i)$.

[Formula E-2b]

(Cbz1)―(L_b)_b―(Cbz2)

In Formula E-2b, Cbz1 and Cbz2 may each independently be an unsubstituted carbazole group, or a carbazole group substituted with an aryl group of 6 to 30 ring-forming carbon atoms. In Formula E-2b, $L_b$ may be a direct linkage, a substituted or unsubstituted arylene group of 6 to 30 ring-forming carbon atoms, or a substituted or unsubstituted heteroarylene group of 2 to 30 ring-forming carbon atoms. In Formula E-2b, b may be an integer from 0 to 10, and if b is 2 or more, multiple $L_b$ groups may each independently be a substituted or unsubstituted arylene group of 6 to 30 ring-forming carbon atoms, or a substituted or unsubstituted heteroarylene group of 2 to 30 ring-forming carbon atoms.

The compound represented by Formula E-2a or Formula E-2b may be any one selected from Compound Group E-2 below. However, the compounds shown in Compound Group E-2 below are only examples, and the compound represented by Formula E-2a or Formula E-2b is not limited to the compounds in Compound Group E-2 below.

[Compound Group E-2]

E-2-1

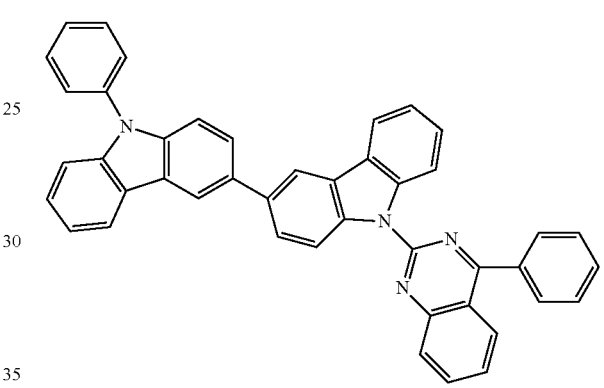

E-2-2

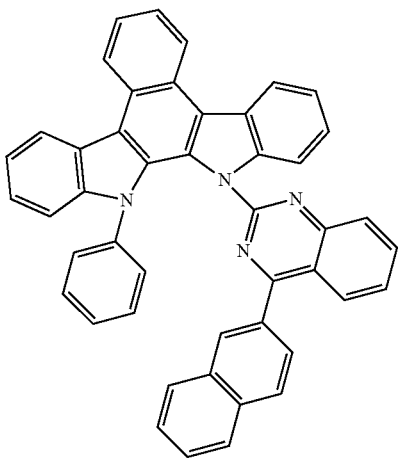

E-2-3
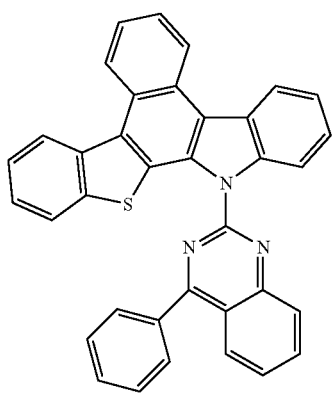
E-2-6
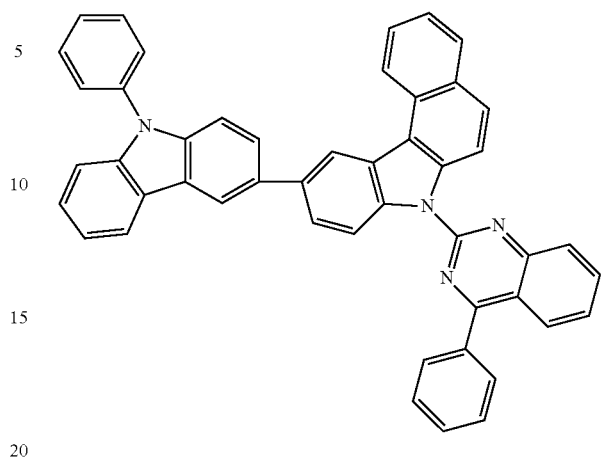
E-2-4
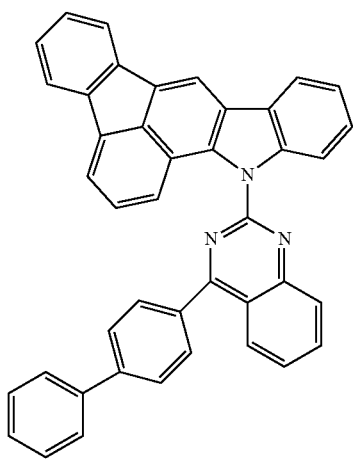
E-2-7
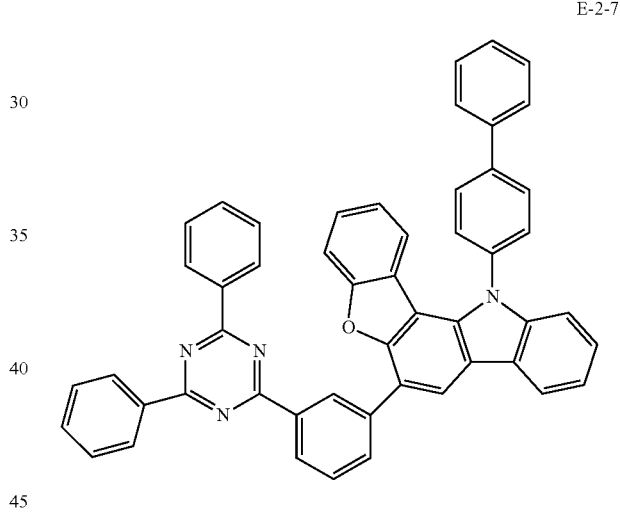
E-2-5
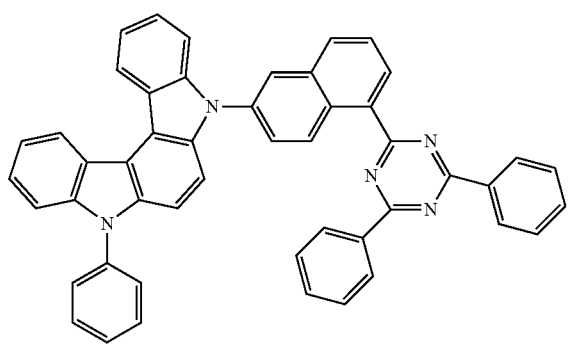
E-2-8
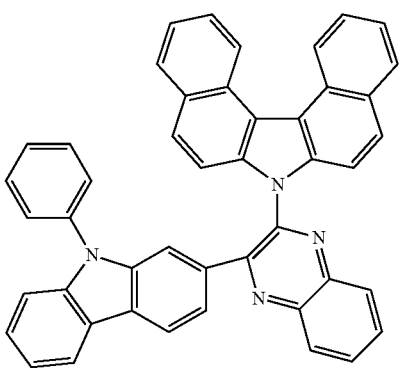

E-2-9
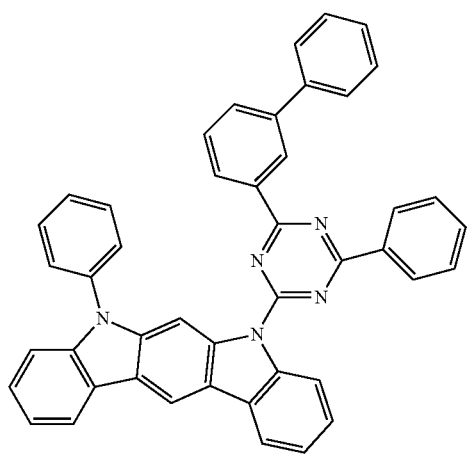
E-2-10
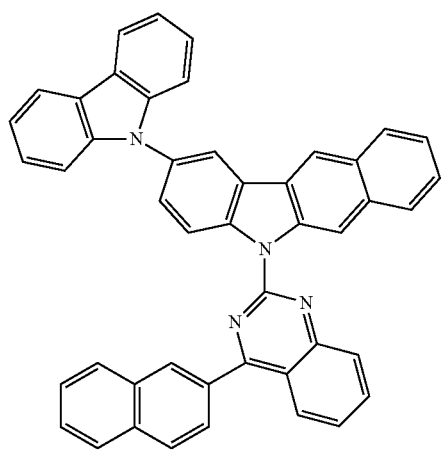
E-2-11
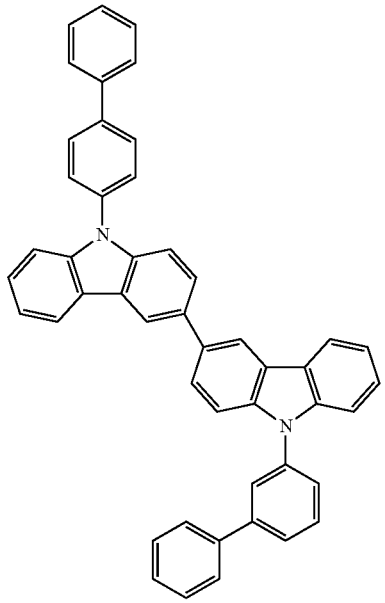
E-2-12
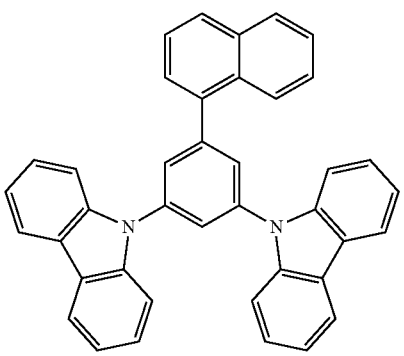
E-2-13
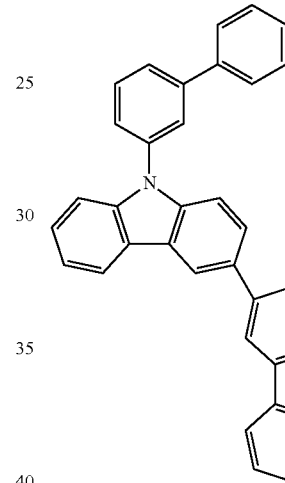
E-2-14
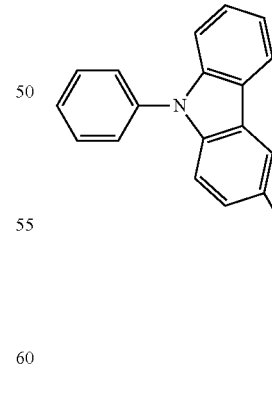

E-2-15
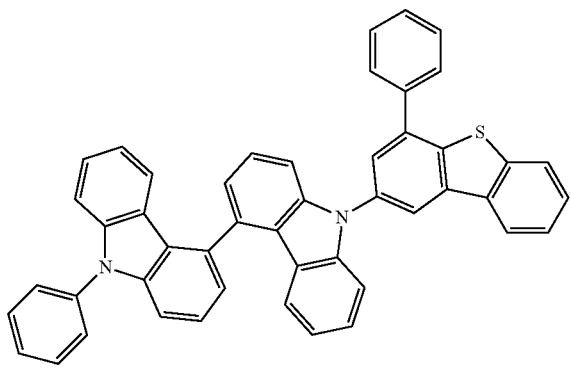
E-2-19
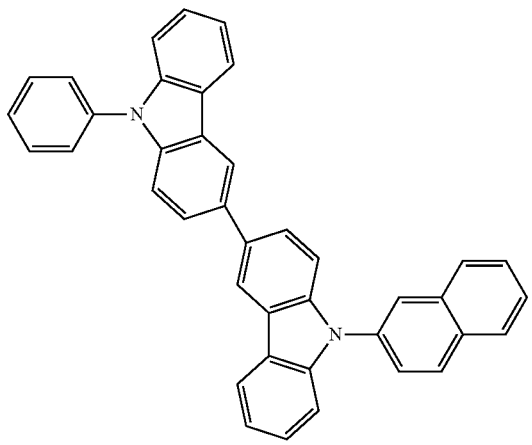
E-2-16
E-2-20
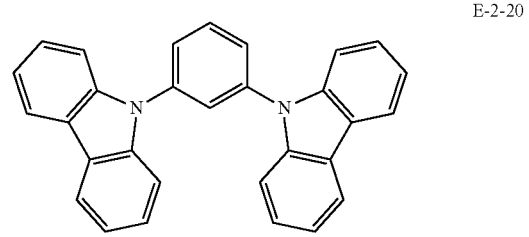
E-2-17
E-2-21
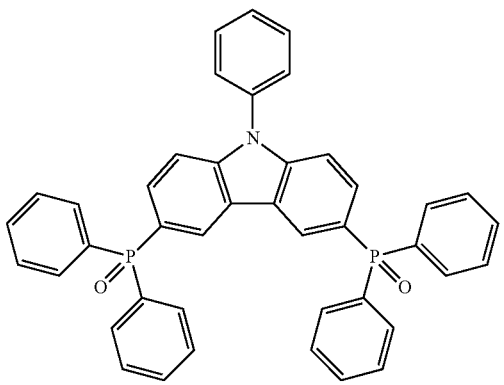
E-2-18
E-2-22
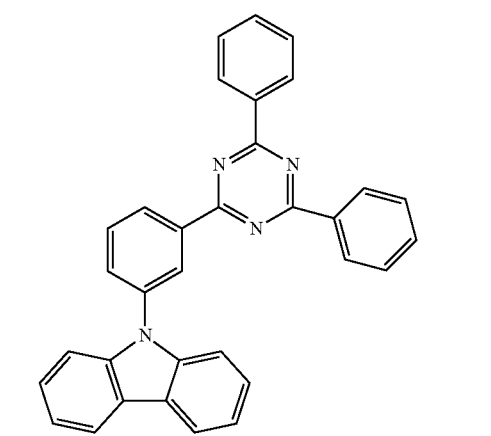

E-2-23

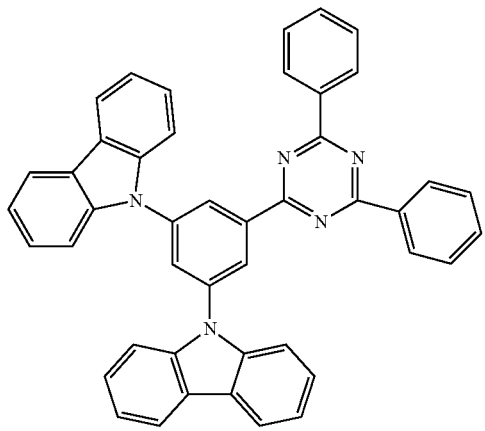

E-2-24

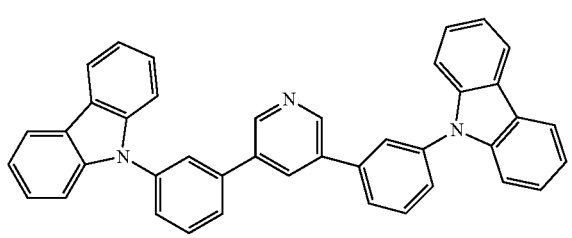

E-2-25

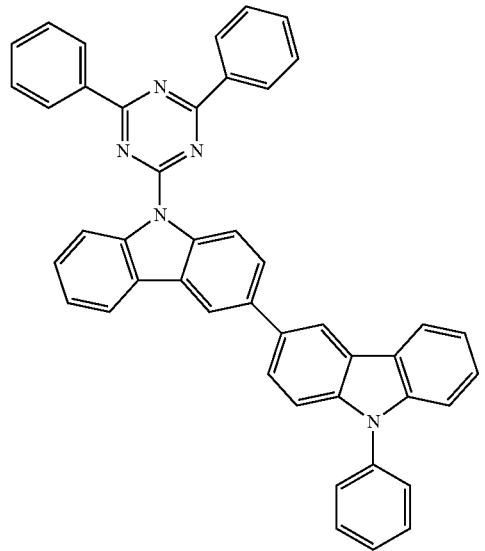

The emission layer EML may further include a common material in the art as a host material. For example, the emission layer EML may include as a host material, at least one of bis[2-(diphenylphosphino)phenyl]ether oxide (DPEPO), 4,4'-bis(carbazol-9-yl) biphenyl (CBP), 1,3-bis(carbazol-9-yl)benzene (mCP), 2,8-bis(diphenylphosphoryl)dibenzo[b,d]furan (PPF), 4,4',4''-tris(carbazol-9-yl)-triphenylamine (TCTA), and 1,3,5-tris(1-phenyl-1H-benzo[d]imidazole-2-yl)benzene (TPBi). However, embodiments are not limited thereto. For example, tris(8-hydroxyquinolino) aluminum (Alq$_3$), 4,4'-bis(N-carbazolyl)-1,1'-biphenyl (CBP), poly(N-vinylcarbazole) (PVK), 9,10-di(naphthalene-2-yl) anthracene (ADN), 4,4',4''-tris(carbazol-9-yl)-triphenyamine (TCTA), 1,3,5-tris(N-phenylbenzimidazole-2-yl)benzene (TPBi), 2-tert-butyl-9,10-di(naphth-2-yl) anthracene (TBADN), distyrylarylene (DSA), 4,4'-bis(9-carbazolyl)-2,2'-dimethyl-biphenyl (CDBP), 2-methyl-9,10-bis(naphthalen-2-yl) anthracene (MADN), hexaphenyl cyclotriphosphazene (CP1), 1,4-bis(triphenylsilyl)benzene (UGH2), hexaphenylcyclotrisiloxane (DPSiO$_3$), octaphenylcyclotetra siloxane (DPSiO$_4$), 2,8-bis(diphenylphosphoryl)dibenzofuran (PPF), etc. may be used as the host material.

The emission layer EML may include a compound represented by Formula M-a or Formula M-b below. The compound represented by Formula M-a or Formula M-b may be used as a phosphorescence dopant material.

[Formula M-a]

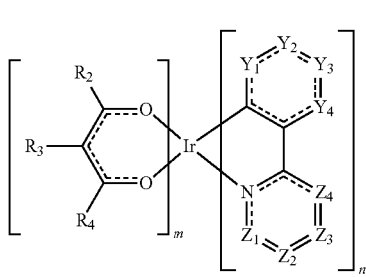

In Formula M-a, $Y_1$ to $Y_4$ and $Z_1$ to $Z_4$ may each independently be $C(R_1)$ or N, and $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula M-a, m may be 0 or 1, and n may be 2 or 3. In Formula M-a, if m is 0, n may be 3, and if m is 1, n may be 2.

The compound represented by Formula M-a may be used as a red phosphorescence dopant or a green phosphorescence dopant.

The compound represented by Formula M-a may be any one selected from Compounds M-a1 to M-a19 below. However, Compounds M-a1 to M-a19 below are examples, and the compound represented by Formula M-a is not limited to Compounds M-a1 to M-a19 below.

M-a1

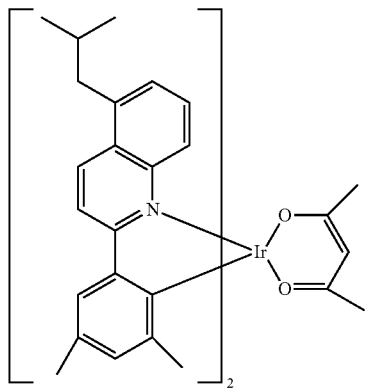

M-a2
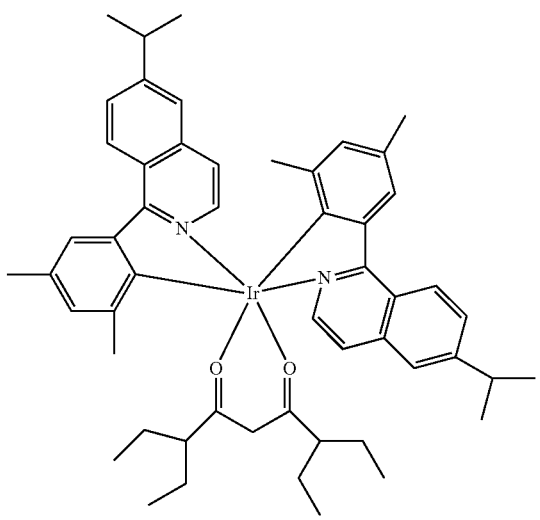
M-a3
M-a4
M-a5
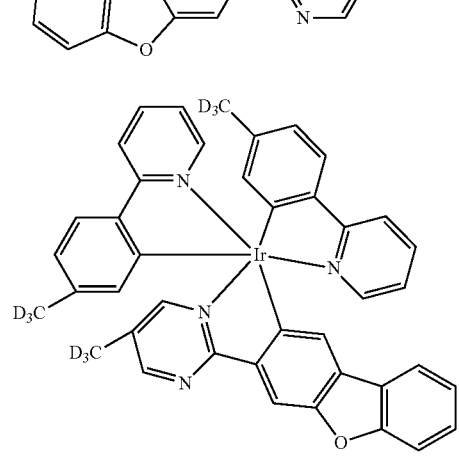
M-a6
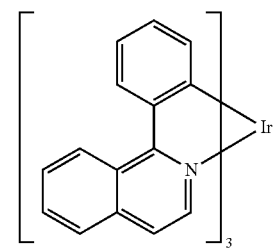
M-a7
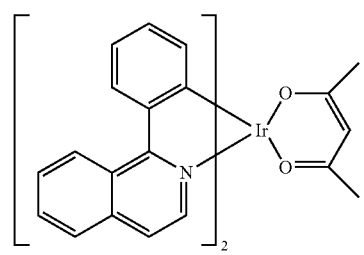
M-a8
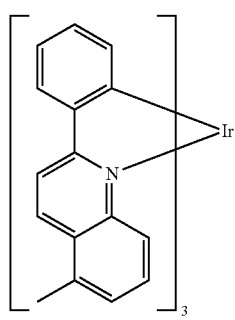
M-a9
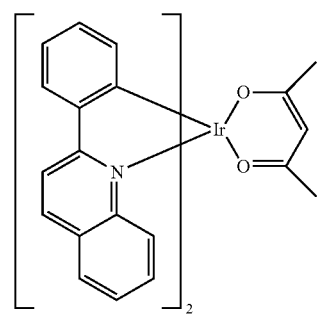
M-a10
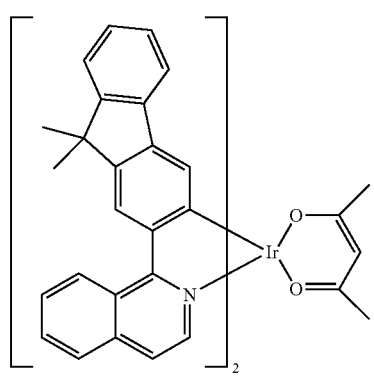

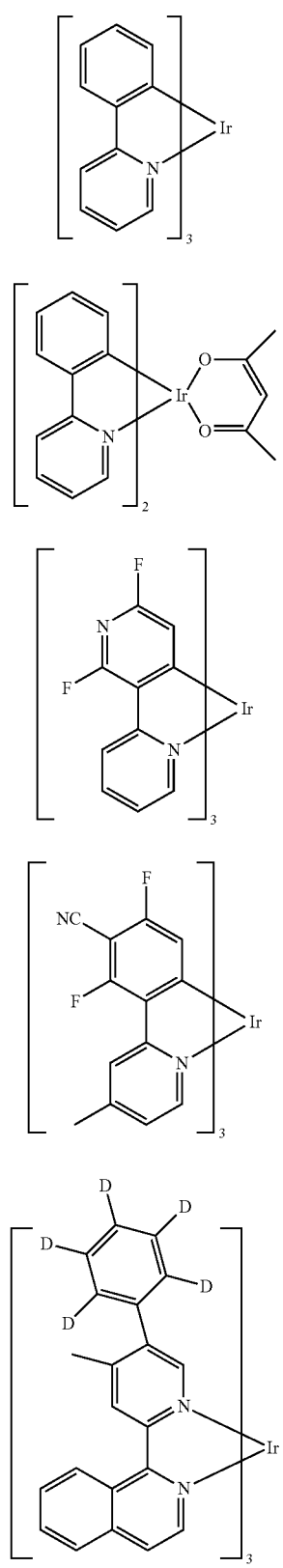
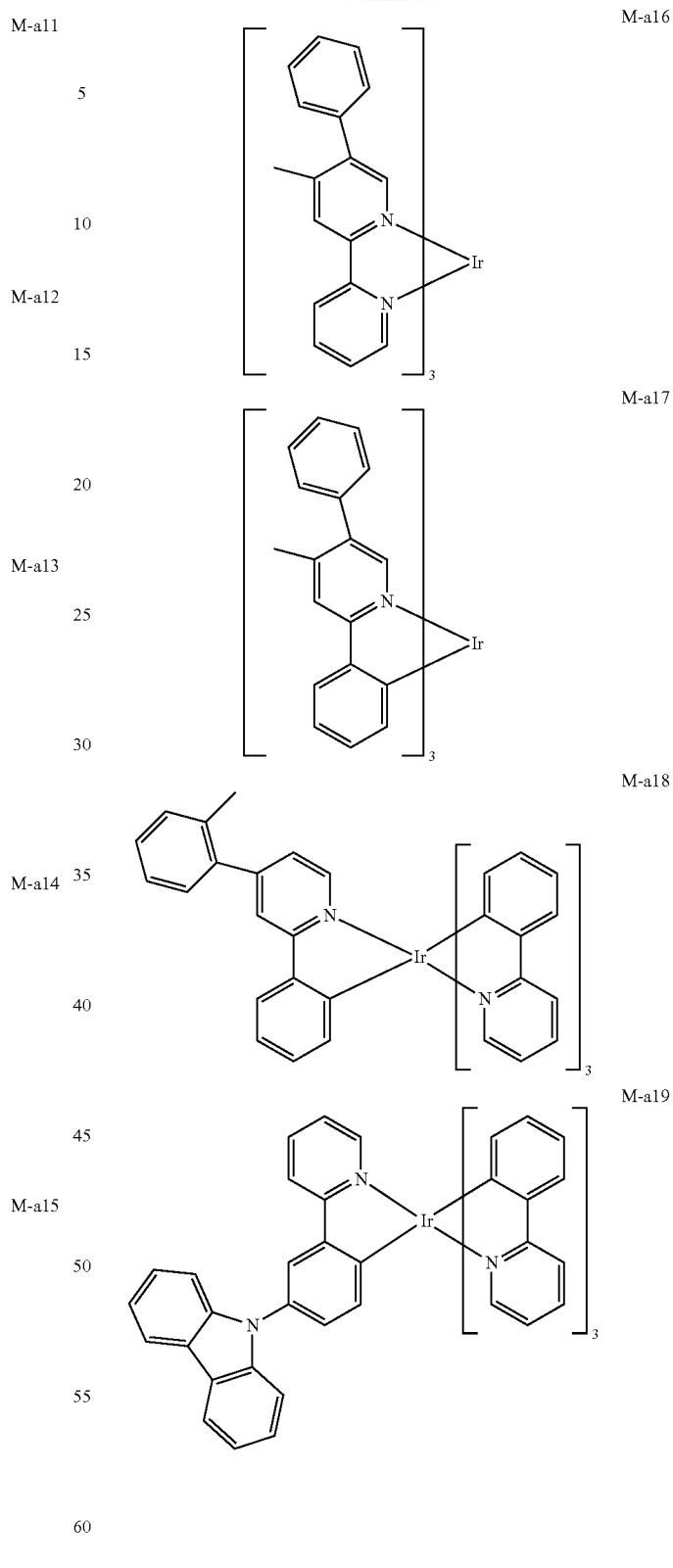
Compound M-a1 and Compound M-a2 may be used as red dopant materials, and Compound M-a3 to Compound M-a5 may be used as green dopant materials.

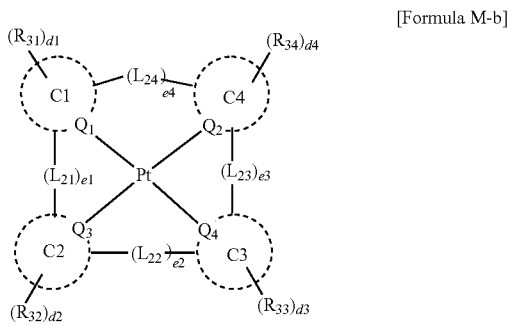

[Formula M-b]

In Formula M-b, $Q_1$ to $Q_4$ may each independently be C or N, and C1 to C4 may each independently be a substituted or unsubstituted hydrocarbon ring of 5 to 30 ring-forming carbon atoms, or a substituted or unsubstituted heterocycle of 2 to 30 ring-forming carbon atoms. In Formula M-b, $L_{21}$ to $L_{24}$ may each independently be a direct linkage,

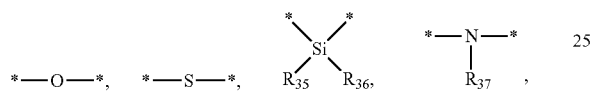

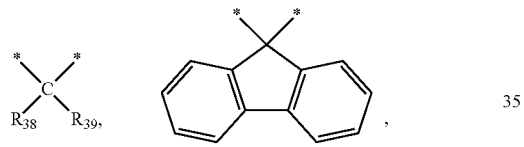

a substituted or unsubstituted divalent alkyl group of 1 to 20 carbon atoms, a substituted or unsubstituted arylene group of 6 to 30 ring-forming carbon atoms, or a substituted or unsubstituted heteroarylene group of 2 to 30 ring-forming carbon atoms, and e1 to e4 may each independently be 0 or 1. In Formula M-b, $R_{31}$ to $R_{39}$ may each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring, and d1 to d4 may each independently be an integer from 0 to 4.

The compound represented by Formula M-b may be used as a blue phosphorescence dopant or a green phosphorescence dopant.

The compound represented by Formula M-b may be any one selected from the compounds below. However, the compounds below are examples, and the compound represented by Formula M-b is not limited to the compounds below.

M-b-1

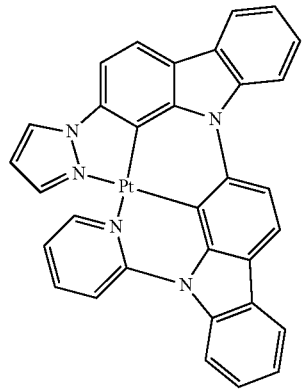

M-b-2

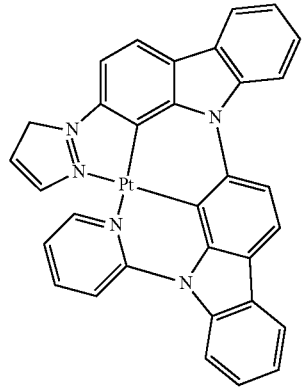

M-b-3

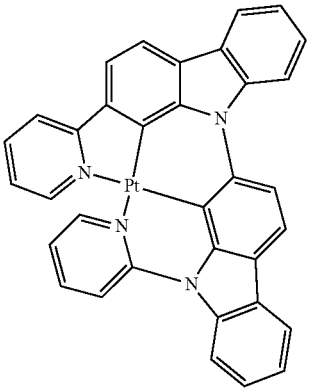

M-b-4

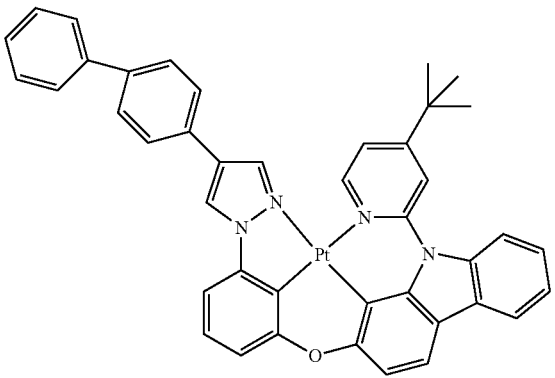

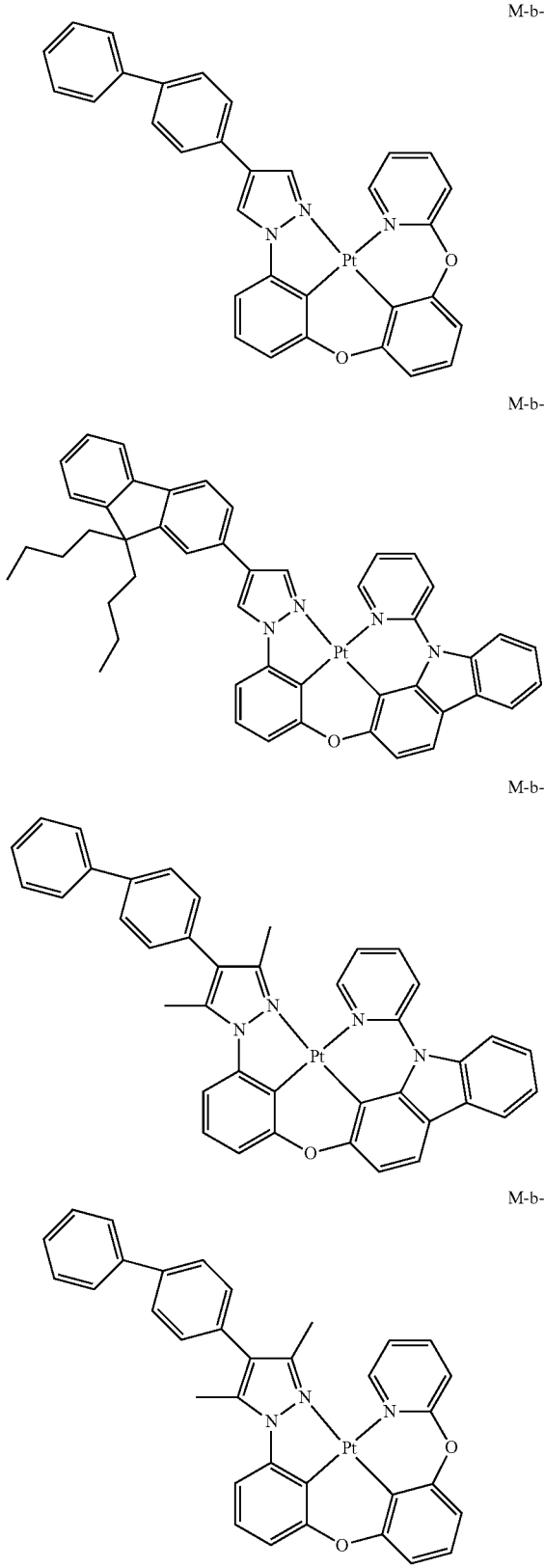
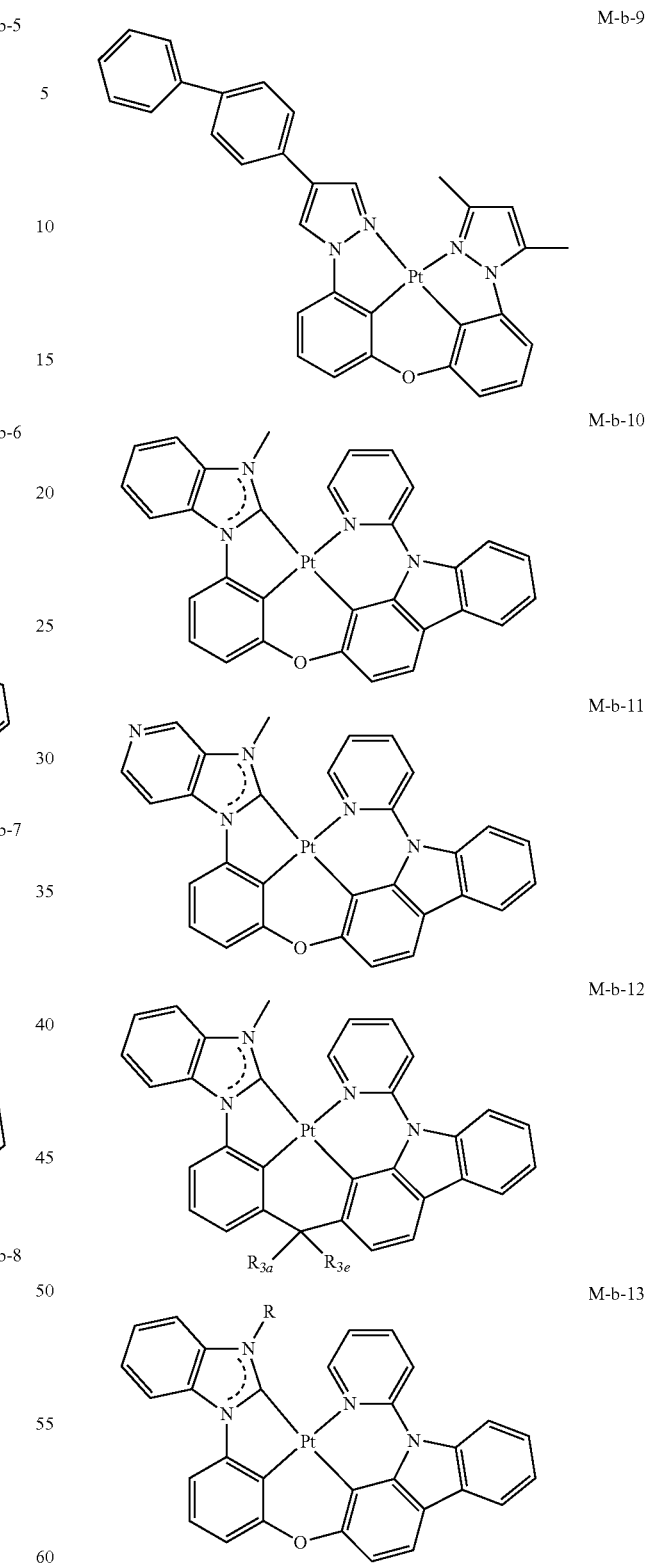
In the compounds above, R, $R_{38}$, and $R_{39}$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

The emission layer EML may include any one among Formula F-a to Formula F-c below. The compounds represented by any one of Formula F-a to Formula F-c below may be used as fluorescence dopant materials.

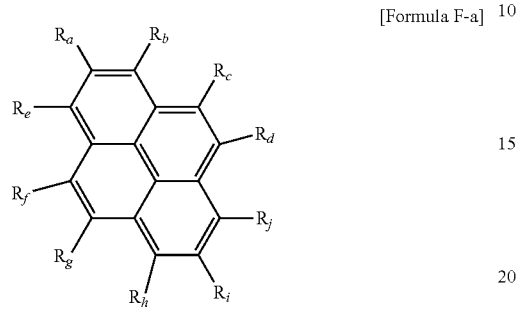

[Formula F-a]

In Formula F-a, two selected from $R_a$ to $R_j$ may each independently be substituted with *—$NAr_1Ar_2$. The remainder $R_a$ to $R_j$ which are not substituted with *—$NAr_1Ar_2$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In the group *—$NAr_1Ar_2$, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms. For example, at least one among $Ar_1$ and $Ar_2$ may be a heteroaryl group including O or S as a ring-forming atom.

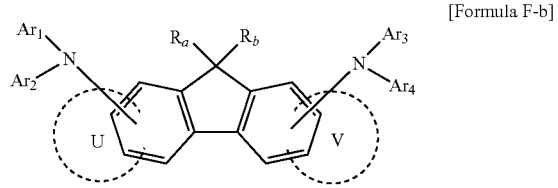

[Formula F-b]

In Formula F-b, $R_a$ and Rb may each independently be a hydrogen atom, a deuterium atom, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring.

In Formula F-b, U and V may each independently be a substituted or unsubstituted hydrocarbon ring of 5 to 30 ring-forming carbon atoms, or a substituted or unsubstituted heterocycle of 2 to 30 ring-forming carbon atoms.

In Formula F-b, the number of rings represented by U and V may each independently be 0 or 1. For example, in Formula F-b, if the number of U or V is 1, one ring may form a fused ring at the designated part by U or V, and if the number of U or V is 0, a ring may not be present at the designated part by U or V. If the number of U is 0 and the number of V is 1, or if the number of U is 1 and the number of V is 0, a fused ring having the fluorene core of Formula F-b may be a cyclic compound with four rings. If the number of both U and V is 0, the fused ring of Formula F-b may be a cyclic compound with three rings. If the number of U and V is each 1, a fused ring having the fluorene core of Formula F-b may be a cyclic compound with five rings.

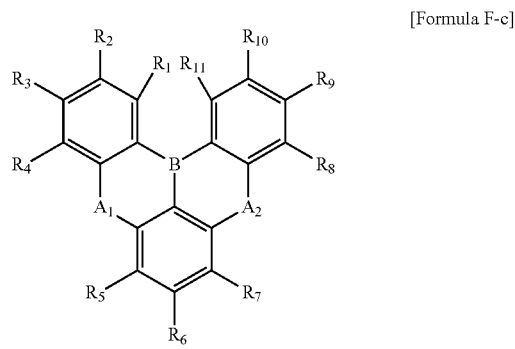

[Formula F-c]

In Formula F-c, $A_1$ and $A_2$ may each independently be O, S, Se, or $N(R_m)$, and $R_m$ may be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. In Formula F-c, $R_1$ to $R_{11}$ may each independently be a hydrogen atom, a deuterium atom, a halogen atom, a cyano group, a substituted or unsubstituted amine group, a substituted or unsubstituted boron group, a substituted or unsubstituted oxy group, a substituted or unsubstituted thio group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring.

In Formula F-c, $A_1$ and $A_2$ may each independently be combined with the substituents of an adjacent ring to form a fused ring. For example, if $A_1$ and $A_2$ are each $N(R_m)$, $A_1$ may be combined with $R_4$ or $R_5$ to form a ring. For example, $A_2$ may be combined with $R_7$ or $R_8$ to form a ring.

In an embodiment, the emission layer EML may include as a dopant material, styryl derivatives (for example, 1,4-bis[2-(3-N-ethylcarbazoryl) vinyl]benzene (BCzVB), 4-(di-p-tolylamino)-4'-[(di-p-tolylamino) styryl]stilbene (DPAVB), N-(4-((E)-2-(6-((E)-4-(diphenylamino) styryl) naphthalen-2-yl) vinyl)phenyl)-N-phenylbenzenamine (N-BDAVBi), and 4,4'-bis[2-(4-(N,N-diphenylamino)phenyl) vinyl]biphenyl (DPAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, and 1,4-bis(N,N-diphenylamino) pyrene), etc.

The emission layer EML may include a phosphorescence dopant material. For example, the phosphorescence dopant may use a metal complex including iridium (Ir), platinum (Pt), osmium (Os), gold (Au), titanium (Ti), zirconium (Zr), hafnium (Hf), europium (Eu), terbium (Tb), or thulium (Tm). In an embodiment, iridium (III) bis(4,6-difluorophenylpyridinato-N,C2') picolinate (FIrpic), bis(2,4-difluorophenylpyridinato)-tetrakis (1-pyrazolyl) borate iridium (III) (Fir6), or platinum octaethyl porphyrin (PtOEP) may be used as the phosphorescence dopant. However, embodiments are not limited thereto.

The emission layer EML may include a quantum dot material. The core of the quantum dot may be selected from a II-VI group compound, a III-VI group compound, a I-III-VI group compound, a III-V group compound, a IV-VI group compound, a IV group element, a IV group compound, and combinations thereof.

The II-VI group compound may be selected from the group consisting of: a binary compound selected from the group consisting of CdSe, CdTe, CdS, ZnS, ZnSe, ZnTe, ZnO, HgS, HgSe, HgTe, MgSe, MgS, and mixtures thereof; a ternary compound selected from the group consisting of CdSeS, CdSeTe, CdالسTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and mixtures thereof; and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and mixtures thereof.

The III-VI group compound may include a binary compound such as $In_2S_3$, and $In_2Se_3$, a ternary compound such as $InGaS_3$, and $InGaSe_3$, or combinations thereof.

The I-III-VI group compound may be selected from a ternary compound selected from the group consisting of AgInS, $AgInS_2$, CuInS, $CuInS_2$, $AgGaS_2$, $CuGaS_2$, $CuGaO_2$, $AgGaO_2$, $AgAlO_2$ and mixtures thereof, or a quaternary compound such as $AgInGaS_2$, and $CuInGaS_2$.

The III-V group compound may be selected from the group consisting of a binary compound selected from the group consisting of GaN, GaP, GaAs, GaSb, AlN, AlP, AlAs, AlSb, InN, InP, InAs, InSb, and mixtures thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and mixtures thereof, and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and mixtures thereof. The III-V group compound may further include a II group metal. For example, InZnP, etc. may be selected as a III-II-V group compound.

The IV-VI group compound may be selected from the group consisting of a binary compound selected from the group consisting of SnS, SnSe, SnTe, PbS, PbSe, PbTe, and mixtures thereof, a ternary compound selected from the group consisting of SnSeS, SnSeTe, SnSTe, PbSeS, PbSeTe, PbSTe, SnPbS, SnPbSe, SnPbTe, and mixtures thereof, and a quaternary compound selected from the group consisting of SnPbSSe, SnPbSeTe, SnPbSTe, and mixtures thereof. The IV group element may be selected from the group consisting of Si, Ge, and a mixture thereof. The IV group compound may be a binary compound selected from the group consisting of SiC, SiGe, and a mixture thereof.

The binary compound, the ternary compound, or the quaternary compound may be present at a uniform concentration in a particle or may be present at a partially different concentration distribution state in the same particle. A quantum dot may have a core/shell structure in which one quantum dot wraps another quantum dot. The interface of the core and the shell may have a concentration gradient in which the concentration of an element present in the shell is decreased toward the core.

In an embodiment, the quantum dot may have the above-described core-shell structure including a core including a nanocrystal and a shell wrapping the core. The shell of the quantum dot may be a protection layer for preventing the chemical deformation of the core to maintain semiconductor properties and/or a charging layer for imparting the quantum dot with electrophoretic properties. The shell may have a single layer or a multilayer. Examples of the shell of the quantum dot may include a metal or non-metal oxide, a semiconductor compound, or combinations thereof.

For example, the metal or non-metal oxide may include a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$ and NiO, or a ternary compound such as $MgAl_2O_4$, $CoFe_2O_4$, $NiFe_2O_4$ and $CoMn_2O_4$, but embodiments are not limited thereto.

For example, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments are not limited thereto.

The quantum dot may have a full width of half maximum (FWHM) of an emission wavelength spectrum equal to or less than about 45 nm. For example, the quantum dot may have a FWHM of an emission wavelength spectrum equal to or less than about 40 nm. For example, the quantum dot may have a FWHM of an emission wavelength spectrum equal to or less than about 30 nm. Within these ranges color purity or color reproducibility may be improved. Light emitted via such a quantum dot may be emitted in all directions, and light viewing angle properties may be improved.

The quantum dot may have a shape that is selected from among generally used shapes in the art, without specific limitation. For example, the quantum dot may have a spherical, a pyramidal, a multi-arm, or a cubic shape, or the quantum dot may be in the form of a nanoparticle, a nanotube, a nanowire, a nanofiber, a nanoplate, etc.

The quantum dot may control the color of light emitted according to the particle size, and accordingly, the quantum dot may have various emission colors such as blue, red, and green.

In the light emitting device ED of an embodiment, as shown in FIG. 3 to FIG. 6, the electron transport region ETR is provided on the emission layer EML. The electron transport region ETR may include at least one of a hole blocking layer HBL, an electron transport layer ETL, and an electron injection layer EIL. However, embodiments are not limited thereto.

The electron transport region ETR may have a single layer formed using a single material, a single layer formed using different materials, or a multilayer structure having layers formed using different materials.

For example, the electron transport region ETR may have a single layer structure of an electron injection layer EIL or an electron transport layer ETL, or a single layer structure formed using an electron injection material and an electron transport material. The electron transport region ETR may have a single layer structure formed using multiple different materials, or a structure stacked from the emission layer EML of an electron transport layer ETL/an electron injection layer EIL, or a hole blocking layer HBL/an electron transport layer ETL/an electron injection layer EIL, without limitation. A thickness of the electron transport region ETR may be, for example, in a range of about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

The electron transport region ETR may include a compound represented by Formula ET-1 below.

[Formula ET-1]

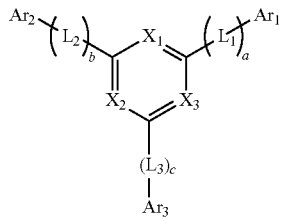

In Formula ET-1, at least one among $X_1$ to $X_3$ may be N, and the remainder of $X_1$ to $X_3$ may be $C(R_a)$. $R_a$ may be a hydrogen atom, a deuterium atom, a substituted or unsubstituted alkyl of 1 to 20 carbon atoms, a substituted or unsubstituted aryl group of 6 to 30 ring-forming carbon atoms, or a substituted or unsubstituted heteroaryl group of 2 to 30 ring-forming carbon atoms. In Formula ET-1, $Ar_1$ to $Ar_3$ may each independently be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula ET-1, a to c may each independently be an integer from 0 to 10. In Formula ET-1, $L_1$ to $L_3$ may each independently be a direct linkage, a substituted or unsubstituted arylene group of 6 to 30 ring-forming carbon atoms, or a substituted or unsubstituted heteroarylene group of 2 to 30 ring-forming carbon atoms. In Formula ET-1, if a to c are 2 or more, $L_1$ to $L_3$ may each independently be a substituted or unsubstituted arylene group of 6 to 30 ring-forming carbon atoms, or a substituted or unsubstituted heteroarylene group of 2 to 30 ring-forming carbon atoms.

The electron transport region ETR may include an anthracene-based compound. However, embodiments are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris (3'-(pyridin-3-yl) biphenyl-3-yl)-1,3,5-triazine, 2-(4-(N-phenylbenzoimidazolyl-1-ylphenyl)-9,10-dinaphthylanthracene, 1,3,5-tri (1-phenyl-1H-benzo[d]imidazol-2-yl) benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N 1,O8)-(1,1'-biphenyl-4-olato)aluminum (BAlq), berylliumbis(benzoquinolin-10-olate ($Bebq_2$), 9,10-di(naphthalene-2-yl) anthracene (ADN), 1,3-bis[3,5-di(pyridin-3-yl)phenyl]benzene (BmPyPhB), and mixtures thereof, without limitation.

The electron transport region ETR may include at least one among Compounds ET1 to ET36 below.

ET1

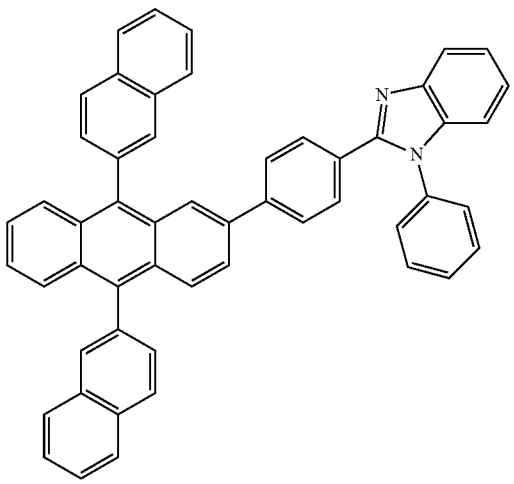

ET2

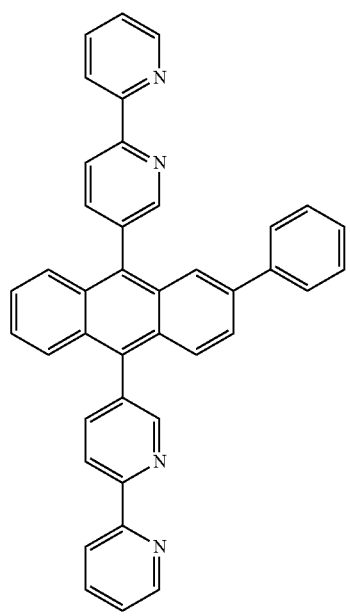

ET3

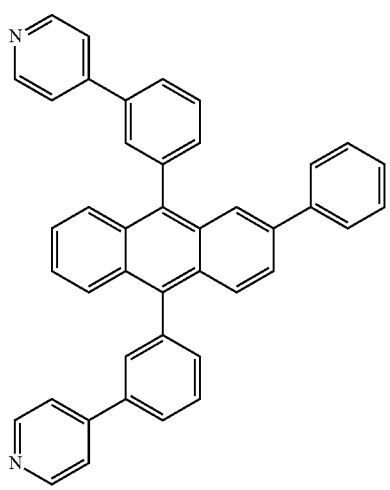

ET4
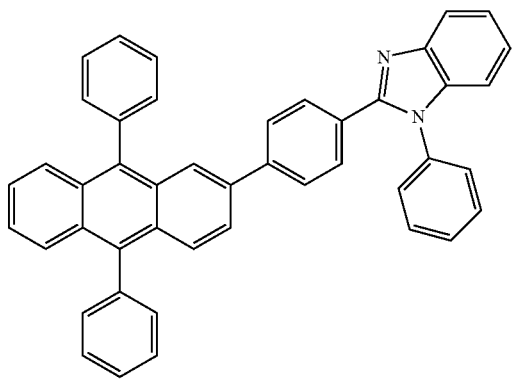
ET5
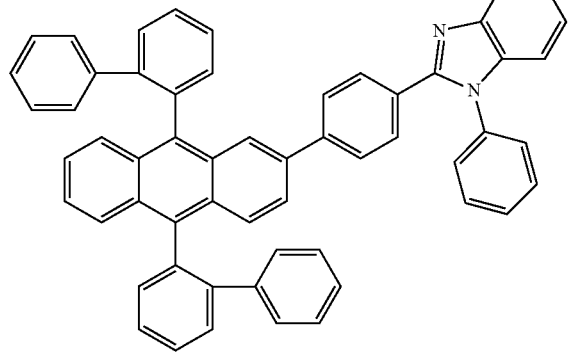
ET6
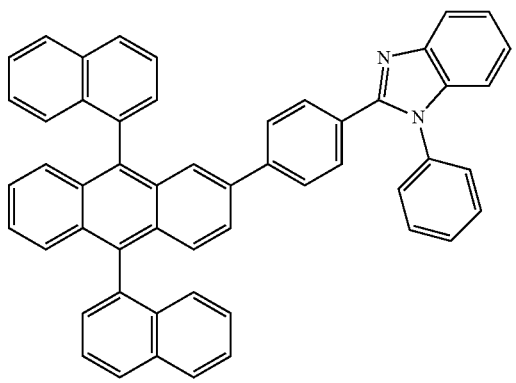
ET7
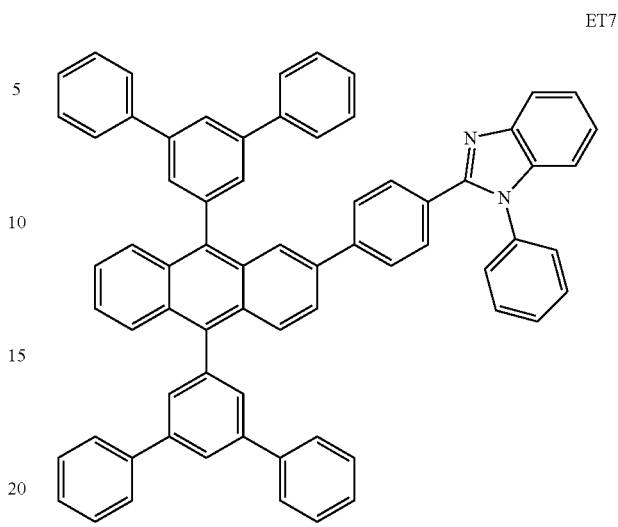
ET8
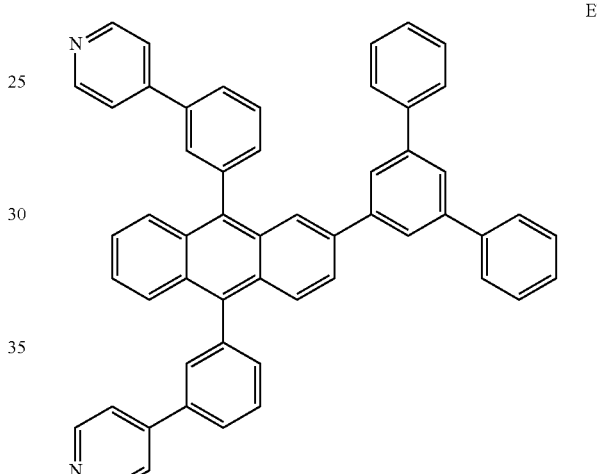
ET9
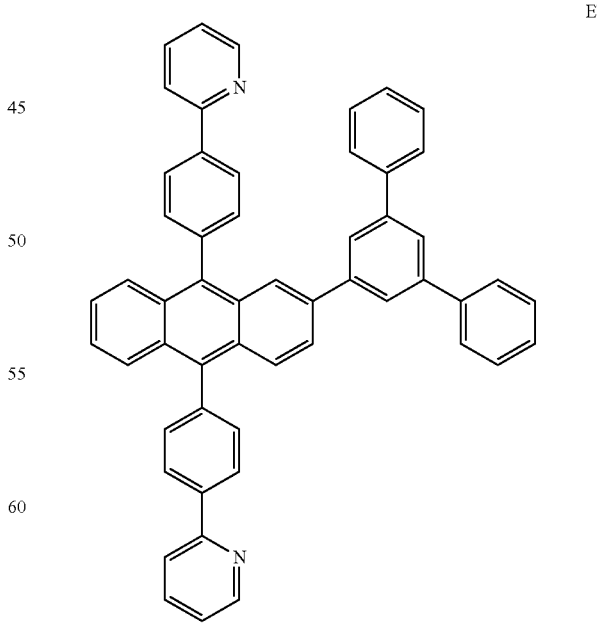

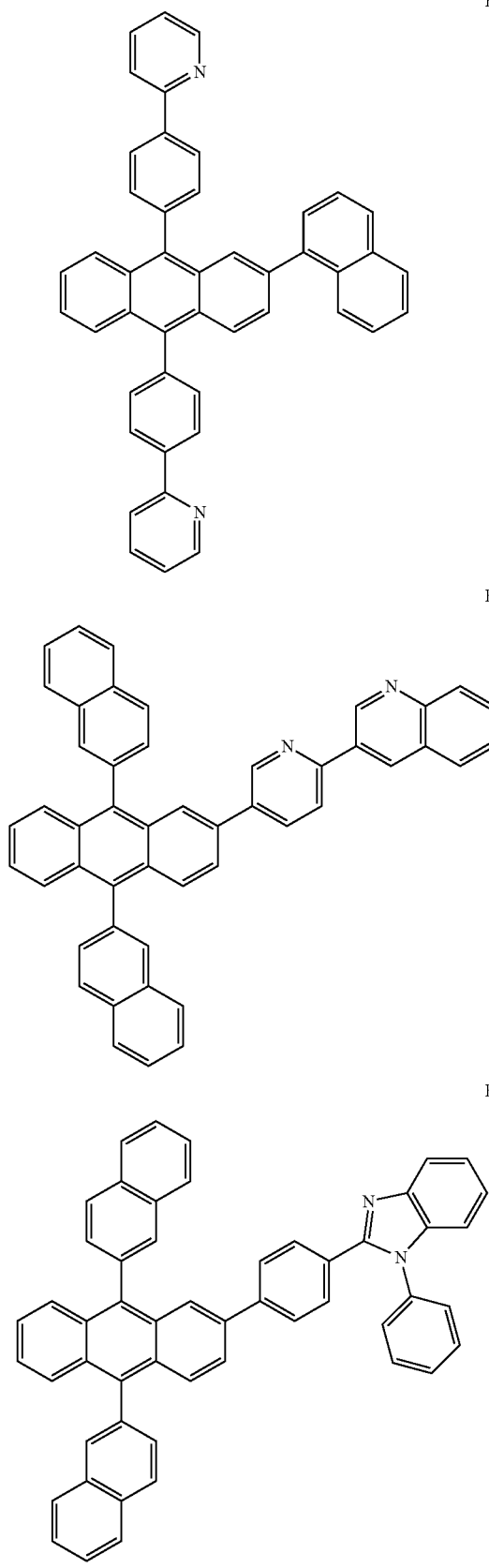
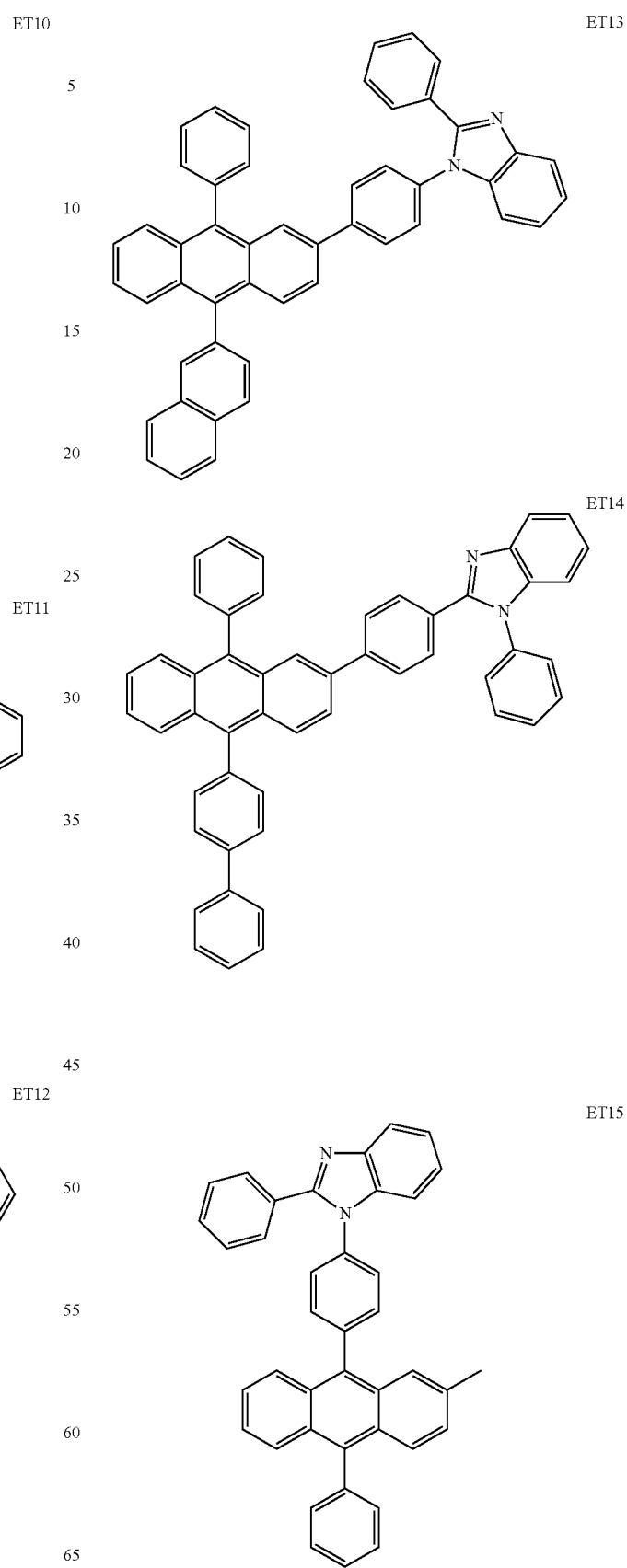

ET16
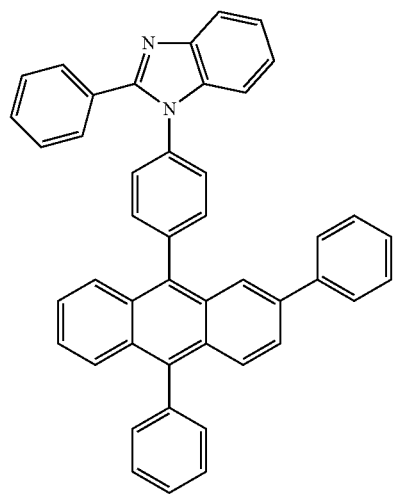
ET17
ET18
ET19
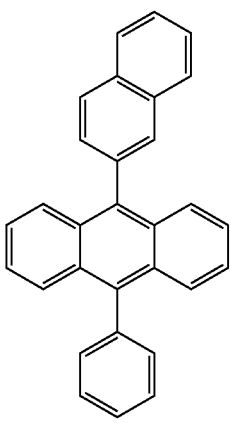
ET20
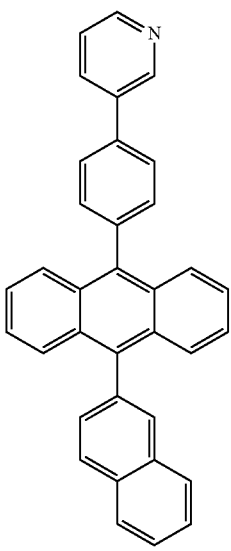
ET21
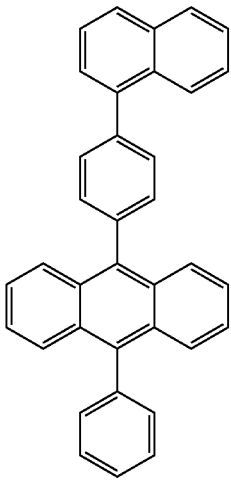

ET22
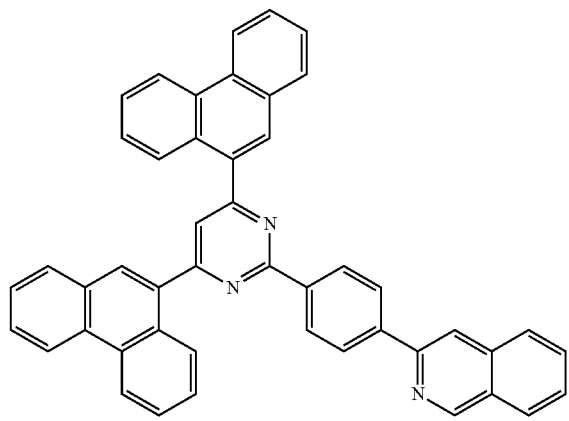
ET25
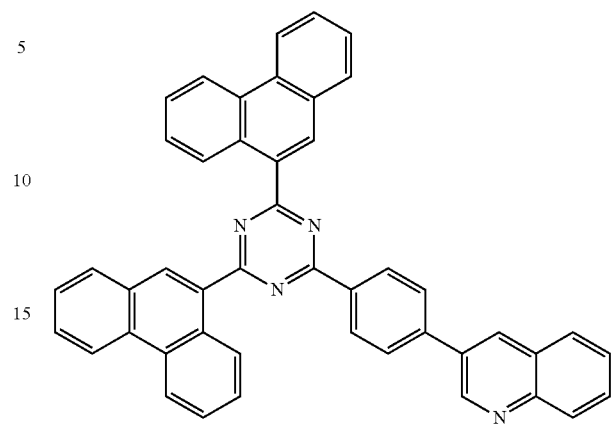
ET23
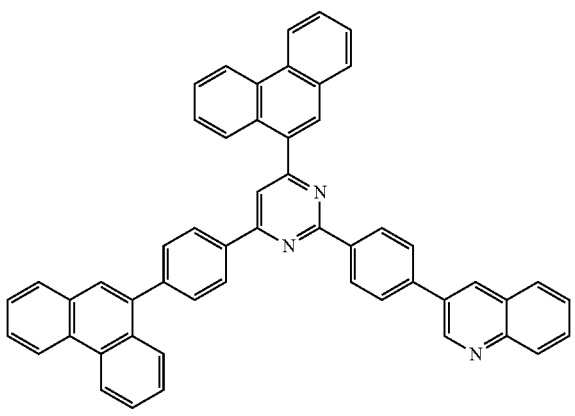
ET26
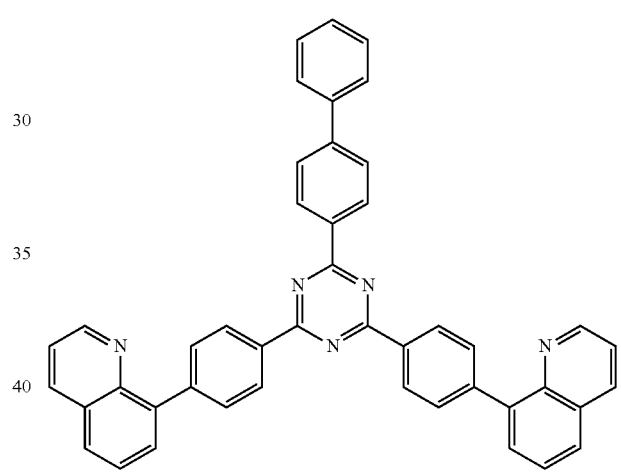
ET24
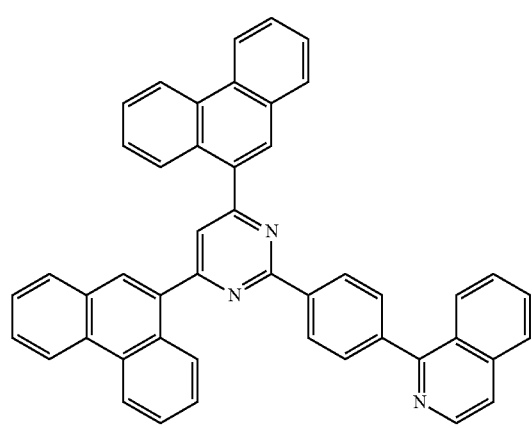
ET27
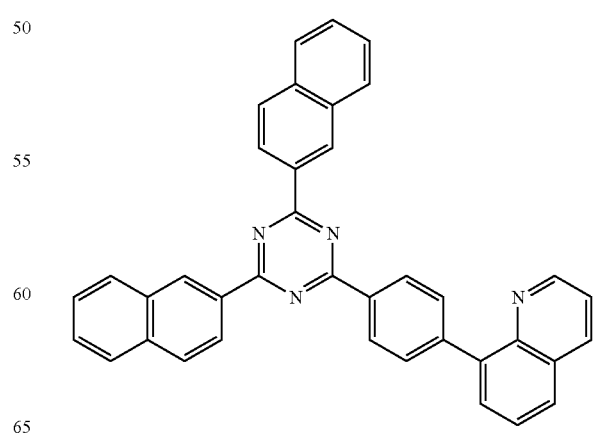

-continued
ET28
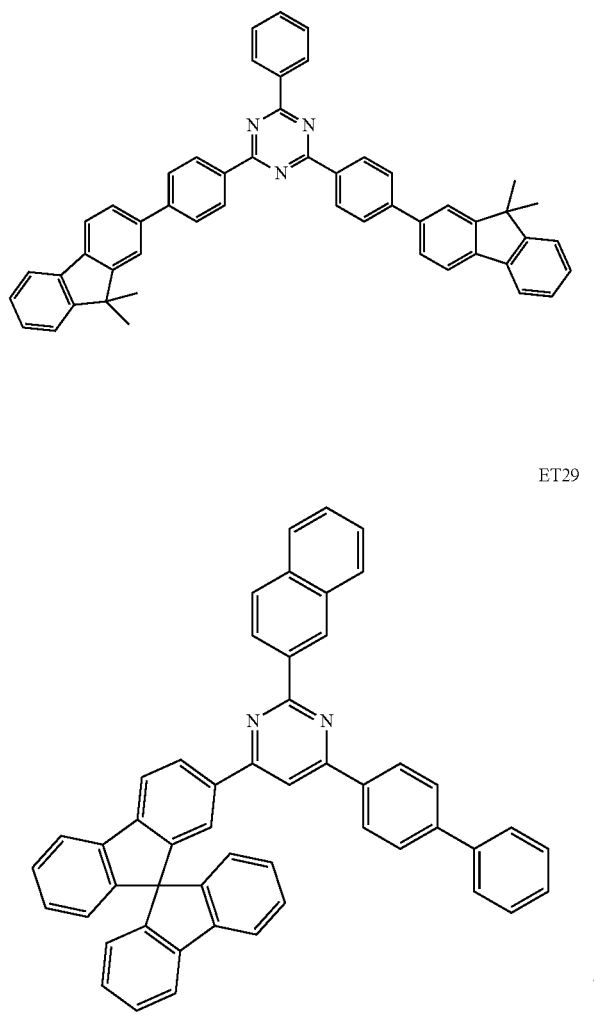
ET29
ET30
ET31
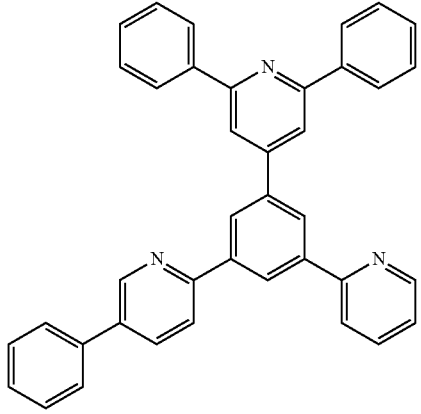
ET32
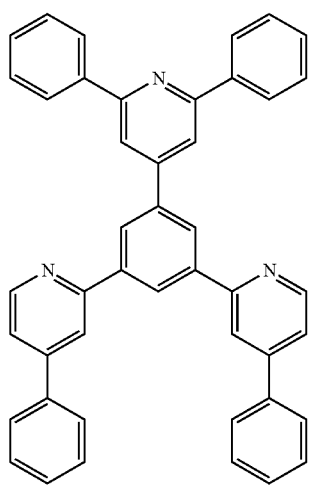
ET33
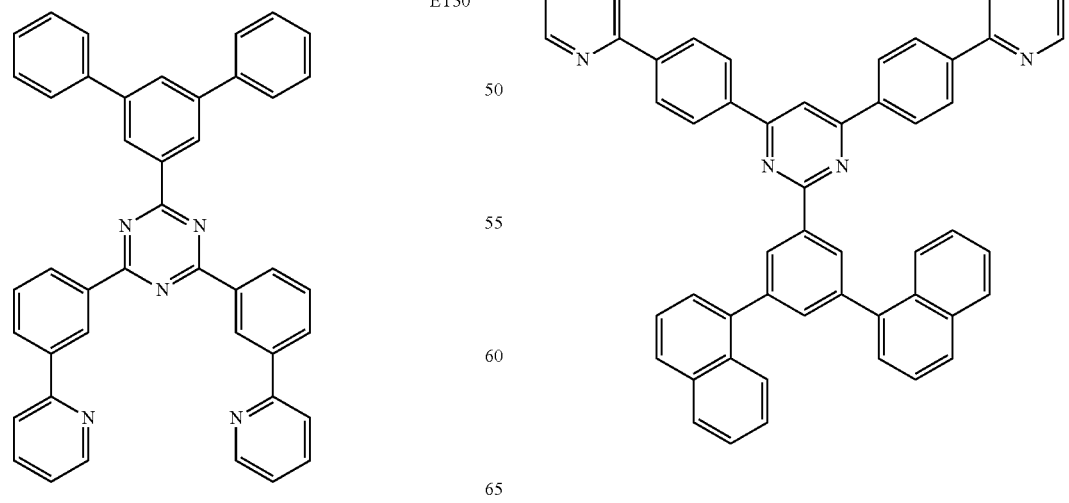

-continued

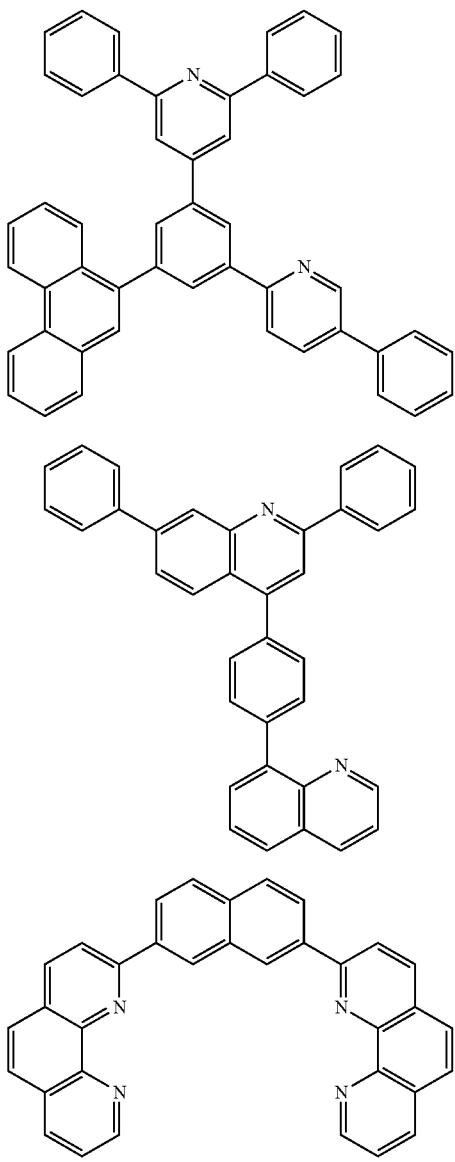

ET34

ET35

ET36

The electron transport region ETR may include a metal halide such as LiF, NaCl, CsF, RbCl, RbI, CuI and KI, a lanthanide such as Yb, or a co-depositing material of the metal halide and the lanthanide. For example, the electron transport region ETR may include KI:Yb, RbI:Yb, etc., as a co-depositing material. The electron transport region ETR may include a metal oxide such as $Li_2O$ and BaO, or 8-hydroxy-lithium quinolate (Liq). However, embodiments are not limited thereto. The electron transport region ETR also may be formed using a mixture material of an electron transport material and an insulating organo metal salt. The organo metal salt may be a material having an energy band gap equal to or greater than about 4 eV. For example, the organo metal salt may include metal acetates, metal benzoates, metal acetoacetates, metal acetylacetonates, or metal stearates.

The electron transport region ETR may include at least one of 2,9-dimethyl-4,7-diphenyl-1,10-phenanthroline (BCP), and 4,7-diphenyl-1,10-phenanthroline (Bphen) in addition to the aforementioned materials. However, embodiments are not limited thereto.

The electron transport region ETR may include the compounds of the electron transport region in at least one of an electron injection layer EIL, an electron transport layer ETL, and a hole blocking layer HBL.

If the electron transport region ETR includes an electron transport layer ETL, a thickness of the electron transport layer ETL may be in a range of about 100 Å to about 1,000 Å. For example, the thickness of the electron transport layer ETL may be in a range of about 150 Å to about 500 Å. If the thickness of the electron transport layer ETL satisfies the above-described range, satisfactory electron transport properties may be obtained without substantial increase of a driving voltage. If the electron transport region ETR includes an electron injection layer EIL, a thickness of the electron injection layer EIL may be in a range of about 1 Å to about 100 Å. For example, the thickness of the electron injection layer EIL may be in a range of about 3 Å to about 90 Å. If the thickness of the electron injection layer EIL satisfies the above described range, satisfactory electron injection properties may be obtained without inducing substantial increase of a driving voltage.

The second electrode EL2 is provided on the electron transport region ETR. The second electrode EL2 may be a common electrode. The second electrode EL2 may be a cathode or an anode, but embodiments are not limited thereto. For example, if the first electrode EL1 is an anode, the second cathode EL2 may be a cathode, and if the first electrode EL1 is a cathode, the second electrode EL2 may be an anode.

The second electrode EL2 may be a transmissive electrode, a transflective electrode, or a reflective electrode. If the second electrode EL2 is a transmissive electrode, the second electrode EL2 may include a transparent metal oxide, for example, ITO, IZO, ZnO, ITZO, etc.

If the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, W, In, Zn, Sn, compounds thereof, or mixtures thereof (for example, AgMg, AgYb, or MgAg). In another embodiment, the second electrode EL2 may have a multilayered structure including a reflective layer or a transflective layer formed using the above-described materials and a transparent conductive layer formed using ITO, IZO, ZnO, ITZO, etc. For example, the second electrode EL2 may include the aforementioned metal materials, combinations of two or more metal materials selected from the aforementioned metal materials, or oxides of the aforementioned metal materials.

Although not shown, the second electrode EL2 may be electrically connected to an auxiliary electrode. If the second electrode EL2 is electrically connected to the auxiliary electrode, the resistance of the second electrode EL2 may decrease.

In an embodiment, the light emitting device ED may further include a capping layer CPL disposed on the second electrode EL2. The capping layer CPL may include a multilayer or a single layer.

In an embodiment, the capping layer CPL may include an organic layer or an inorganic layer. For example, if the capping layer CPL includes an inorganic material, the inorganic material may include an alkali metal compound such as LiF, an alkaline earth metal compound such as $MgF_2$, SiON, SiNx, SiOy, etc.

For example, if the capping layer CPL includes an organic material, the organic material may include α-NPD, NPB, TPD, m-MTDATA, $Alq_3$, CuPc, $N^4,N^4,N^{4'},N^{4'}$-tetra(biphenyl-4-yl) biphenyl-4,4'-diamine (TPD15), 4,4',4''-tris(carbazol sol-9-yl)triphenylamine (TCTA), etc., or may include an epoxy resin, or acrylate such as methacrylate. A capping layer CPL may include at least one among Compounds P1 to P5 below, but embodiments are not limited thereto.

P1
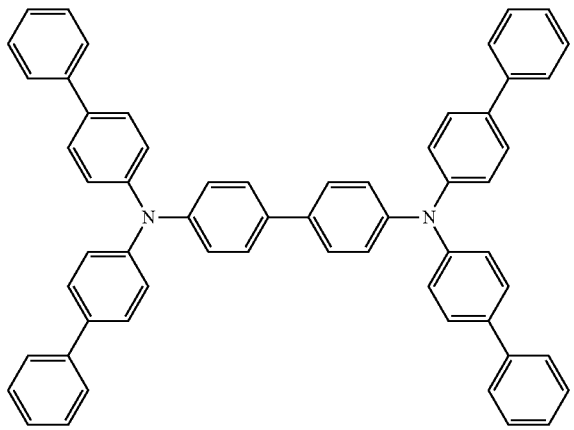

P2
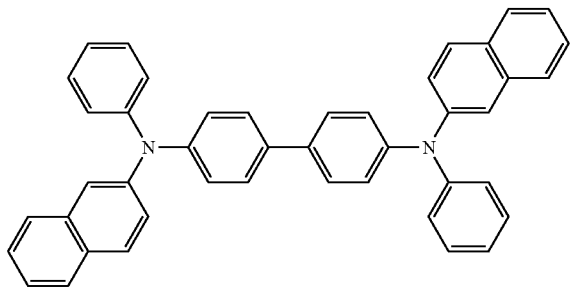

P3
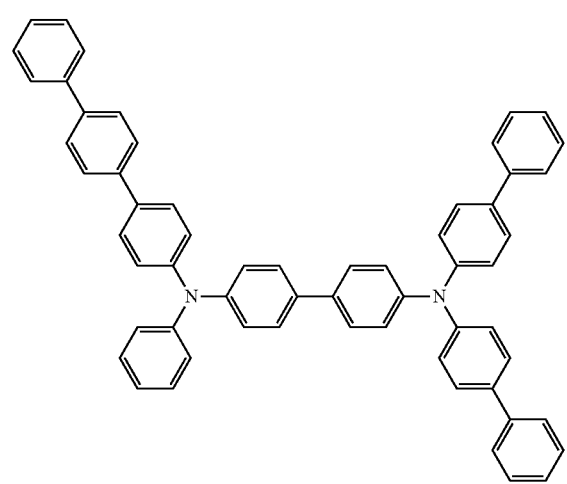

P4
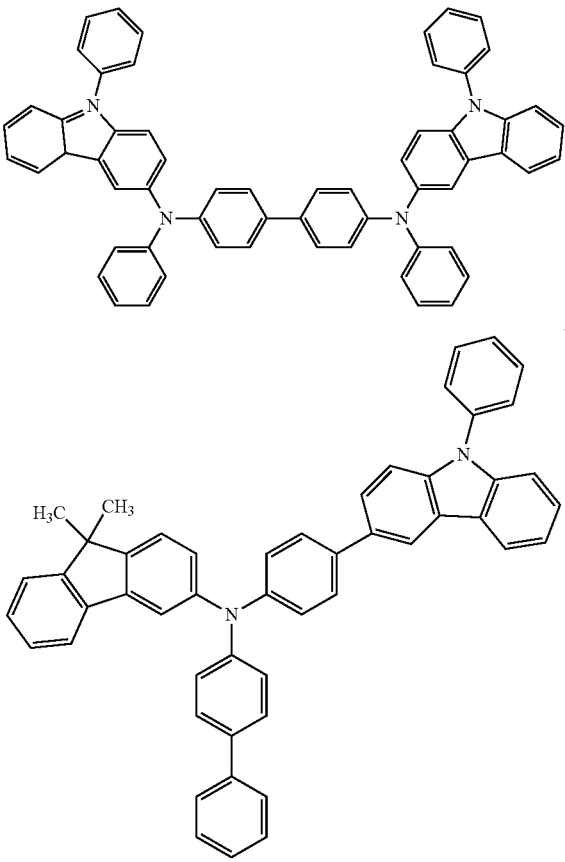

A refractive index of the capping layer CPL may be equal to or greater than about 1.6. For example, a refractive index of the capping layer CPL with respect to light in a wavelength range of about 550 nm to about 660 nm may be equal to or greater than about 1.6.

Figure 7:
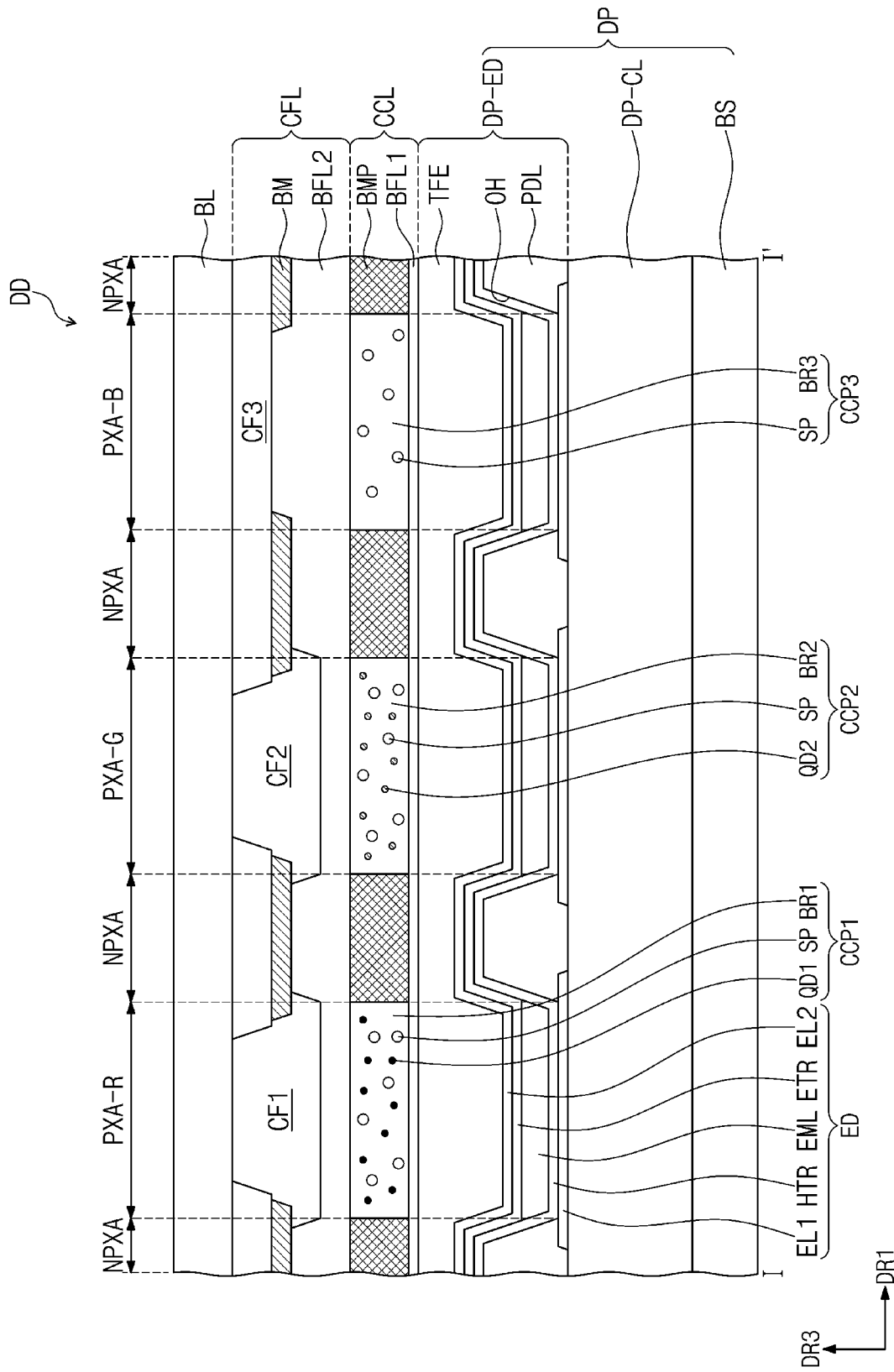
FIG. 7 and FIG. 8 are each schematic cross-sectional views on display apparatuses according to embodiments.
Figure 8:
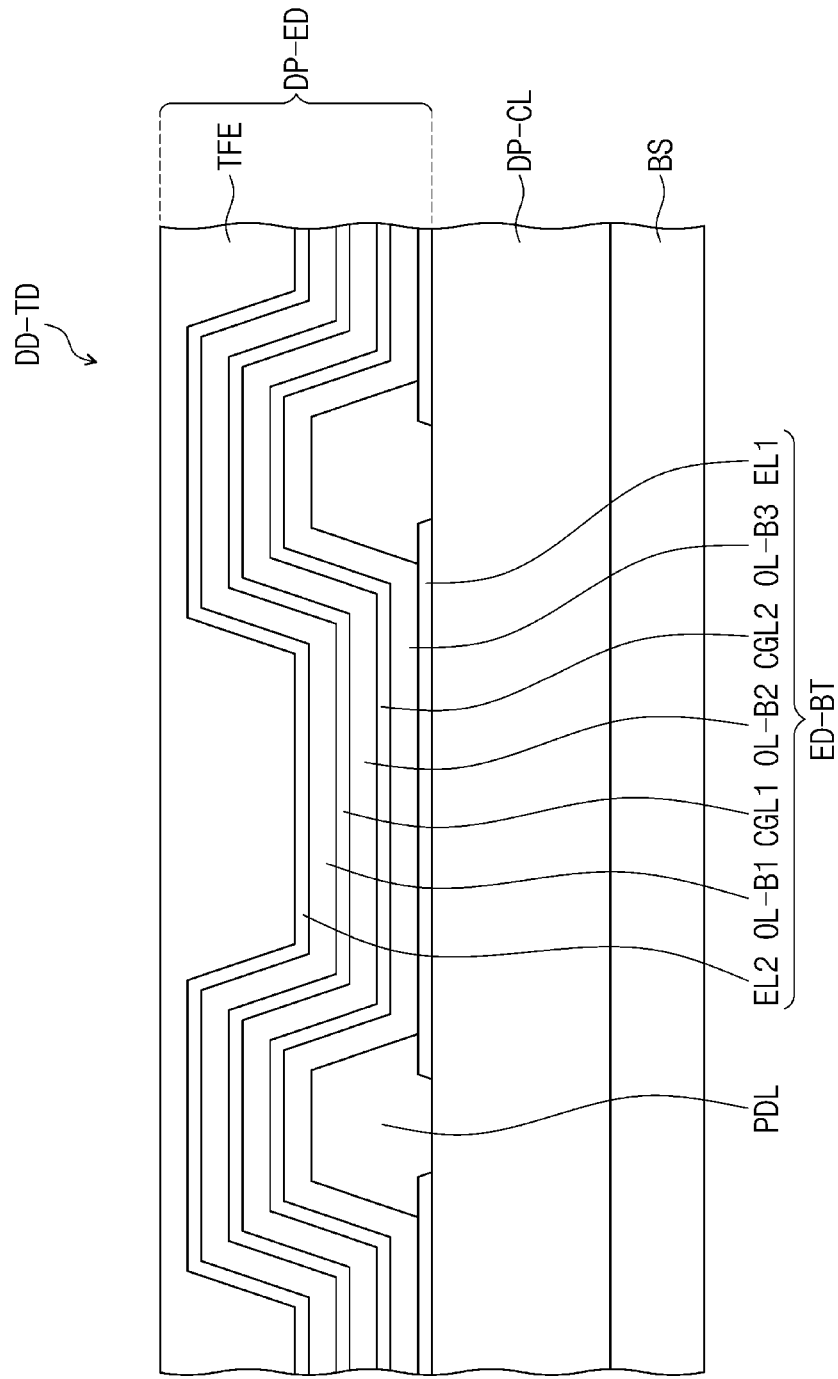

FIG. 7 and FIG. 8 are each a schematic cross-sectional view of display apparatuses according to embodiments. In the explanation on the display apparatuses of embodiments, referring to FIG. 7 and FIG. 8, the parts which overlap with the explanation on FIG. 1 to FIG. 6 will not be explained again, and the differing features will be explained.

Referring to FIG. 7, the display apparatus DD according to an embodiment may include a display panel DP including a display device layer DP-ED, a light controlling layer CCL disposed on the display panel DP and a color filter layer CFL.

In an embodiment shown in FIG. 7, the display panel DP includes a base layer BS, a circuit layer DP-CL provided on the base layer BS, and a display device layer DP-ED, and the display device layer DP-ED may include a light emitting device ED.

The light emitting device ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. The same descriptions of the light emitting devices of FIG. 3 to FIG. 6 may be applied to the structure of the light emitting device ED shown in FIG. 7.

Referring to FIG. 7, the emission layer EML may be disposed in an opening portion OH defined in a pixel definition layer PDL. For example, the emission layer EML divided by the pixel definition layer PDL and correspondingly provided to each of luminous areas PXA-R, PXA-G, and PXA-B may emit light in a same wavelength region. In the display apparatus DD of an embodiment, the emission layer EML may emit blue light. Although not shown in the drawings, in an embodiment, the emission layer EML may be provided as a common layer for all luminous areas PXA-R, PXA-G, and PXA-B.

The light controlling layer CCL may be disposed on the display panel DP. The light controlling layer CCL may include a light converter. The light converter may include a quantum dot or a phosphor. The light converter may convert the wavelength of provided light and emit the converted light. For example, the light controlling layer CCL may be a layer including a quantum dot or a layer including a phosphor.

The light controlling layer CCL may include light controlling parts CCP1, CCP2, and CCP3. The light controlling parts CCP1, CCP2, and CCP3 may be separated from one another.

Referring to FIG. 7, a partition pattern BMP may be disposed between the separated light controlling parts CCP1, CCP2, and CCP3, but embodiments are not limited thereto. In FIG. 8, the partition pattern BMP is shown not to be overlapped with the light controlling parts CCP1, CCP2, and CCP3, but at least a portion of the edge of the light controlling parts CCP1, CCP2, and CCP3 may overlap the partition pattern BMP.

The light controlling layer CCL may include a first light controlling part CCP1 including a first quantum dot QD1 converting first color light provided from the light emitting device ED into second color light, a second light controlling part CCP2 including a second quantum dot QD2 converting first color light into third color light, and a third light controlling part CCP3 transmitting first color light.

In an embodiment, the first light controlling part CCP1 may provide red light which is the second color light, and the second light controlling part CCP2 may provide green light which is the third color light. The third color controlling part CCP3 may transmit blue light which is the first color light provided from the light emitting device ED. For example, the first quantum dot QD1 may be a red quantum dot, and the second quantum dot QD2 may be a green quantum dot. The same description of quantum dots provided above may be applied to quantum dots QD1 and QD2.

The light controlling layer CCL may further include a scatterer SP. The first light controlling part CCP1 may include the first quantum dot QD1 and the scatterer SP, the second light controlling part CCP2 may include the second quantum dot QD2 and the scatterer SP, and the third light controlling part CCP3 may not include a quantum dot but may include the scatterer SP.

The scatterer SP may be an inorganic particle. For example, the scatterer SP may include at least one of $TiO_2$, ZnO, $Al_2O_3$, $SiO_2$, and hollow silica. The scatterer SP may include at least one of $TiO_2$, ZnO, $Al_2O_3$, $SiO_2$, and hollow silica, or may be a mixture of two or more materials selected among $TiO_2$, ZnO, $Al_2O_3$, $SiO_2$, and hollow silica.

Each of the first light controlling part CCP1, the second light controlling part CCP2, and the third light controlling part CCP3 may include base resins BR1, BR2, and BR3 in which the quantum dots QD1 and QD2 and the scatterer SP are dispersed. In an embodiment, the first light controlling part CCP1 may include the first quantum dot QD1 and the scatterer SP dispersed in the first base resin BR1, the second light controlling part CCP2 may include the second quantum dot QD2 and the scatterer SP dispersed in the second base resin BR2, and the third light controlling part CCP3 may include the scatterer particle SP dispersed in the third base resin BR3. The base resins BR1, BR2, and BR3 are mediums in which the quantum dots QD1 and QD2 and the scatterer SP may be dispersed, and may be composed of various resin compositions which may be generally referred to as a binder. For example, the base resins BR1, BR2, and BR3 may be acrylic resins, urethane-based resins, silicone-based resins, epoxy-based resins, etc. The base resins BR1, BR2, and BR3 may be transparent resins. In an embodiment, the first base resin BR1, the second base resin BR2, and the third base resin BR3 may be the same as or different from each other.

The light controlling layer CCL may include a barrier layer BFL1. The barrier layer BFL1 may prevent the penetration of moisture and/or oxygen (hereinafter, will be referred to as "humidity/oxygen"). The barrier layer BFL1 may be disposed on the light controlling parts CCP1, CCP2, and CCP3 to block the exposure of the light controlling parts CCP1, CCP2, and CCP3 to humidity/oxygen. The barrier layer BFL1 may cover the light controlling parts CCP1, CCP2, and CCP3. The barrier layer BFL2 may be provided between the light controlling parts CCP1, CCP2, and CCP3 and a color filter layer CFL.

The barrier layers BFL1 and BFL2 may include at least one inorganic layer. For example, the barrier layers BFL1 and BFL2 may be formed by including an inorganic material. For example, the barrier layers BFL1 and BFL2 may be formed by including silicon nitride, aluminum nitride, zirconium nitride, titanium nitride, hafnium nitride, tantalum nitride, silicon oxide, aluminum oxide, titanium oxide, tin oxide, cerium oxide and silicon oxynitride or a metal thin film securing light transmittance. The barrier layers BFL1 and BFL2 may each further include an organic layer. The barrier layers BFL1 and BFL2 may be composed of a single layer or of multiple layers.

In the display apparatus DD of an embodiment, the color filter layer CFL may be disposed on the light controlling layer CCL. For example, in an embodiment, the color filter layer CFL may be disposed directly on the light controlling layer CCL, and the barrier layer BFL2 may be omitted.

The color filter layer CFL may include a light blocking part BM and filters CF1, CF2, and CF3. The color filter layer CFL may include a first filter CF1 transmitting second color light, a second filter CF2 transmitting third color light, and a third filter CF3 transmitting first color light. For example, the first filter CF1 may be a red filter, the second filter CF2 may be a green filter, and the third filter CF3 may be a blue filter. Each of the filters CF1, CF2, and CF3 may include a polymer photosensitive resin and a pigment or dye. The first filter CF1 may include a red pigment or dye, the second filter CF2 may include a green pigment or dye, and the third filter CF3 may include a blue pigment or dye. However, embodiments are not limited thereto, and the third filter CF3 may not include a pigment or dye. The third filter CF3 may include a polymer photosensitive resin and not include a pigment or dye. The third filter CF3 may be transparent. The third filter CF3 may be formed using a transparent photosensitive resin.

In an embodiment, the first filter CF1 and the second filter CF2 may each be yellow filters. The first filter CF1 and the second filter CF2 may be provided in one body without distinction.

The light blocking part BM may be a black matrix. The light blocking part BM may be formed by including an organic light blocking material or an inorganic light blocking material including a black pigment or black dye. The light blocking part BM may prevent light leakage phenomenon and divide the boundaries among adjacent filters CF1, CF2, and CF3. In an embodiment, the light blocking part BM may be formed as a blue filter.

Each of the first to third filters CF1, CF2, and CF3 may be disposed corresponding to each of a red luminous area PXA-R, a green luminous area PXA-G, and a blue luminous area PXA-B.

An upper base layer BL may be disposed on the color filter layer CFL. The upper base layer BL may be a member providing a base surface on which the color filter layer CFL, the light controlling layer CCL, etc. are disposed. The upper base layer BL may be a glass substrate, a metal substrate, a plastic substrate, etc. However, embodiments are not limited thereto, and the upper base layer BL may include an inorganic layer, an organic layer, or a composite material layer. Although not shown in the drawing, the upper base layer BL may be omitted in an embodiment.

FIG. 8 is a schematic cross-sectional view showing a portion of the display apparatus according to an embodiment. In FIG. 8, the schematic cross-sectional view of a portion corresponding to the display panel DP in FIG. 7 is shown. In a display apparatus DD-TD of an embodiment, the light emitting device ED-BT may include multiple light emitting structures OL-B1, OL-B2, and OL-B3. The light emitting device ED-BT may include oppositely disposed first electrode EL1 and second electrode EL2, and the multiple light emitting structures OL-B1, OL-B2, and OL-B3 stacked in order in a thickness direction and provided between the first electrode EL1 and the second electrode EL2. Each of the light emitting structures OL-B1, OL-B2, and OL-B3 may include an emission layer EML (FIG. 7), a hole transport region HTR, and an electron transport region ETR, with the emission layer EML (FIG. 7) disposed therebetween.

For example, the light emitting device ED-BT included in the display apparatus DD-TD of an embodiment may be a light emitting device having a tandem structure and including multiple emission layers.

In an embodiment shown in FIG. 8, light emitted from the light emitting structures OL-B1, OL-B2, and OL-B3 may be all blue light. However, embodiments are not limited thereto, and the wavelength regions of light emitted from the light emitting structures OL-B1, OL-B2, and OL-B3 may be different from each other. For example, the light emitting device ED-BT including the multiple light emitting structures OL-B1, OL-B2, and OL-B3 emitting light in different wavelength regions may emit white light.

Charge generating layers CGL1 and CGL2 may be disposed between neighboring light emitting structures OL-B1, OL-B2, and OL-B3. The charge generating layers CGL1 and CGL2 may each include a p-type charge generating layer and/or an n-type charge generating layer.

The fused polycyclic compound of an embodiment includes a structure in which an additional fused structure is formed on a quinolinoacridinedione skeleton through an additional connecting group such as a direct linkage, an oxy group, a thio group, a carbonyl group, and an alkyl group. Since the fused polycyclic compound according to an embodiment has a wide conjugation structure represented by Formula 1, when the fused polycyclic compound of an embodiment is used as a material for a light emitting device, high efficiency of the light emitting device may be achieved.

Hereinafter, the fused polycyclic compound according to an embodiment and the light emitting device of an embodiment will be explained referring to the embodiments and the comparative embodiments. The embodiments below are only examples to assist the understanding of the disclosure, and the scope thereof is not limited thereto.

EXAMPLES

1. Synthesis of Fused Polycyclic Compound

The synthesis method of a fused polycyclic compound according to an embodiment will be explained by illustrating the synthesis methods of Compounds 4 and 6. The synthesis methods of the fused polycyclic compounds explained hereinafter are embodiments, and the synthesis method of the fused polycyclic compound according to an embodiment is not limited to the embodiments below.

(1) Synthesis of Compound 4

Fused Polycyclic Compound 4 according to an embodiment may be synthesized, for example, by the reactions below.

Synthesis of Intermediate Compound 4a

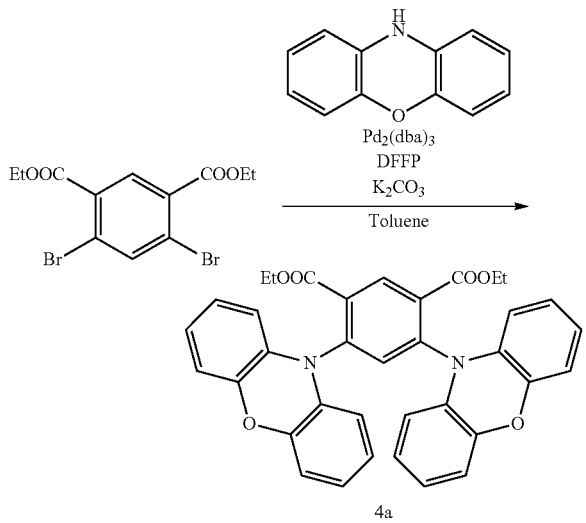

Diethyl-4,6-dibromoisophthalate (2.7 g, 7.0 mmol), 10H-phenoxazine (3.2 g, 17.5 mmol), $K_2CO_3$ (dissolved in dry toluene (30 mL), 3.2 g, 23.1 mmol), $Pd_2(dba)_3$ (0.096 g, 0.105 mmol) and DFFP (0.12 g, 0.21 mmol) were refluxed under a $N_2$ atmosphere for about 72 hours. After cooling to room temperature, a mixture obtained was diluted with chloroform and filtered through a celite pad. A collected organic layer was extracted with water and dried with anhydrous $Na_2SO_4$. After filtering and evaporating, the crude product was separated by silica gel column chromatography (eluent: hexane/$CH_2Cl_2$/ethyl acetate=17:2:1) to obtain Intermediate Compound 4a (diethyl-4,6-di(10H-phenoxazine-10-yl) isophthalate as an orange solid (yield=2.6 g, 63%). $^1$H-NMR measurement results and MS measurement results are as follows. Through this, the orange solid compound was identified as Intermediate Compound 4a.

$^1$H-NMR (400 MHZ, DMSO-d6): δ 8.73 (s, 1H), 7.91 (s, 1H), 6.73-6.76 (m, 4H), 6.65-6.71 (m, 8H), 5.99-6.03 (m, 4H), 4.13 (q, J=7.1 Hz, 4H), 1.01 (t, J=7.2 Hz, 6H).

MS (ESI): m/z, calcd: 584.19 [M] +; found: 584.10.

Synthesis of Compound 4

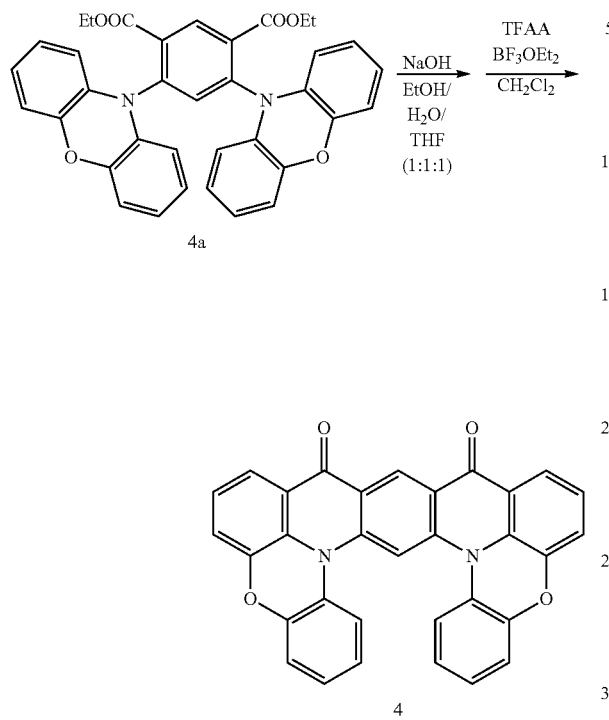

A suspension of Intermediate Compound 4a (2.6 g, 4.4 mmol) in an aqueous solution (30 mL) of ethanol (30 mL), THF (30 mL) and NaOH (1.8 g, 44 mmol) was refluxed for about 36 hours. After cooling to room temperature, the produced solution was evaporated under a reduced pressure to remove THF, and HCl (6 M) was added thereto until pH reached 1-2 for acidification. The precipitate was filtered and washed with water and hexane. The powder thus obtained was dried in vacuum over about 3 hours at about 60° C. to obtain a diacid powder (2.3 g), and this diacid powder was used in a next step without additional separation. The diacid powder was dispersed in $CH_2Cl_2$ (100 mL) under a $N_2$ atmosphere. To the reaction mixture, trifluoroacetic anhydride (2.8 g, 13.2 mmol) was added at room temperature, and the reaction mixture was stirred at the same temperature for about 0.5 hours further. The mixture was cooled to about 0° C., and boron trifluoride diethyl etherate (0.6 mL, 4.4 mmol) was added, and the reaction mixture was reacted at the same temperature for about 1 hour and at room temperature for about 48 hours further. The mixture thus produced was poured into a $NaHCO_3$ aqueous solution and stirred for about 0.5 hours. After filtering, the crude powder was washed with water, methanol, and hexane. After drying for about 3 hours in vacuum at about 60° C., the crude product was separated by temperature gradient sublimation in vacuum (340° C., $1.0 \times 10^{-3}$ Pa) to obtain Compound 4 as a yellow solid (yield=0.65 g, 30%). MS measurement results are as follows. Through this, the yellow solid compound was identified as Compound 4.

MS (ESI): m/z, calcd: 492.11 [M] +; found: 492.63.

(2) Synthesis of Compound 6

Fused Polycyclic Compound 6 of an embodiment may be synthesized, for example, by the reactions below.

Synthesis of Intermediate Compound 6a

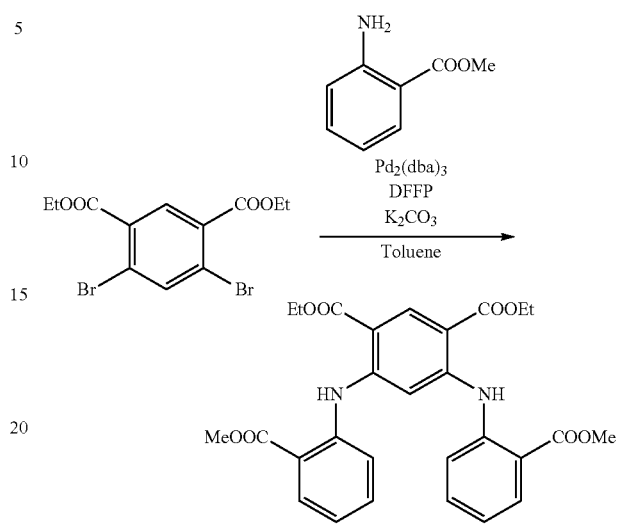

A mixture of diethyl-4,6-dibromoisophthalate (3.8 g, 10 mmol), methyl-2-aminobenzoate (3.8 g, 25 mmol), $K_2CO_3$ (dissolved in dry toluene (20 mL), 4.6 g, 33 mmol), $Pd_2(dba)_3$ (0.14 g, 0.15 mmol) and DFFP (0.17 g, 0.3 mmol) was refluxed under a $N_2$ atmosphere for about 48 hours. After cooling to room temperature, a mixture obtained was diluted with chloroform and filtered through a celite pad. A collected organic layer was extracted with water and dried with anhydrous $Na_2SO_4$. After filtering and evaporating, the crude product was separated by silica gel column chromatography (eluent: hexane/ethyl acetate=4:1) to obtain Intermediate Compound 6a (diethyl-4,6-bis((2-(methoxycarbonyl)phenyl)amino) isophthalate) as a white solid (yield=3.2 g, 48%). $^1$H-NMR measurement results and MS measurement results are as follows. Through this, the white solid compound was identified as Intermediate Compound 6a.

$^1$H-NMR (400 MHZ, DMSO-d6): δ 7.76 (s, 1H), 7.52 (dd, J=7.7, 1.1 Hz, 2H), 7.49 (dd, J=7.8, 2.0 Hz, 2H), 7.21 (td, J=7.6, 1.0 Hz, 2H), 7.10-7.16 (m, 6H), 6.88-6.92 (m, 2H), 6.69 (d, J=7.3 Hz, 4H), 6.56 (s, 1H), 3.69 (q, J=7.1 Hz, 4H), 3.32 (s, 6H), 0.95 (t, J=7.2 Hz, 6H).

MS (ESI): m/z, calcd: 520.18 [M] +; found: 521.47.

Synthesis of Intermediate Compound 6b

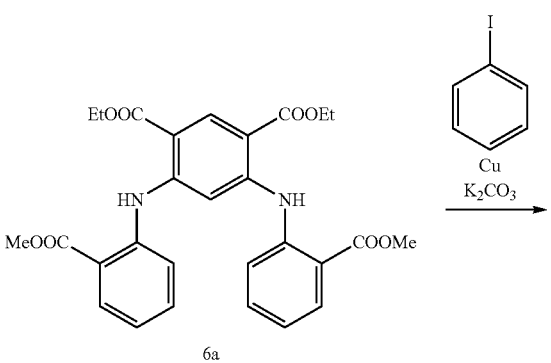

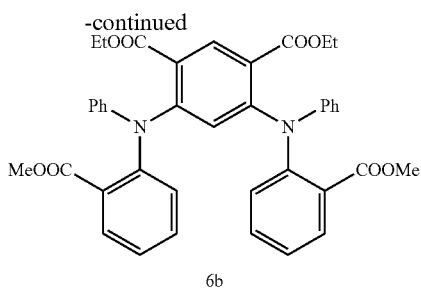

6b

Intermediate Compound 6a (3.2 g, 6.1 mmol), K₂CO₃ (2.6 g, 18.3 mmol) and a Cu powder (dissolved in iodobenzene (15 mL), 0.18 g, 2.8 mmol) were stirred under a $N_2$ atmosphere at about 200° C. for about 72 hours. After cooling to room temperature, a large amount of aqueous NH₄Cl and CH₂Cl₂ were added to the reaction mixture. A collected organic layer was extracted and dried with anhydrous Na₂SO₄. After filtering and evaporating, the crude product was separated by silica gel column chromatography (eluent: hexane/ethyl acetate=6:1) and recrystallized at a low temperature from a hexane/ethyl acetate solution to obtain Intermediate Compound 6b (diethyl-4,6-bis((2-(methoxycarbonyl)phenyl) (phenyl)amino) isophthalate) as a lemon yellow solid (yield=3.8 g, 93%). ¹H-NMR measurement results and MS measurement results are as follows. Through this, the lemon yellow solid compound was identified as Intermediate Compound 6b.

¹H-NMR (400 MHZ, DMSO-d6): δ 7.76 (s, 1H), 7.52 (dd, J=7.7, 1.1 Hz, 2H), 7.48 (dd, J=7.8, 2.0 Hz, 2H), 7.20 (td, J=7.6, 1.0 Hz, 2H), 7.09-7.16 (m, 6H), 6.87-6.91 (m, 2H), 6.69 (d, J=7.3 Hz, 4H), 6.55 (s, 1H), 3.68 (q, J=7.1 Hz, 4H), 3.31 (s, 6H), 0.94 (t, J=7.2 Hz, 6H).

MS (ESI): m/z, calcd: 672.25 [M] +; found: 672.80.

Synthesis of Compound 6

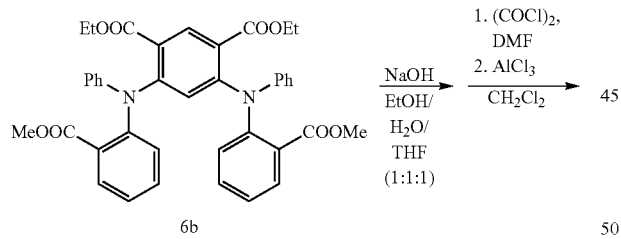

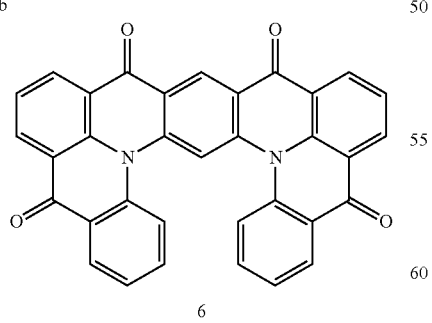

6

A suspension of Intermediate Compound 6b (1.5 g, 2.2 mmol) in an aqueous solution (20 mL) of ethanol (20 mL), THF (20 mL) and NaOH (1.8 g, 44 mmol) was refluxed for about 24 hours. After cooling to room temperature, the produced mixture was evaporated under a reduced pressure to remove THE, and HCl (6 M) was added thereto until pH reached 1-2 for acidification. The precipitate was filtered and washed with water and hexane. The powder thus obtained was dried in vacuum over about 3 hours at about 60° C. to obtain a diacid powder (1.2 g), and this diacid powder was used in a next step without additional separation. The diacid powder was dispersed in CH₂Cl₂ (30 mL) under a $N_2$ atmosphere. To the reaction mixture, oxalyl chloride (0.7 mL, 8.0 mmol) and four drops of DMF were added in order. After refluxing for about 3 hours, the reaction mixture was cooled to room temperature. Under a positive stream of $N^2$, AlCl₃ (5.3 g, 40 mmol) was slowly added. After refluxing for about 24 hours, the reaction mixture was cooled to room temperature and quenched with a large amount of water. The precipitate was filtered and washed with water, methanol, and hexane. After drying for about 3 hours in vacuum at about 60° C., the crude product was separated by temperature gradient sublimation in vacuum (350° C., 1.0×10⁻³ Pa) to obtain Compound 6 as a yellow solid (yield=0.15 g, 13%). MS measurement results are as follows. Through this, the yellow solid compound was identified as Compound 6.

MS (ESI): m/z, calcd: 516.11 [M] +; found: 517.01.

2. Manufacture and Evaluation of Light Emitting Device Including Fused Polycyclic Compound (Manufacture of Light Emitting Device)

The light emitting devices of Examples 1 and 2 were manufactured using Compound 4 and Compound 6 as dopant materials of an emission layer.

Example Compounds

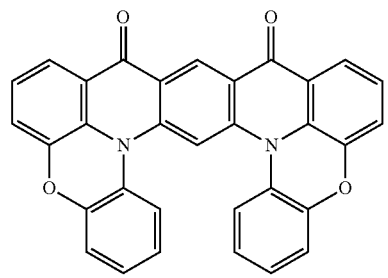

4

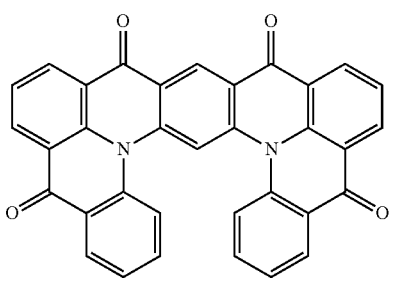

6

Comparative Compound X1 below was used for the manufacture of a device of the Comparative Example.

Comparative Compound

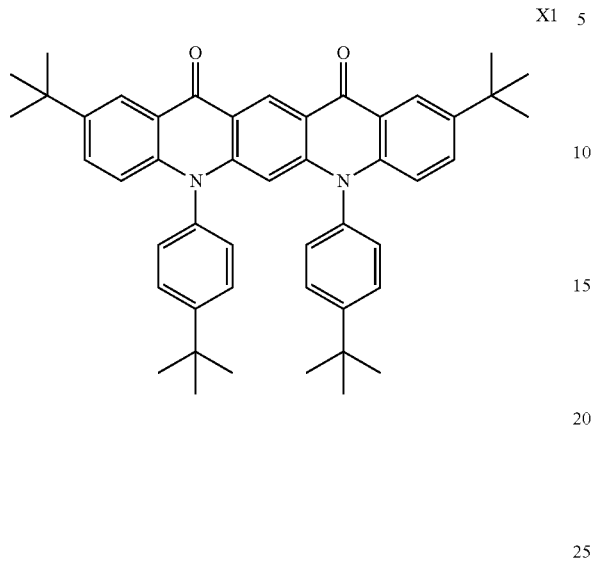

X1

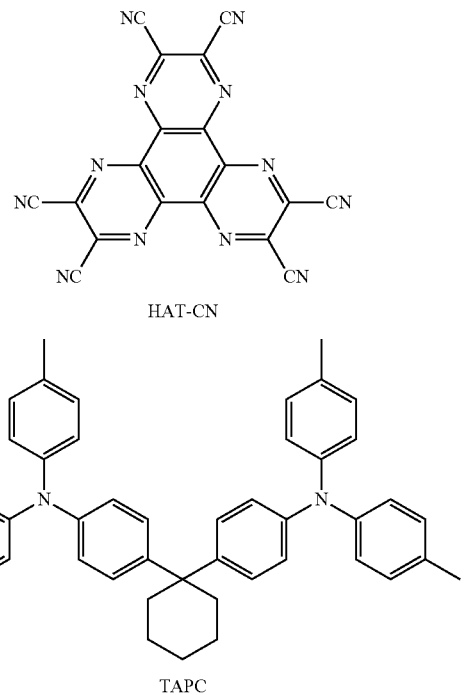

HAT-CN

TAPC

A light emitting device of an embodiment, including the fused polycyclic compound of an embodiment in an emission layer was manufactured by a method below. Example 1 and Example 2 correspond to light emitting devices manufactured by using Compound 4 and Compound 6, which are the Example Compounds, as light emitting materials. Comparative Example 1 corresponds to a light emitting device manufactured by using Comparative Compound $X_1$ as a light emitting material.

A first electrode with a thickness of about 50 nm was formed using ITO, a hole injection layer with a thickness of about 10 nm was formed using 1,4,5,8,9,11-hexaazatriphenylenehexacarbonitrile (HAT-CN), a first hole transport layer with a thickness of about 40 nm was formed using 1,1-bis[(di-4-tolylamino)phenyl]cyclohexane (TAPC), a second hole transport layer with a thickness of about 10 nm was formed using 9-phenyl-9H-3,9'-bicarbazole (CCP), an emission layer with a thickness of about 20 nm was formed using (9-phenyl-9H-carbazole-3,6-diyl)bis(diphenylphosphine oxide) (PPCz) doped with 3% of the Example Compound or the Comparative Compound, a first electron transport layer with a thickness of about 10 nm was formed using dibenzo[b,d]furan-2,8-diylbis(diphenylphosphine oxide) (PPF), a second electron transport layer with a thickness of about 50 nm was formed using 4,6-bis(3,5-di(pyridin-3-yl)phenyl)-2-methylpyrimidine (B3PyMPM), an electron injection layer with a thickness of about 1 nm was formed using Liq, and a second electrode with a thickness of about 100 nm was formed using Al. All layers were formed under a vacuum atmosphere by a deposition method.

The compounds used for the manufacture of the light emitting devices of the Examples and the Comparative Example are shown below. The materials are commercial materials, which were purified by sublimation and used for the manufacture of the devices.

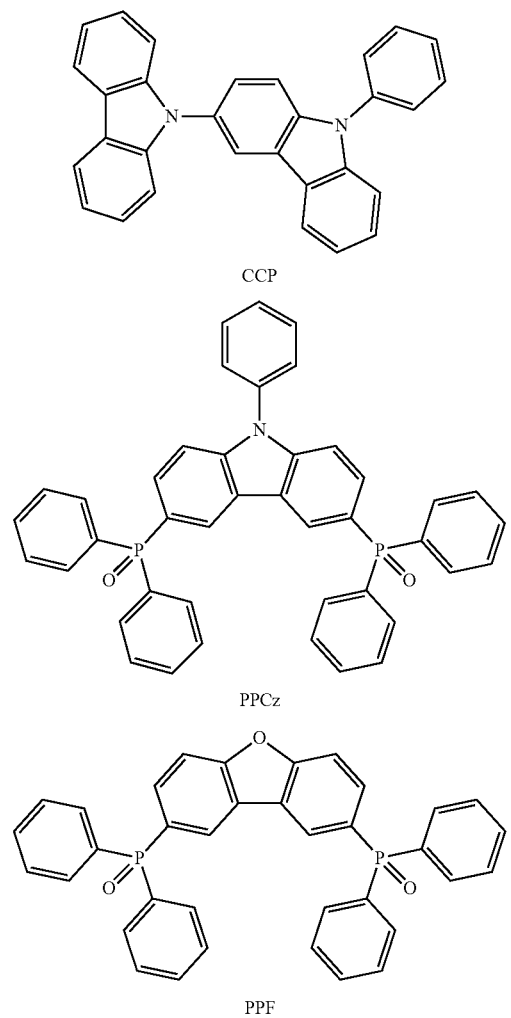

CCP

PPCz

PPF

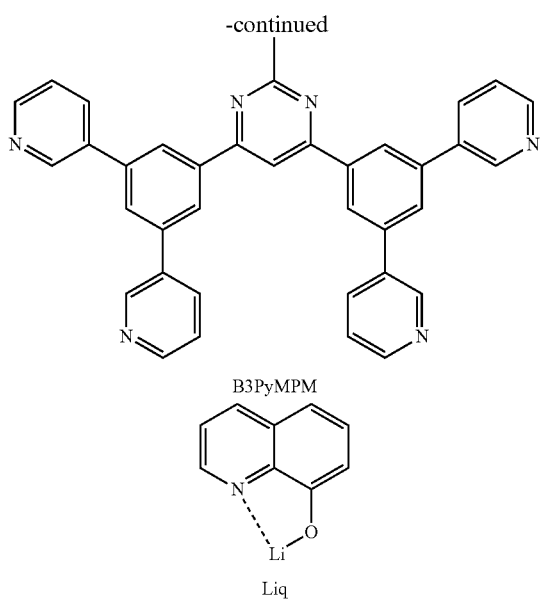

B3PyMPM

Liq

Experimental Examples

The device efficiencies of the light emitting devices manufactured using Compound 4, Compound 6, and Comparative Compound X1 were evaluated. Evaluation results are shown in Table 1 below. In the device evaluation, the maximum light emitting wavelength λmax, the maximum value of external quantum efficiency $EQE_{max}$, external quantum efficiency at about 100 cdm$^{-2}$ of $EQE_{100cdm^{-2}}$, and roll-off ratio were measured and shown.

TABLE 1

| Device manufacturing example | Dopant compound | $\lambda_{max}$ (nm) | $EQE_{max}$ (%) | $EQE_{100cdm^{-2}}$ (%) | Roll-off ratio (%) |
|---|---|---|---|---|---|
| Example 1 | Compound 4 | 515 | 18.6 | 11.1 | 40.3 |
| Example 2 | Compound 6 | 463 | 19.0 | 11.0 | 42.1 |
| Comparative Example 1 | Comparative Compound X1 | 455 | 17.1 | 1.20 | 93.0 |

Referring to the results of Table 1, it could be confirmed that the Examples of the light emitting device using the fused polycyclic compound according to an embodiment as a light emitting material showed improved emission efficiency and reduced roll-off ratio while maintaining the light emitting wavelength of blue light when compared with the Comparative Example.

In case of the Example Compounds, an additional fused structure through an additional connecting group such as a direct linkage, an oxy group, a thio group, a carbonyl group, and an alkyl group on a quinolinoacridinedione skeleton is included in a molecule, and a wide conjugation structure may be formed, the structure of a polycyclic aromatic ring may be stabilized, multi resonance effects may increase, and reverse intersystem crossing may be easily generated. Accordingly, if the Example Compound is used as a thermally activated delayed fluorescence dopant, full width at half maximum and a wavelength region are suitable as a blue light emitting material, and emission efficiency may be improved. The light emitting device of an embodiment includes the fused polycyclic compound of an embodiment as the dopant of a thermally activated delayed fluorescence (TADF) emitting device, and the external quantum efficiency value at about 100 cdm$^{-2}$ may be high as well as the maximum value of external quantum efficiency, and as a result, the roll-off ratio may be reduced.

Comparative Compound X-1 included in Comparative Example 1 has a quinolinoacridinedione structure but does not have an additional fused structure. Accordingly, it could be confirmed that emission efficiency was degraded when compared with the Examples, and the external quantum efficiency value at about 100 cdm$^{-2}$ was significantly reduced, and a roll-off ratio was high. Since the device of the Examples include the Example Compounds having short delayed fluorescence life length (Tau delay), a light emitting device with high efficiency, emitting light with high efficiency and low roll-off may be accomplished.

The light emitting device of an embodiment may show improved device properties of high efficiency.

The fused polycyclic compound of an embodiment may be included in the emission layer of a light emitting device, and may contribute to the increase of efficiency of an organic electroluminescence device.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the following claims.

What is claimed is:

1. A light emitting device, comprising:
   a first electrode;
   a second electrode facing the first electrode; and
   a plurality of organic layers disposed between the first electrode and the second electrode, wherein
   at least one organic layer among the plurality of organic layers comprises a fused polycyclic compound, and
   the fused polycyclic compound is represented by Formula 1:

[Formula 1]

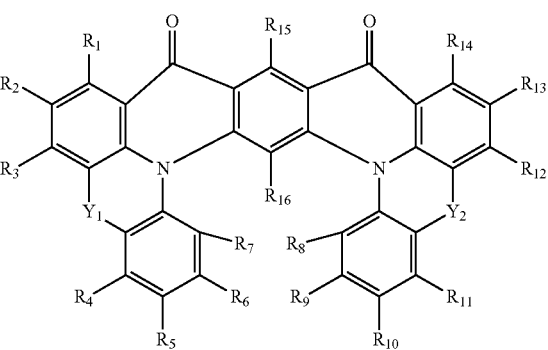

wherein in Formula 1,

Y₁ and Y₂ are each independently a direct linkage, —O—, —S—, or —C(R₁₇) (R₁₈)—,

R₁ to R₁₈ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms.

2. The light emitting device of claim 1, wherein the plurality of organic layers comprise:
a hole transport region disposed on the first electrode;
an emission layer disposed on the hole transport region; and
an electron transport region disposed on the emission layer, and
the emission layer comprises the fused polycyclic compound.

3. The light emitting device of claim 2, wherein the emission layer emits delayed fluorescence.

4. The light emitting device of claim 2, wherein
the emission layer is a delayed fluorescence emission layer comprising a host and a dopant, and
the dopant comprises the fused polycyclic compound represented by Formula 1.

5. The light emitting device of claim 2, wherein the emission layer emits light having a central wavelength in a range of about 430 nm to about 530 nm.

6. The light emitting device of claim 1, wherein in Formula 1, Y₁ and Y₂ are the same.

7. The light emitting device of claim 1, wherein in Formula 1,
R₁ and R₁₄ are the same,
R₂ and R₁₃ are the same,
R₃ and R₁₂ are the same,
R₄ and R₁₁ are the same,
R₅ and R₁₀ are the same,
R₆ and R₉ are the same, and
R₇ and R₈ are the same.

8. The light emitting device of claim 1, wherein the fused polycyclic compound represented by Formula 1 is represented by Formula 2-1, Formula 2-2, Formula 2-3, or Formula 2-5:

[Formula 2-1]

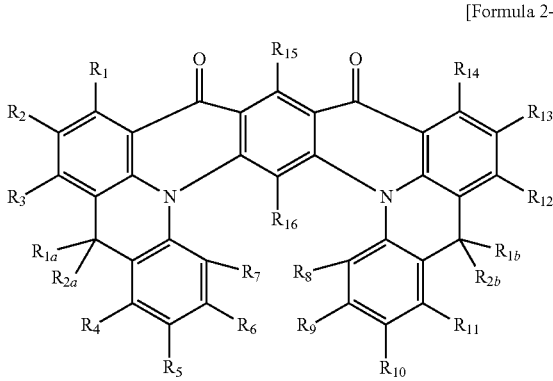

[Formula 2-2]

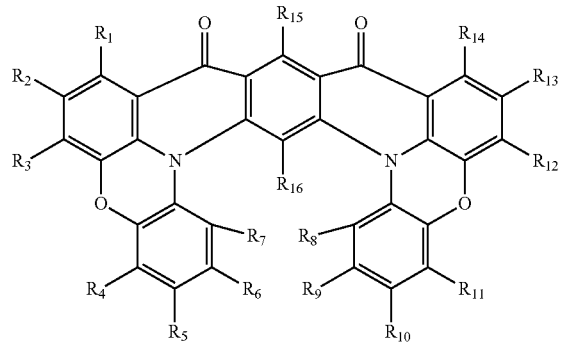

[Formula 2-3]

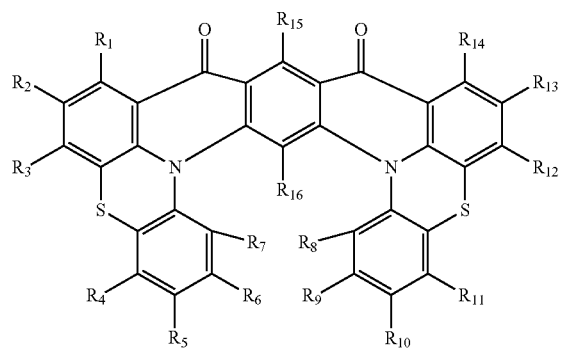

[Formula 2-4]

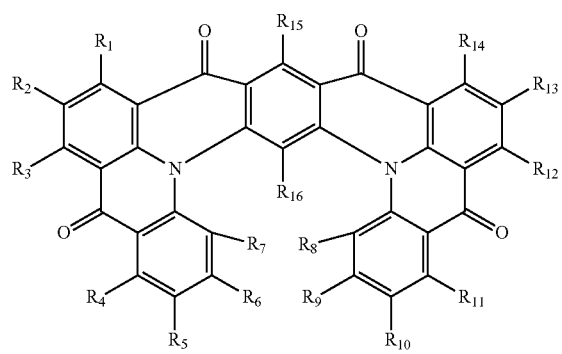

[Formula 2-5]

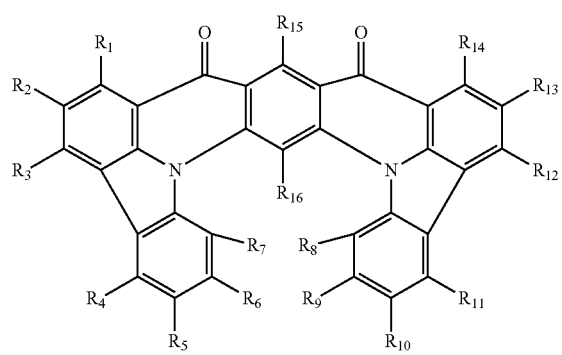

wherein in Formula 2-1, Formula 2-2, Formula 2-3, and Formula 2-5,

R₁ₐ, R₁ᵦ, R₂ₐ, and R₂ᵦ are each independently a hydrogen atom, a deuterium atom, a halogen atom, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms, and $R_1$ to $R_{16}$ are the same as defined in connection with Formula 1.

9. The light emitting device of claim 1, wherein the fused polycyclic compound represented by Formula 1 is represented by one of Formula 3-1 to Formula 3-13:

[Formula 3-1]

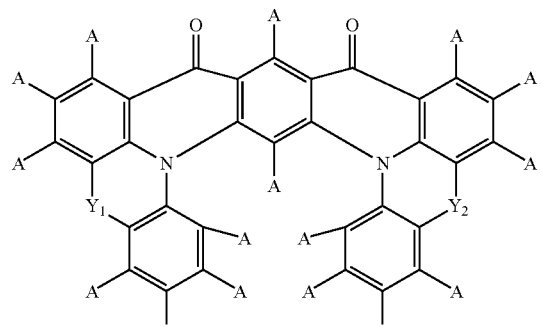

[Formula 3-2]

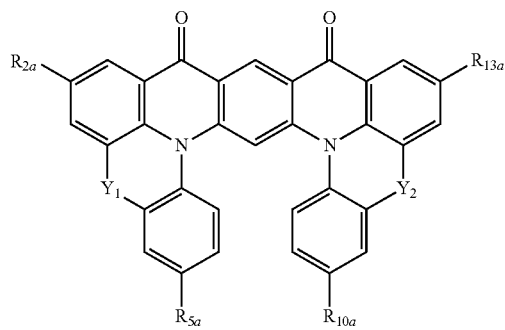

[Formula 3-3]

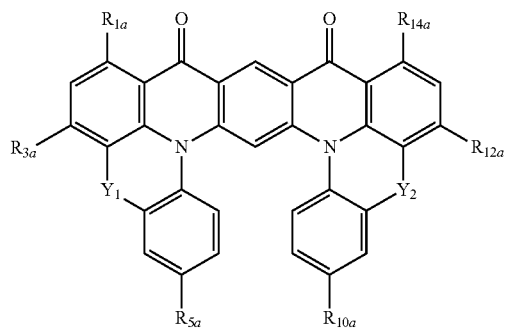

[Formula 3-4]

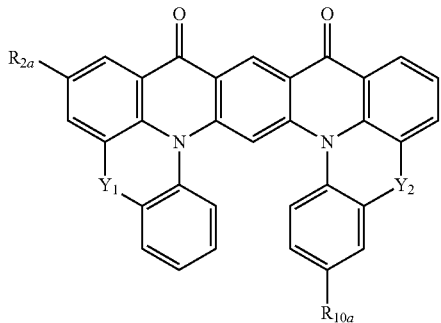

[Formula 3-5]

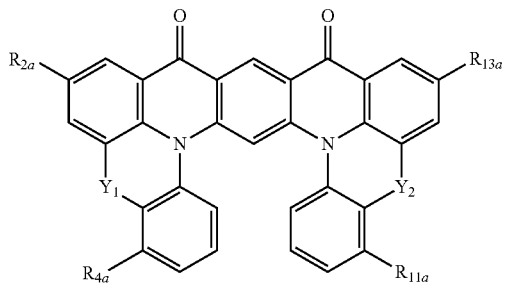

[Formula 3-6]

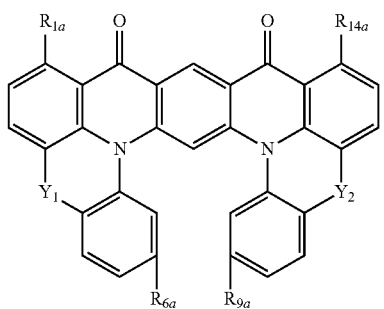

[Formula 3-7]

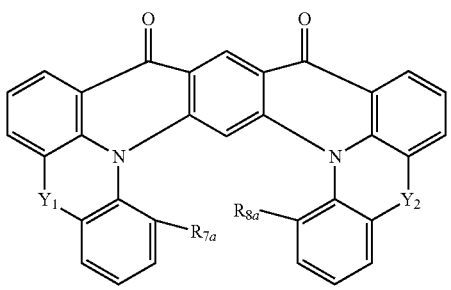

[Formula 3-8]

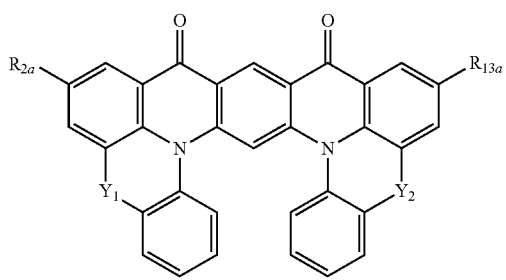

[Formula 3-9]

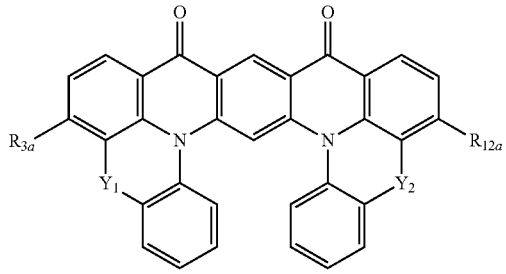

-continued

[Formula 3-10]

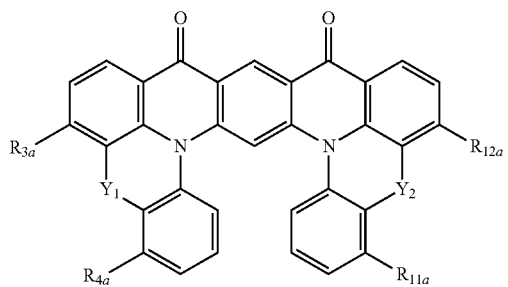

[Formula 3-11]

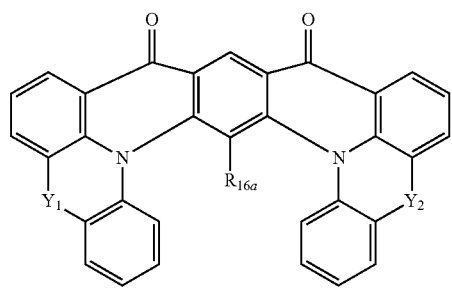

[Formula 3-12]

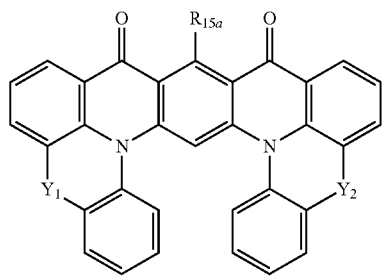

[Formula 3-13]

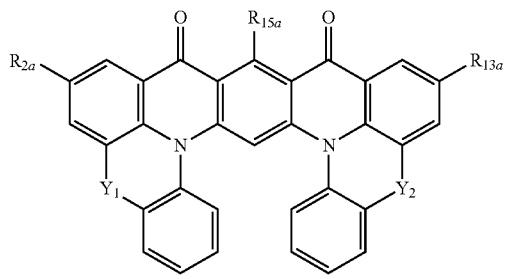

wherein in Formula 3-1 to Formula 3-13,
A is each independently a hydrogen atom or a deuterium atom,
$R_{1a}$ to $R_{16a}$ are each independently a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms, and
$Y_1$, $Y_2$, $R_{17}$, and $R_{18}$ are the same as defined in connection with Formula 1.

10. The light emitting device of claim 1, wherein in Formula 1, $R_1$ to $R_{18}$ are each independently a hydrogen atom, a deuterium atom, a substituted or unsubstituted amine group, a substituted or unsubstituted methyl group, a substituted or unsubstituted t-butyl group, a substituted or unsubstituted octyl group, a substituted or unsubstituted cyclohexyl group, a substituted or unsubstituted adamantyl group, a substituted or unsubstituted phenyl group, a substituted or unsubstituted naphthyl group, a substituted or unsubstituted anthracene group, or a substituted or unsubstituted fluorenyl group.

11. The light emitting device of claim 1, further comprising a capping layer disposed on the second electrode, wherein
the capping layer has a refractive index greater than or equal to about 1.6.

12. The light emitting device of claim 1, wherein the fused polycyclic compound comprises at least one selected from Compound Group 1:

[Compound Group 1]

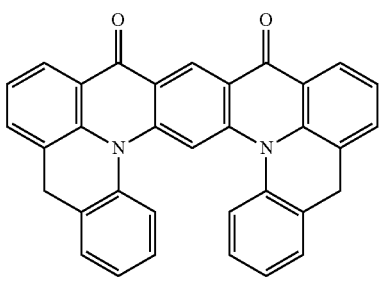

1

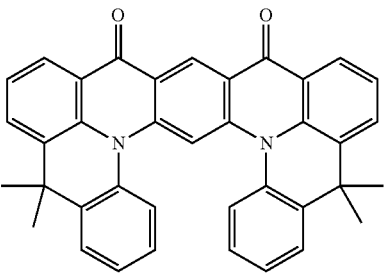

2

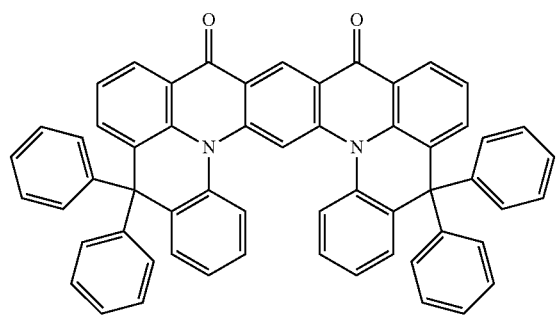

2

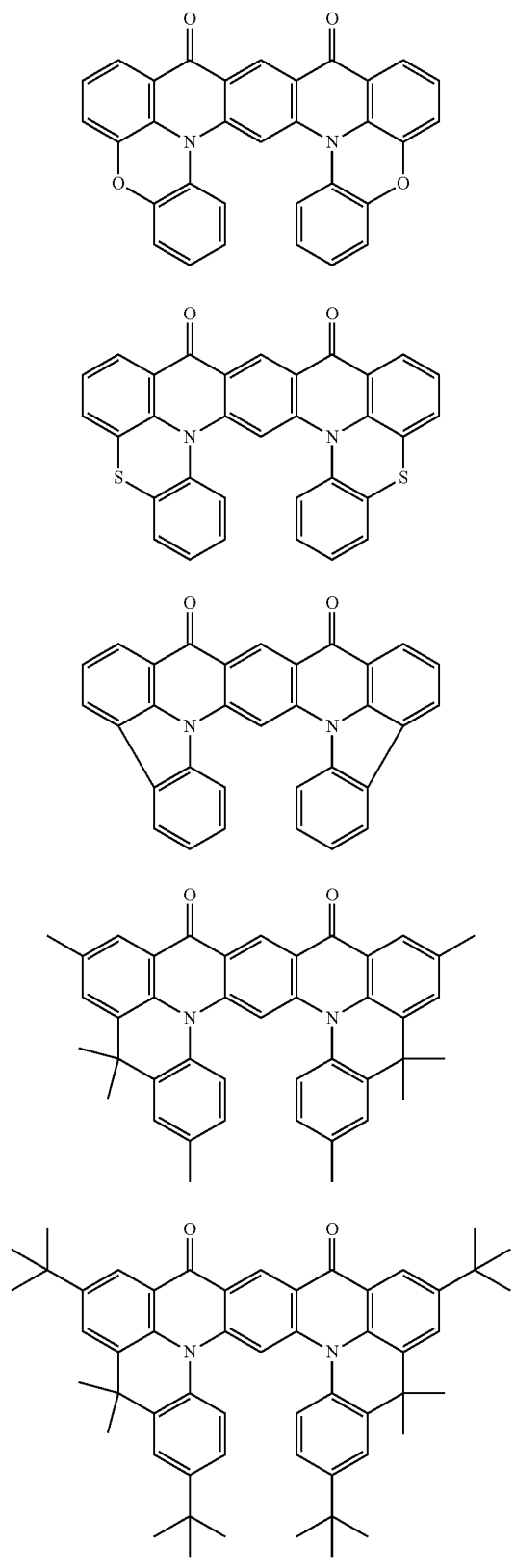
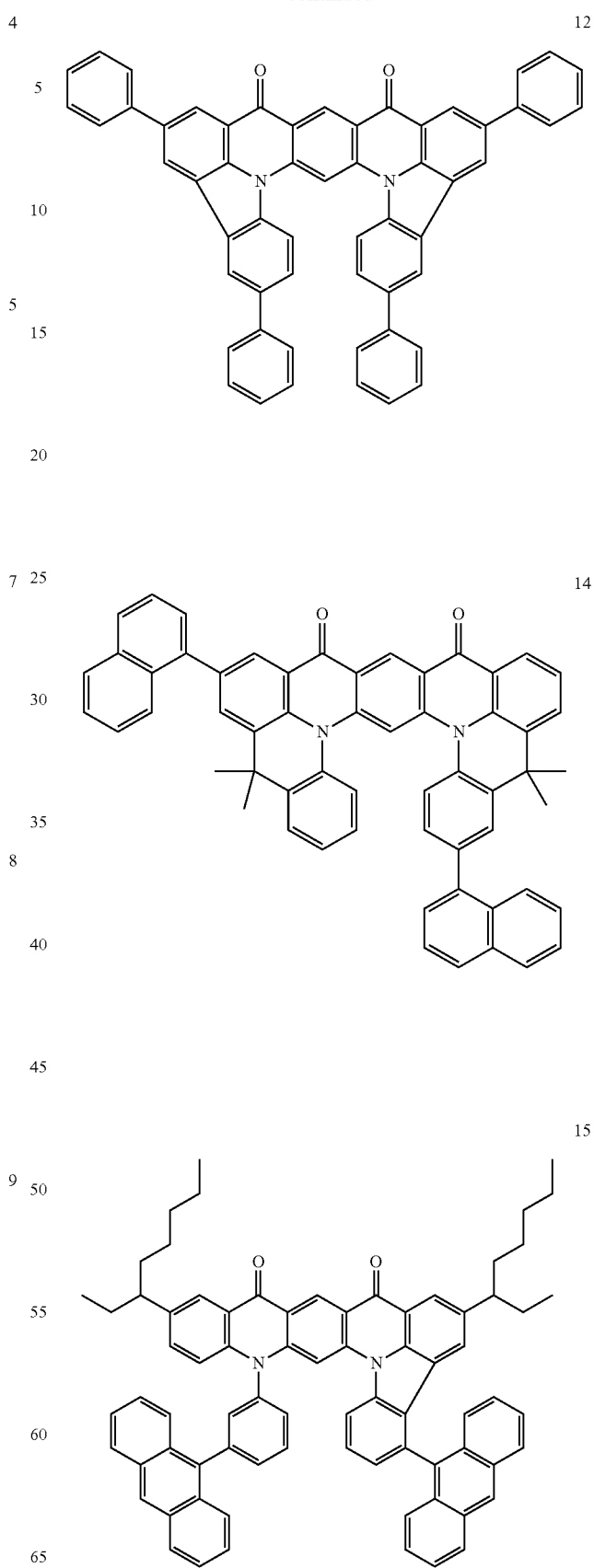

16
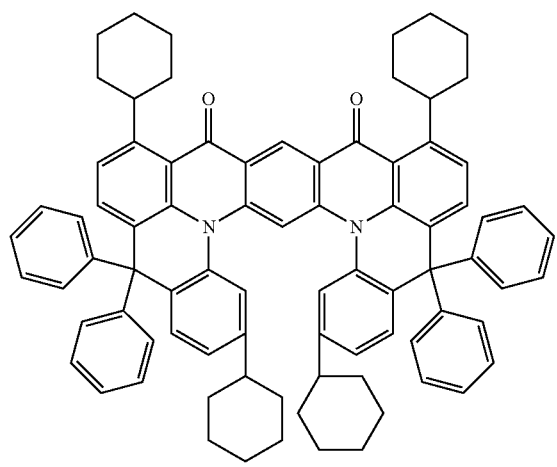
17
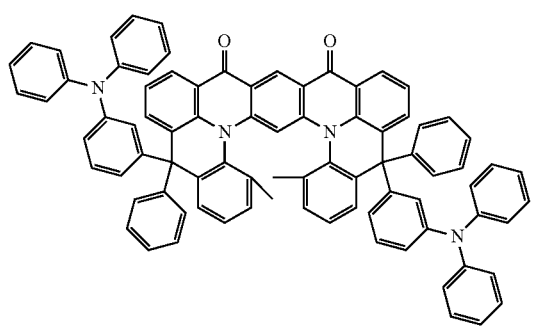
18
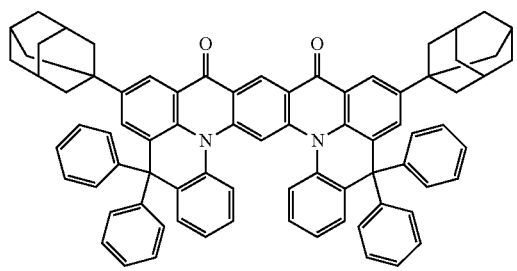
20
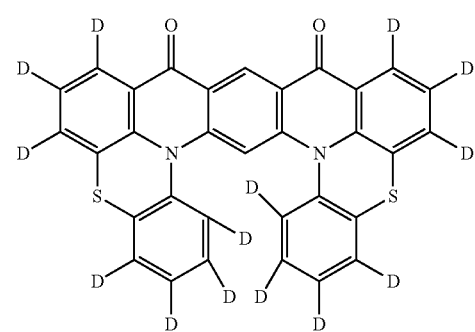
21
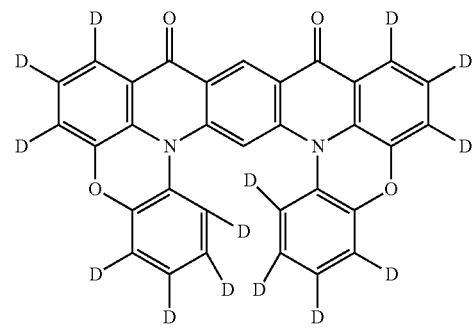
24
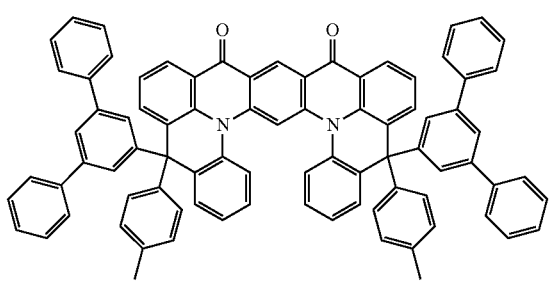
25
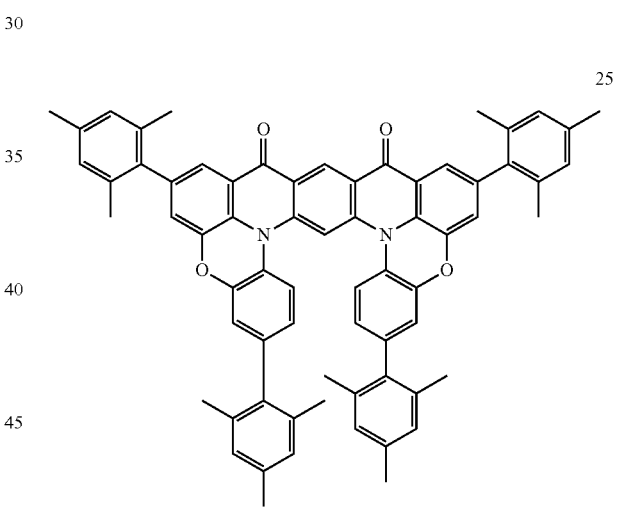
26
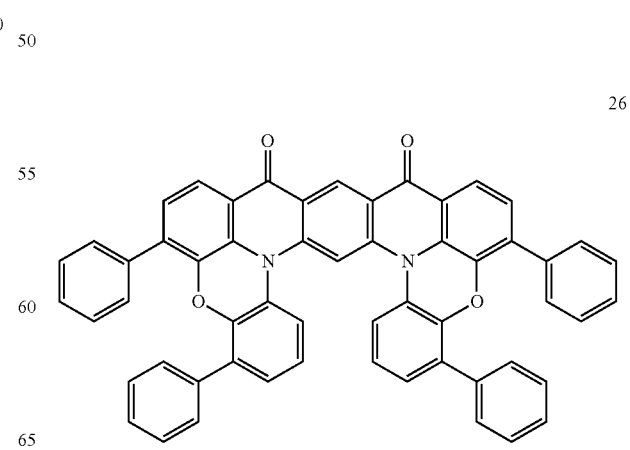

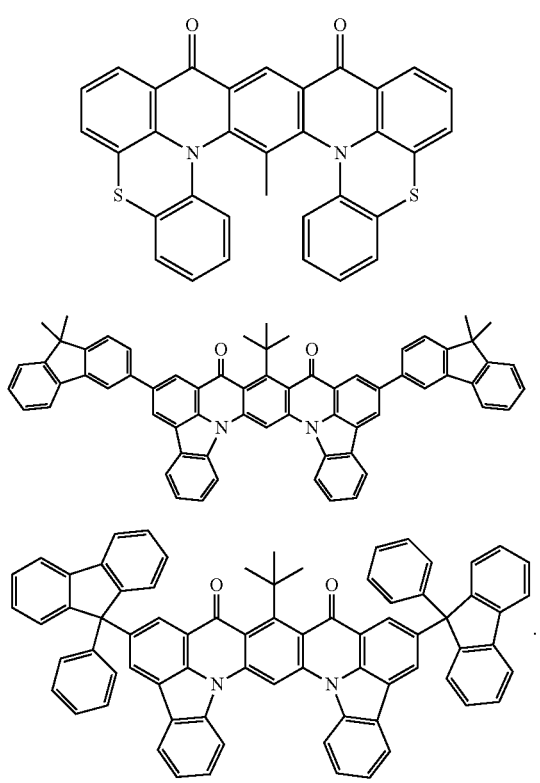

13. A light emitting device, comprising:
a first electrode;
a second electrode facing the first electrode; and
an emission layer disposed between the first electrode and the second electrode, wherein
the emission layer comprises a host and a delayed fluorescence dopant, and
the delayed fluorescence dopant comprises a fused polycyclic compound represented by Formula 1:

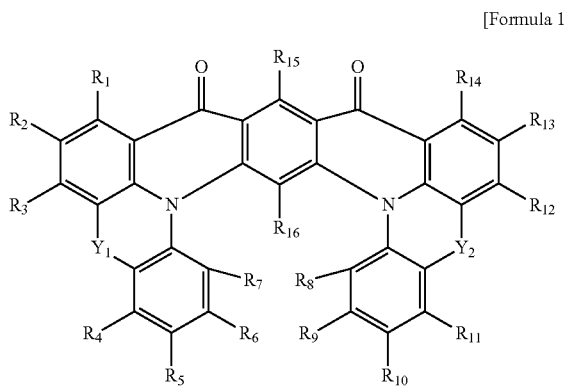

[Formula 1]

wherein in Formula 1,
$Y_1$ and $Y_2$ are each independently a direct linkage, —O—, —S—, or —C($R_{17}$)($R_{18}$)—,
$R_1$ to $R_{18}$ are each independently a hydrogen atom, a deuterium atom, a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms.

14. The light emitting device of claim 13, wherein the host comprises a compound represented by Formula E-2a or Formula E-2b:

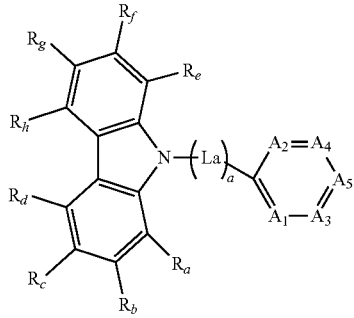

[Formula E-2a]

[Formula E-2b]

$(Cbz_1)\!-\!(L_b)_b\!-\!(Cbz_2)$ wherein in Formula E-2a,
a is an integer from 0 to 10,
$L_a$ is a direct linkage, a substituted or unsubstituted arylene group of 6 to 30 ring-forming carbon atoms, or a substituted or unsubstituted heteroarylene group of 2 to 30 ring-forming carbon atoms,
$A_1$ to $A_5$ are each independently N or C($R_i$),
$R_a$ to $R_i$ are each independently a hydrogen atom, a deuterium atom, a substituted or unsubstituted amine group, a substituted or unsubstituted thio group, a substituted or unsubstituted oxy group, a substituted or unsubstituted phosphine oxide group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring,
two or three of $A_1$ to $A_5$ are N, and
the remainder of $A_1$ to $A_5$ are C($R_i$), and
wherein in Formula E-2b,
Cbz1 and Cbz2 are each independently an unsubstituted carbazole group, or a carbazole group substituted with an aryl group of 6 to 30 ring-forming carbon atoms,
$L_b$ is a direct linkage, a substituted or unsubstituted arylene group of 6 to 30 ring-forming carbon atoms, or a substituted or unsubstituted heteroarylene group of 2 to 30 ring-forming carbon atoms, and
b is an integer from 0 to 10.

15. The light emitting device of claim 13, wherein in Formula 1, $Y_1$ and $Y_2$ are the same.

16. The light emitting device of claim 13, wherein in Formula 1,
$R_1$ and $R_{14}$ are the same,
$R_2$ and $R_{13}$ are the same,
$R_3$ and $R_{12}$ are the same,
$R_4$ and $R_{11}$ are the same,
$R_5$ and $R_{10}$ are the same, $R_6$ and $R_9$ are the same, and
$R_7$ and $R_8$ are the same.

17. The light emitting device of claim 13, wherein the fused polycyclic compound represented by Formula 1 is represented by Formula 2-1, Formula 2-2, Formula 2-3, or Formula 2-5:

[Formula 2-1]
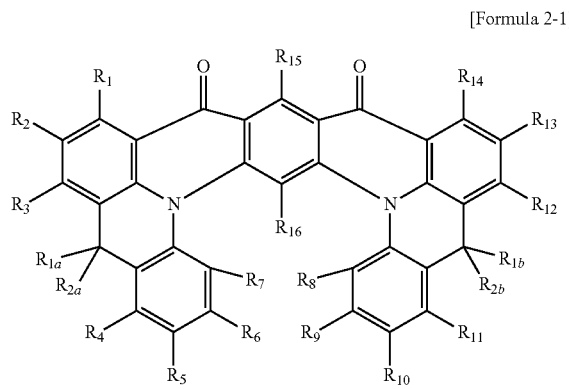

[Formula 2-2]
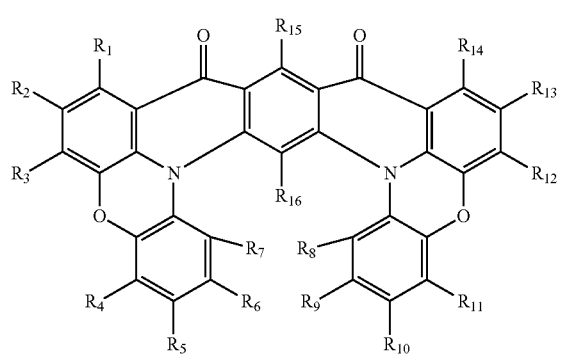

[Formula 2-3]
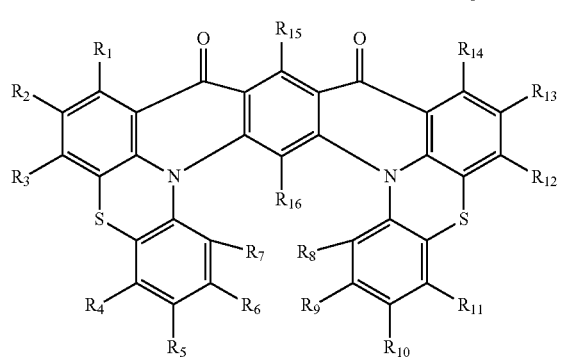

[Formula 2-4]
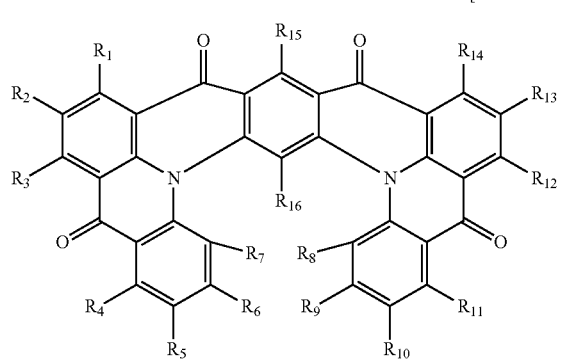

[Formula 2-5]
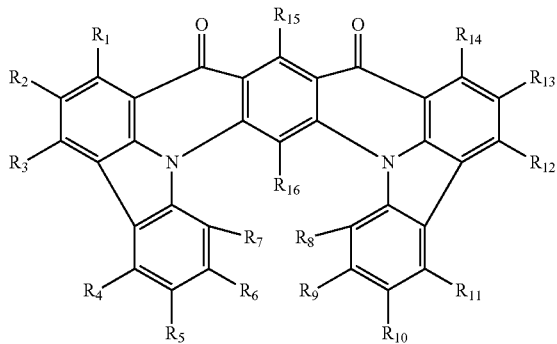

wherein in Formula 2-1, Formula 2-2, Formula 2-3, and Formula 2-5, $R_{1a}$, $R_{1b}$, $R_{2a}$, and $R_{2b}$ are each independently a hydrogen atom, a deuterium atom, a halogen atom, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms, and $R_1$ to $R_{16}$ are the same as defined in connection with Formula 1.

18. The light emitting device of claim 13, wherein the fused polycyclic compound represented by Formula 1 is represented by one of Formula 3-1 to Formula 3-13:

[Formula 3-1]
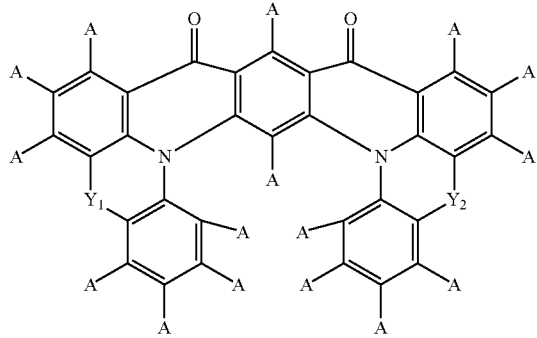

[Formula 3-2]
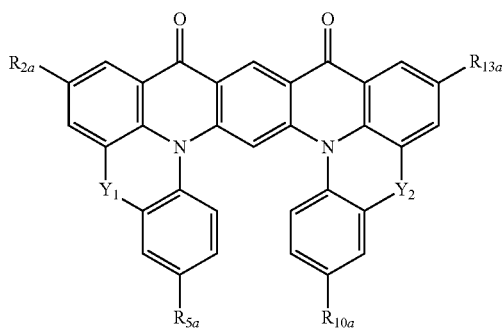

[Formula 3-3]

[Formula 3-4]

[Formula 3-5]

[Formula 3-6]

[Formula 3-7]

[Formula 3-8]

[Formula 3-9]

[Formula 3-10]

[Formula 3-11]

[Formula 3-12]

[Formula 3-13]

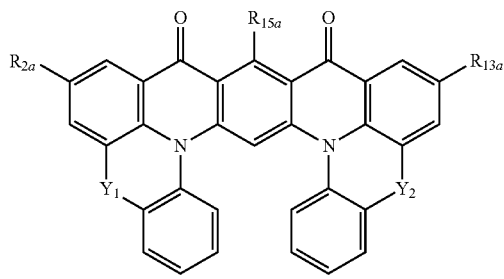

wherein in Formula 3-1 to Formula 3-13,

A is each independently a hydrogen atom or a deuterium atom, $R_{1a}$ to $R_{16a}$ are each independently a halogen atom, a cyano group, a nitro group, a substituted or unsubstituted amine group, a substituted or unsubstituted silyl group, a substituted or unsubstituted boron group, a substituted or unsubstituted oxy group, a substituted or unsubstituted carbonyl group, a substituted or unsubstituted alkyl group of 2 to 30 carbon atoms, a substituted or unsubstituted aryl group of 6 to 60 ring-forming carbon atoms, or a substituted or unsubstituted heteroaryl group of 2 to 60 ring-forming carbon atoms, and $Y_1$, $Y_2$, $R_{17}$, and $R_{18}$ are the same as defined in connection with Formula 1.

19. The light emitting device of claim 13, wherein in Formula 1, $R_1$ to $R_{18}$ are each independently a hydrogen atom, a deuterium atom, a substituted or unsubstituted amine group, a substituted or unsubstituted methyl group, a substituted or unsubstituted t-butyl group, a substituted or unsubstituted octyl group, a substituted or unsubstituted cyclohexyl group, a substituted or unsubstituted adamantyl group, a substituted or unsubstituted phenyl group, a substituted or unsubstituted naphthyl group, a substituted or unsubstituted anthracene group, or a substituted or unsubstituted fluorenyl group.

20. The light emitting device of claim 13, wherein the fused polycyclic compound comprises at least one selected from Compound Group 1:

[Compound Group 1]

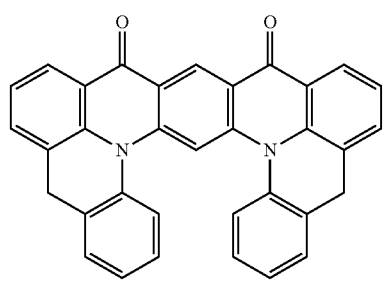

1

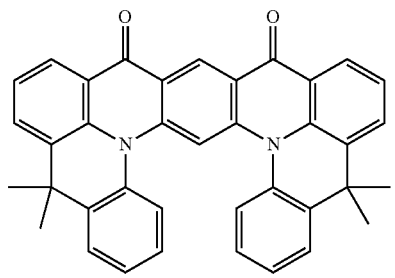

2

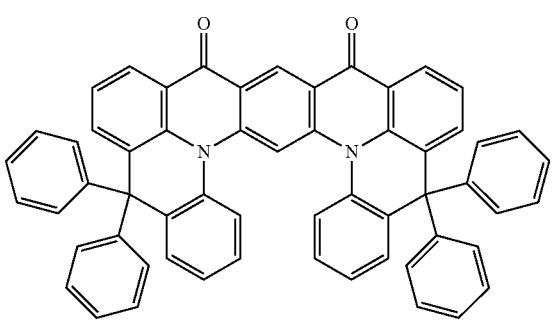

2

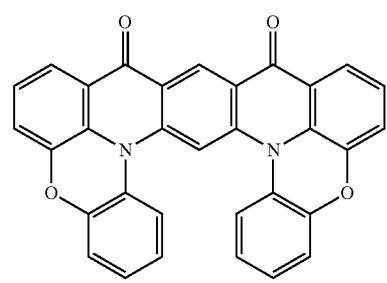

4

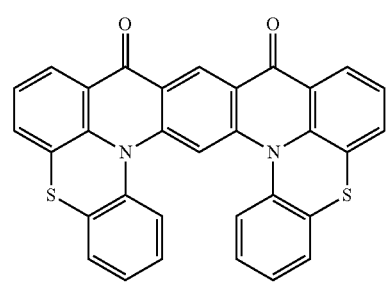

5

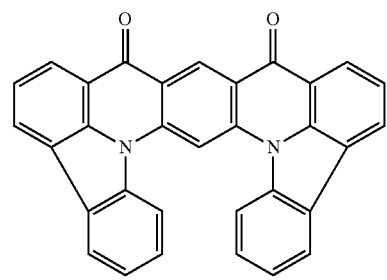

7

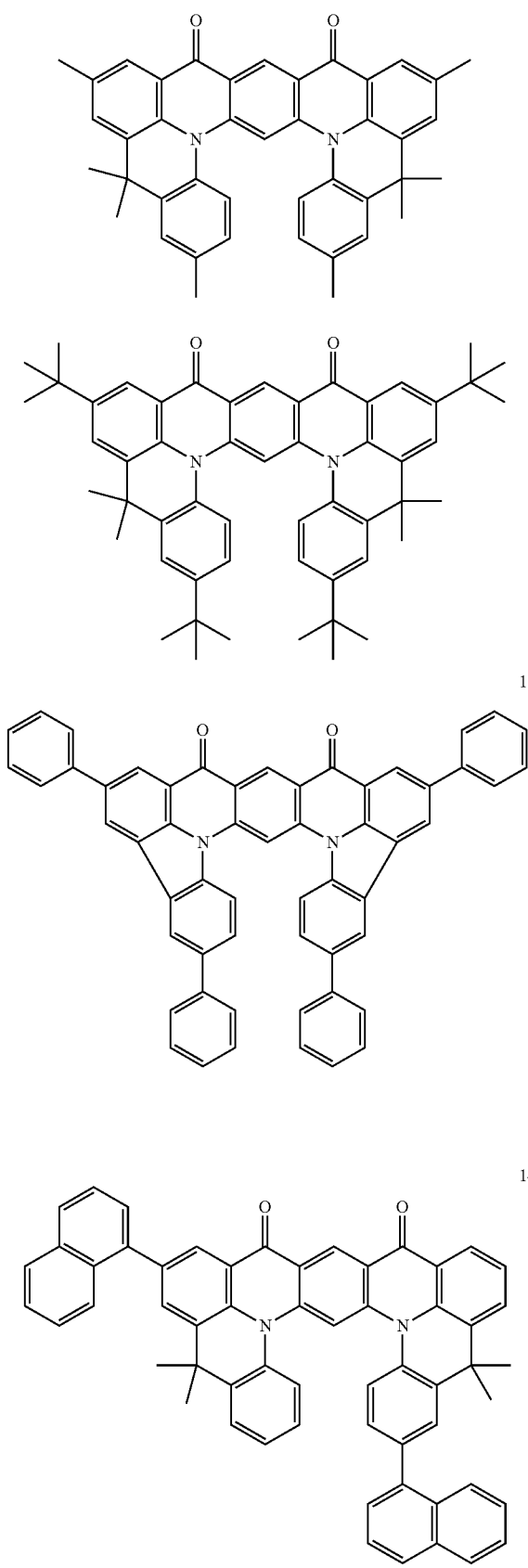
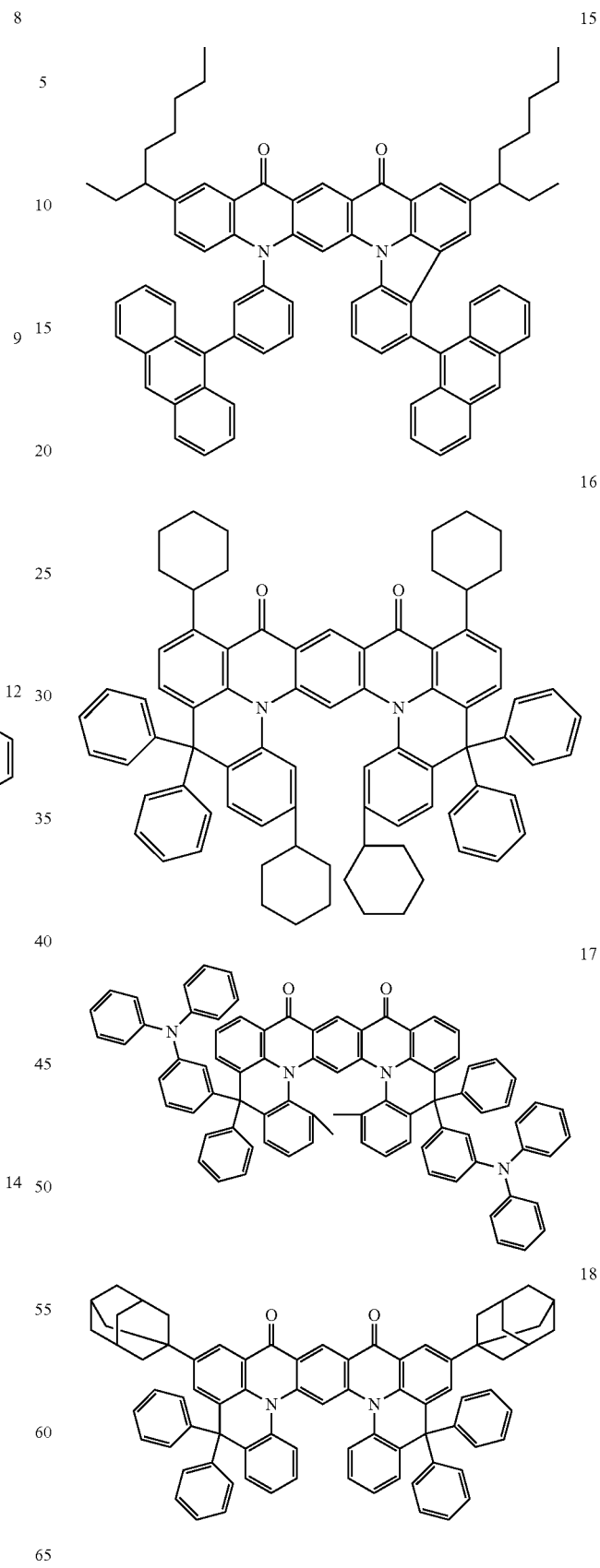

117
-continued
20
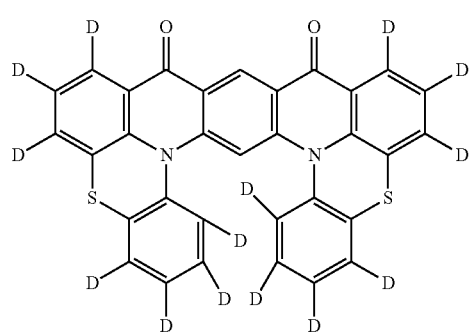
21
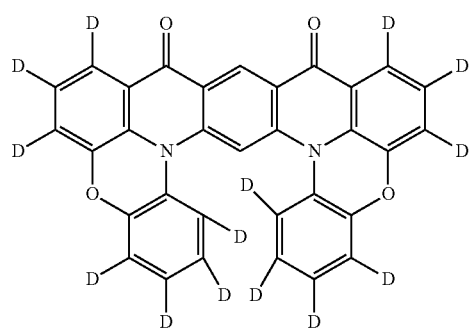
24
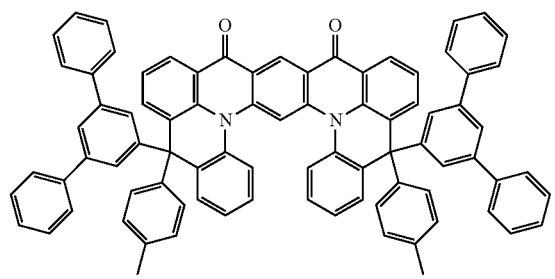
25
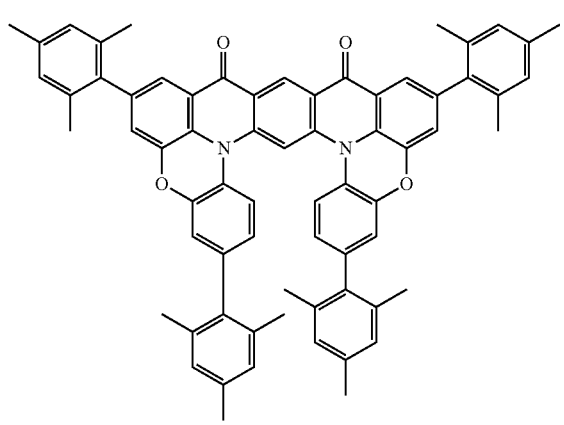
118
-continued
26
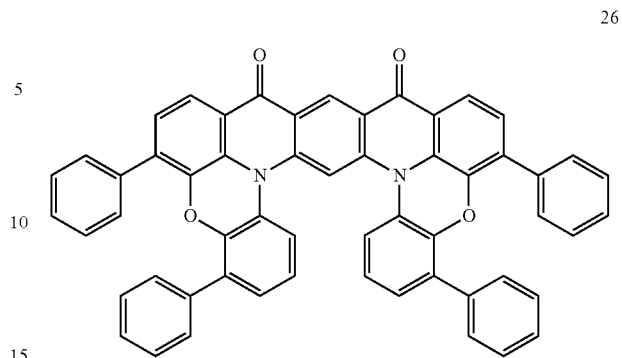
27
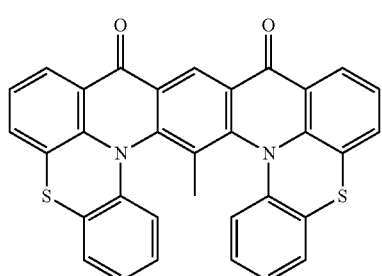
30
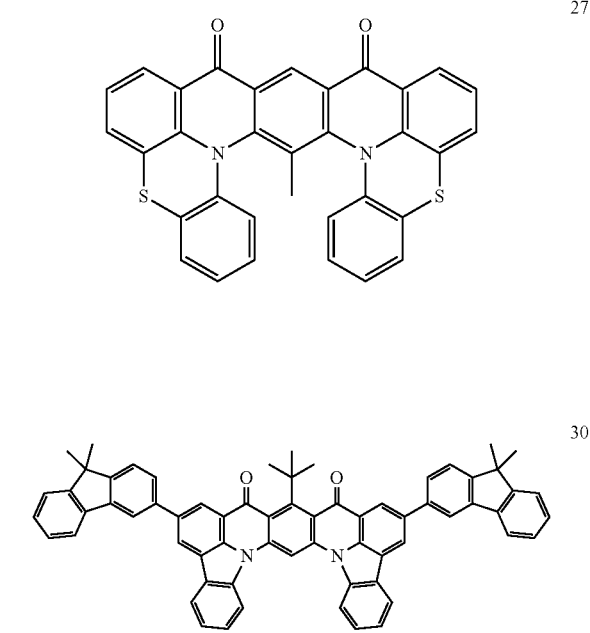
31
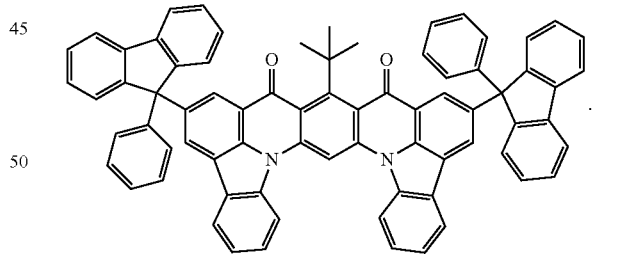
* * * * *